(12) United States Patent
Xia

(10) Patent No.: US 11,512,038 B2
(45) Date of Patent: Nov. 29, 2022

(54) TETRAPHENYLENE TRIARYLAMINE COMPOUNDS

(71) Applicant: BEIJING SUMMER SPROUT TECHNOLOGY CO., LTD., Beijing (CN)

(72) Inventor: Chuanjun Xia, Lawrenceville, NJ (US)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 279 days.

(21) Appl. No.: 16/223,135

(22) Filed: Dec. 18, 2018

(65) Prior Publication Data

US 2019/0185412 A1 Jun. 20, 2019

Related U.S. Application Data

(60) Provisional application No. 62/607,331, filed on Dec. 19, 2017.

(51) Int. Cl.
*C07C 211/61* (2006.01)
*H01L 51/00* (2006.01)
*H01L 51/50* (2006.01)

(52) U.S. Cl.
CPC .......... *C07C 211/61* (2013.01); *H01L 51/006* (2013.01); *H01L 51/0054* (2013.01); *H01L 51/0055* (2013.01); *H01L 51/0057* (2013.01); *H01L 51/0061* (2013.01); *H01L 51/5088* (2013.01); *H01L 51/5096* (2013.01);
(Continued)

(58) Field of Classification Search
CPC .............. C07C 211/61; C07C 2603/52; C07D 209/86; C07D 307/91; C07D 333/76; C07D 491/048; C07D 495/04; H01L 51/0054; H01L 51/0055; H01L 51/0057; H01L 51/0058; H01L 51/006; H01L 51/0061; H01L 51/0072; H01L 51/0073;
(Continued)

(56) References Cited

U.S. PATENT DOCUMENTS 5,703,436 A 12/1997 Forrest et al.
5,707,745 A 1/1998 Forrest et al.
(Continued)

FOREIGN PATENT DOCUMENTS

CN 1412864 A 4/2003
CN 106848070 A 6/2017
(Continued)

OTHER PUBLICATIONS

National Science Review, 4: 892-916, (2017). (Year: 2017).*
(Continued)

*Primary Examiner* — Dawn L Garrett
(74) *Attorney, Agent, or Firm* — Alston & Bird LLP

(57) ABSTRACT

Tetraphenylene triarylamine compounds are disclosed, which are novel triarylamine compounds containing tetraphenylene building block. The compounds can be used as charge transporting materials, hole transporting materials, hole injection materials, electron blocking materials, etc., in an electroluminescent device. These novel compounds have good sublimation characters, and can offer more controllable charge transporting performance and good OLED device performance. Also disclosed are an organic electroluminescent device and a formulation.

13 Claims, 2 Drawing Sheets

Figure 1:
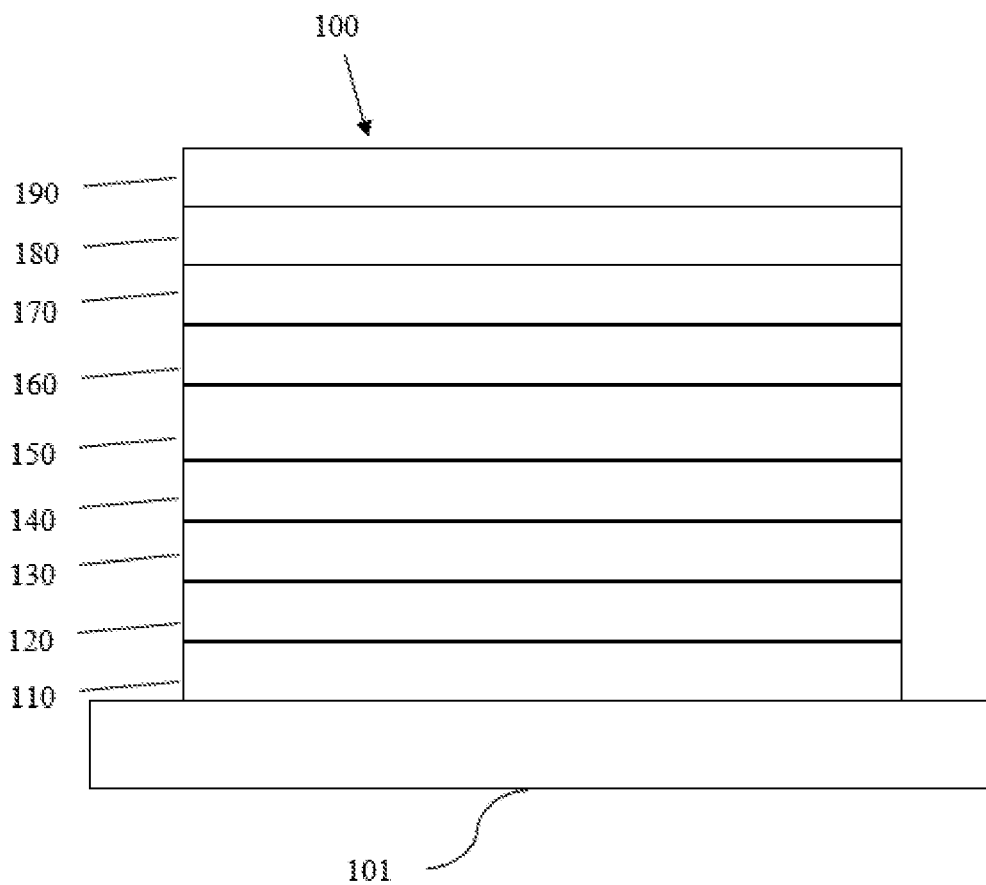

(52) U.S. Cl.
CPC ...... *C07C 2603/52* (2017.05); *H01L 51/0058* (2013.01); *H01L 51/0072* (2013.01); *H01L 51/0073* (2013.01); *H01L 51/0074* (2013.01); *H01L 51/0085* (2013.01); *H01L 51/5056* (2013.01)

(58) Field of Classification Search
CPC ............. H01L 51/0074; H01L 51/0085; H01L 51/5056; H01L 51/5088; H01L 51/5096
See application file for complete search history.

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 6,416,887 | B1* | 7/2002 | Tokito ............... C07C 211/61 313/504 |
| 7,279,704 | B2 | 10/2007 | Walters et al. |
| 7,968,146 | B2 | 6/2011 | Wagner et al. |
| 2001/0006741 | A1 | 7/2001 | Ishikawa et al. |
| 2003/0118866 | A1* | 6/2003 | Oh ..................... H01L 51/006 428/690 |
| 2003/0230980 | A1 | 12/2003 | Forrest et al. |
| 2004/0124766 | A1* | 7/2004 | Nakagawa .......... H01L 51/0073 313/504 |
| 2004/0174116 | A1 | 9/2004 | Lu et al. |
| 2005/0112407 | A1 | 5/2005 | Ogasawara et al. |
| 2006/0166034 | A1* | 7/2006 | Saitoh ................ H01L 51/0072 428/690 |
| 2007/0138953 | A1* | 6/2007 | Tobise ................ H01L 51/5048 313/506 |
| 2008/0213624 | A1* | 9/2008 | Lecloux .............. H01L 51/0043 428/691 |
| 2013/0105771 | A1* | 5/2013 | Ryu ..................... C09B 57/00 257/40 |
| 2013/0207046 | A1* | 8/2013 | Pflumm ............... C07D 219/02 252/500 |
| 2014/0131665 | A1 | 5/2014 | Xia et al. |
| 2014/0158992 | A1 | 6/2014 | Xia et al. |
| 2015/0349273 | A1 | 12/2015 | Hung et al. |
| 2016/0013422 | A1 | 1/2016 | Kwong et al. |
| 2016/0060251 | A1 | 3/2016 | Xia et al. |
| 2016/0093810 | A1* | 3/2016 | Miyake ................ C07D 405/14 548/440 |
| 2016/0343951 | A1 | 11/2016 | Kwong et al. |
| 2016/0359122 | A1 | 12/2016 | Boudreault et al. |
| 2017/0018710 | A1* | 1/2017 | Mujica-Fernaud ... H01L 51/006 |
| 2017/0018721 | A1 | 1/2017 | Tsang et al. |
| 2017/0077409 | A1 | 5/2017 | Kwong et al. |
| 2017/0162816 | A1 | 6/2017 | Kim et al. |
| 2017/0271611 | A1* | 9/2017 | Li ........................ H01L 51/508 |
| 2018/0108844 | A1 | 4/2018 | Lee et al. |
| 2019/0036031 | A1 | 1/2019 | Wolohan et al. |
| 2019/0100544 | A1 | 4/2019 | Xia |
| 2019/0115541 | A1 | 4/2019 | Xia |
| 2019/0123286 | A1 | 4/2019 | Xia |

FOREIGN PATENT DOCUMENTS

| | | |
|---|---|---|
| CN | 110713492 | 1/2020 |
| JP | 2007-210964 A * | 8/2007 |
| WO | 2016/181911 A1 | 11/2016 |

OTHER PUBLICATIONS

Pan et al., Beilstein Journal of Organic Chemistry, (2016), vol. 12, pp. 1302-1308. (Year: 2016).*

C.W. Tang et al. "Organic electroluminescent diodes", Appl. Phys. Ltt. 51, 913 (1987); doi: 10.1063/1.98799.

Hiroki Uoyama et al. "Highli efficient organic light-emitting diodes from delayed fluorescence", doi:10.1038/nature 11687, 234, Nature, vol. 492, Dec. 13, 2012.

Shulei Pan, et al., "Synthesis of 2-substituted tetraphenylenes via transitionmetal-catalyzed derivatization of tetraphenylene", Beilstein Journal Of Organic Chemistry, 2016, 12, 1302-1308.

CN Office Action, including Search Report, dated Jul. 19, 2021 for CN Application No. 201811493087, 7 pages.

English Translation of CN Office Action, including Search Report, dated Jul. 19, 2021 for CN Application No. 201811493087, 7 pages.

* cited by examiner

TETRAPHENYLENE TRIARYLAMINE COMPOUNDS

This application claims the benefit of U.S. Provisional Application No. 62/607,331, filed Dec. 19, 2017, the entire content of which is incorporated herein by reference.

1 FIELD OF THE INVENTION

The present invention relates to a compound for organic electronic devices, such as organic light emitting devices. More specifically, the present invention relates to compounds having a tetraphenylene triarylamine structure, an organic electroluminescent device and a formulation comprising the compounds.

2 BACKGROUND ART

An organic electronic device is preferably selected from the group consisting of organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Tetraphenylene consists of four benzene rings that are ortho-annulated to form an eight-membered ring. It has a nonplanar saddle-shaped structure, with the two opposite pairs of benzene rings oriented above or below the average plane of the molecule. Due to their unique geometry, tetraphenylene and its derivatives may be used in OLED applications. Triarylamine type materials have good electron-donating properties and high hole mobility, and are therefore used as hole transporting materials in OLEDs. However, the application of the combination of the tetraphenylene structure and the triarylamine structure in OLED materials has not yet been developed. The present invention discloses a novel triarylamine compound containing tetraphenylene building block. The saddle-shaped structure of tetraphenylene reduces solid state packing and lowers the crystallinity of the compound, and can effectively control the charge transporting performance, offer good OLED device performance.

3 SUMMARY OF THE INVENTION

The present invention aims to provide a new series of tetraphenylene triarylamine compounds to solve at least part of the above problems. The compounds can be used as charge transporting materials, hole transporting materials, hole injection materials, electron blocking materials etc. in an organic electroluminescent device. These novel compounds have good sublimation characters, and offer more controllable charge transporting performance and good OLED device performance.

According to an embodiment of the present invention, a compound having Formula 1 is disclosed:

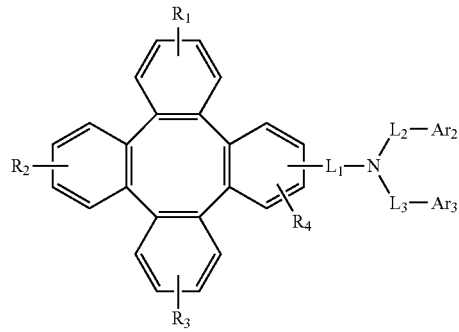

Formula 1 wherein $R_1$, $R_2$, $R_3$ and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

$Ar_2$ and $Ar_3$ are each independently selected from the group consisting of a substituted or unsubstituted aryl group having 6 to 50 ring carbon atoms, a substituted or unsubstituted heteroaryl group having 5 to 50 ring atoms, and combinations thereof;

$L_1$, $L_2$ and $L_3$ are each independently selected from the group consisting of a single bond, an arylene group having 6 to 30 ring carbon atoms, a heteroarylene group having 5 to 30 ring atoms, and combinations thereof;

Any adjacent substitution can be optionally joined to form a ring or fused structure.

According to another embodiment, an organic electroluminescent device is disclosed, which comprises:

an anode, a cathode, and a series of organic layers disposed between the anode and cathode, wherein at least one of the organic layers comprises a compound having Formula 1:

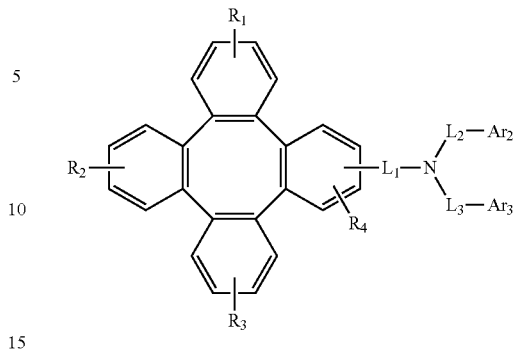

Formula 1 wherein $R_1$, $R_2$, $R_3$ and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

$Ar_2$ and $Ar_3$ are each independently selected from the group consisting of a substituted or unsubstituted aryl group having 6 to 50 ring carbon atoms, a substituted or unsubstituted heteroaryl group having 5 to 50 ring atoms, and combinations thereof;

$L_1$, $L_2$ and $L_3$ are each independently selected from the group consisting of a single bond, an arylene group having 6 to 30 ring carbon atoms, a heteroarylene group having 5 to 30 ring atoms, and combinations thereof;

Any adjacent substitution can be optionally joined to form a ring or fused structure.

According to yet another embodiment, a formulation comprising the compound according to Formula 1 is also disclosed.

The novel tetraphenylene triarylamine compounds disclosed in the present invention can be used as charge transporting materials, hole transporting materials, hole injection materials, electron blocking materials, etc. in an organic electroluminescent device. These novel compounds, which have good sublimation characters, are easier to be used in the fabrication of OLED, and can offer more controllable charge transporting performance and good OLED device performance.

4 BRIEF DESCRIPTION OF THE DRAWINGS

FIG. 1 schematically shows an organic light emitting device that can incorporate the compound disclosed herein.

Figure 2:
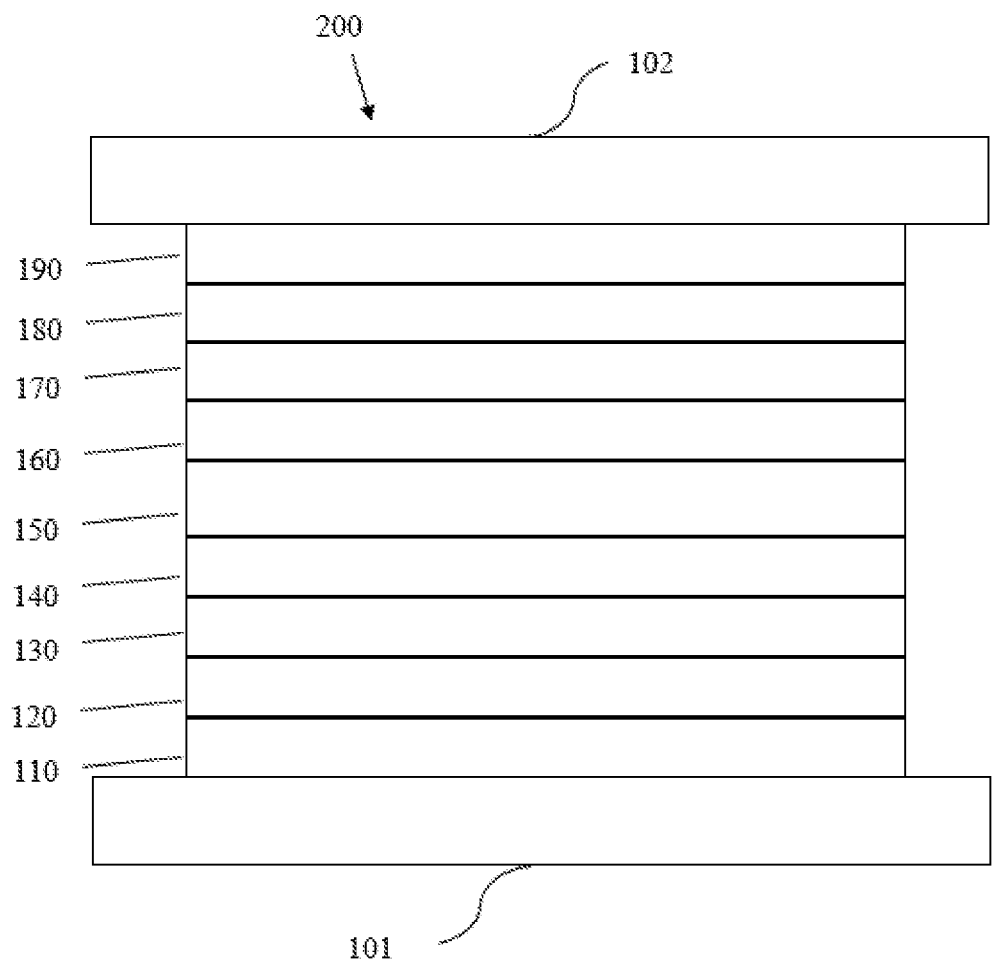

FIG. 2 schematically shows another organic electroluminescent device that can incorporate the compound material disclosed herein.

Figure 3:
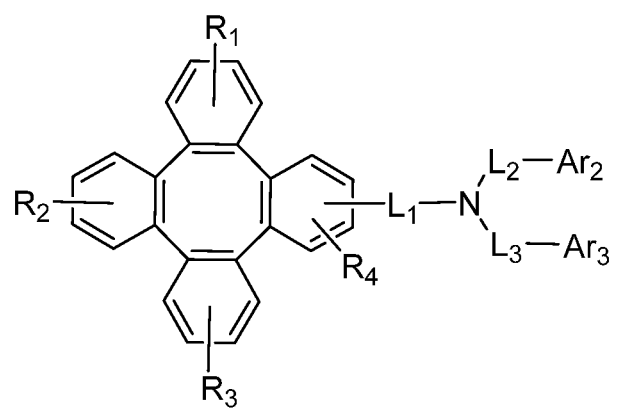

FIG. 3 shows the structural Formula 1 of compound disclosed herein.

5 DETAILED DESCRIPTION

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

An OLED can be encapsulated by a barrier layer to protect it from harmful species from the environment such as moisture and oxygen. FIG. 2 schematically shows the organic light emitting device 200 without limitation. FIG. 2 differs from FIG. 1 in that the organic light emitting device 200 include a barrier layer 102, which is above the cathode 190. Any material that can provide the barrier function can be used as the barrier layer such as glass and organic-inorganic hybrid layers. The barrier layer should be placed directly or indirectly outside of the OLED device. Multi-layer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions.

In the compounds mentioned in this disclosure, the expression that adjacent substituents are optionally joined to form a ring is intended to be taken to mean that two radicals are linked to each other by a chemical bond. This is illustrated by the following scheme:

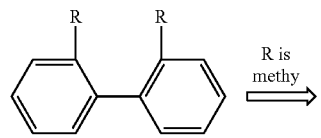

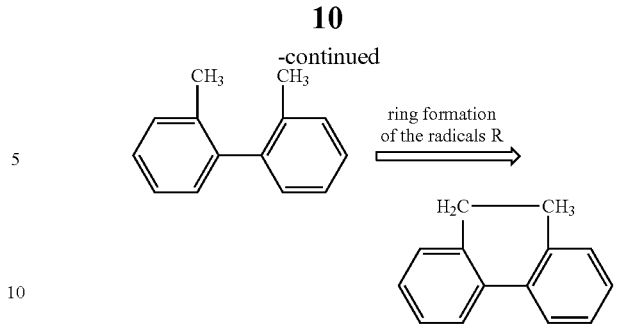

Furthermore, the expression that adjacent substituents are optionally joined to form a ring is also intended to be taken to mean that in the case where one of the two radicals represents hydrogen, the second radical is bonded at a position to which the hydrogen atom was bonded, with formation of a ring. This is illustrated by the following scheme:

According to an embodiment of the present invention, a compound having Formula 1 is disclosed:

Formula 1 wherein
$R_1$, $R_2$, $R_3$ and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

$Ar_2$ and $Ar_3$ are each independently selected from the group consisting of a substituted or unsubstituted aryl group having 6 to 50 ring carbon atoms, a substituted or unsubstituted heteroaryl group having 5 to 50 ring atoms, and combinations thereof;

$L_1$, $L_2$ and $L_3$ are each is independently selected from the group consisting of a single bond, an arylene group having 6 to 30 ring carbon atoms, a heteroarylene group having 5 to 30 ring atoms, and combinations thereof;

Any adjacent substitution can be optionally joined to form a ring or fused structure.

According to an embodiment of the present invention, wherein the compound has the formula:

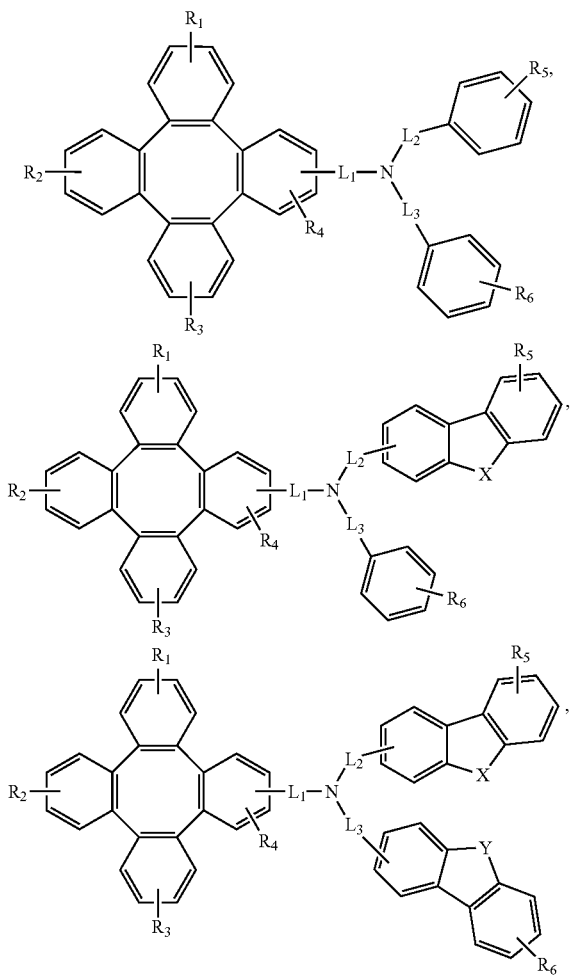

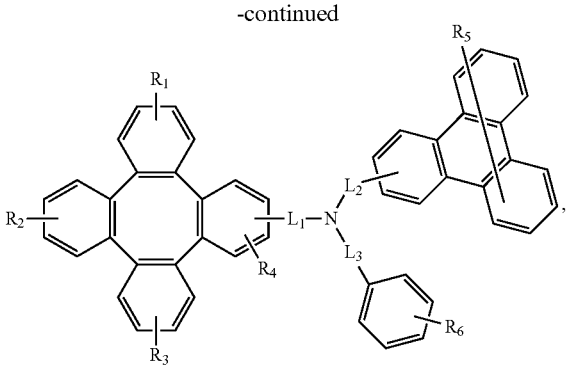

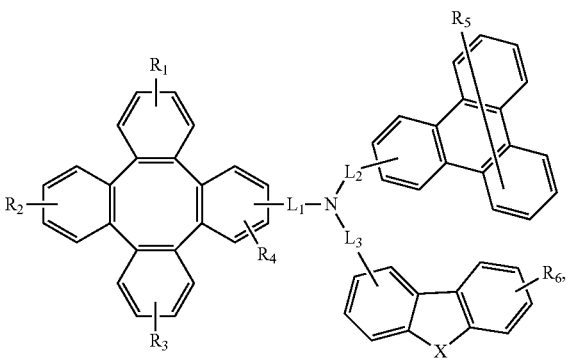

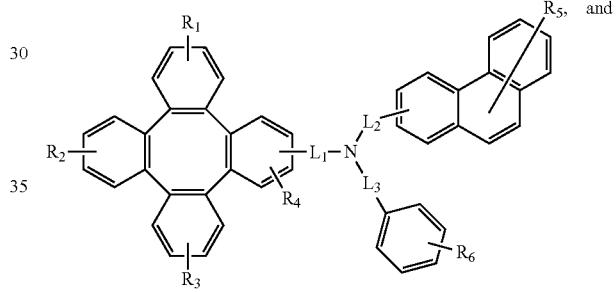

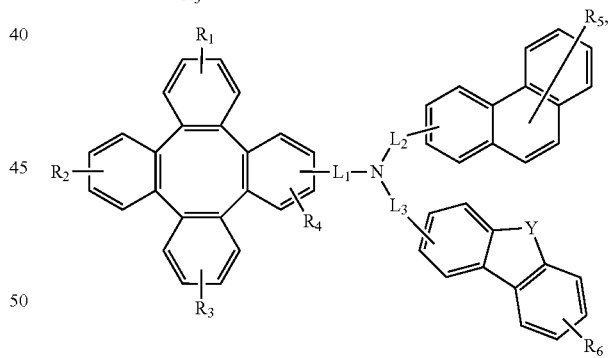

Wherein X and Y are each independently selected from the group consisting of O, S, Se, NR, and CR'R";

$L_1$, $L_2$ and $L_3$ are each independently selected from the group consisting of a single bond, an arylene group having 6 to 30 ring carbon atoms, a heteroarylene group having 5 to 30 ring atoms, and combinations thereof;

R, R', R", $R_1$, $R_2$, $R_3$, $R_4$, $R_5$ and $R_6$ are each independently selected from the group consisting of ydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

According to an embodiment of the present invention, wherein Ar₂ and Ar₃ are each independently selected from the group consisting of:

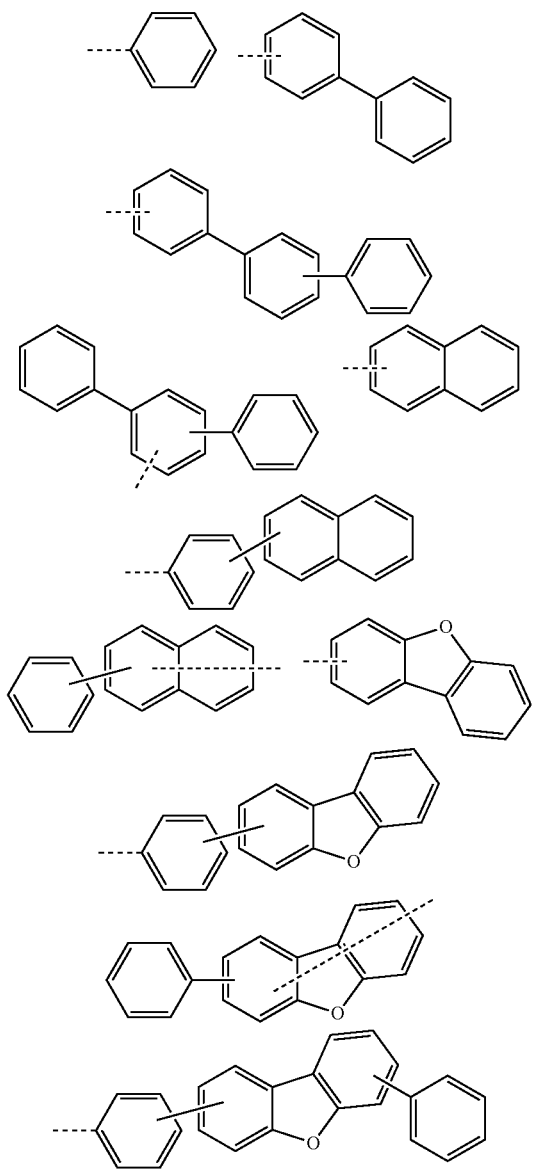

-continued

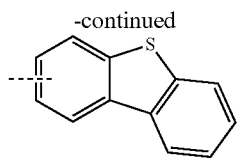

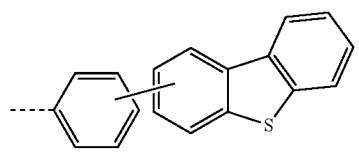

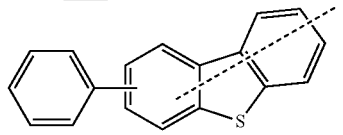

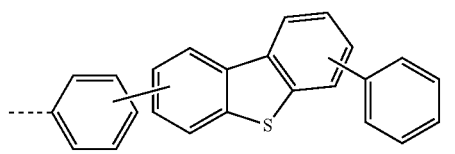

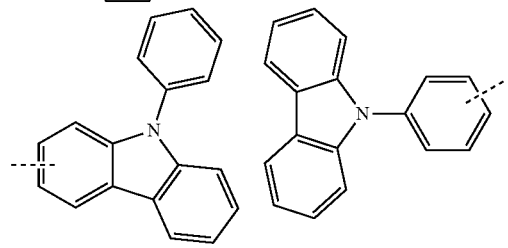

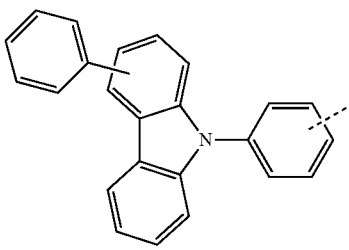

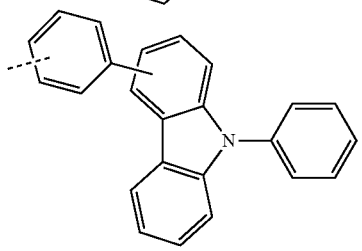

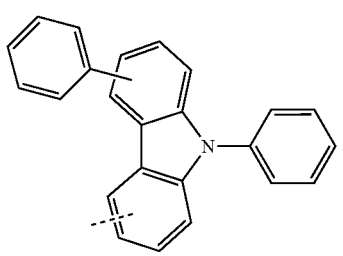

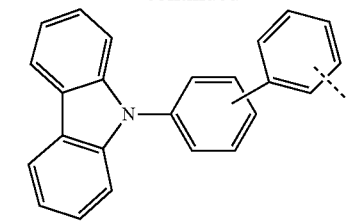
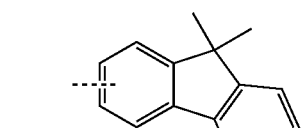
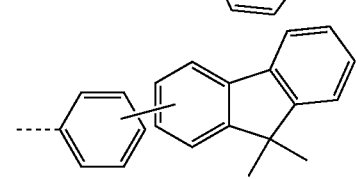
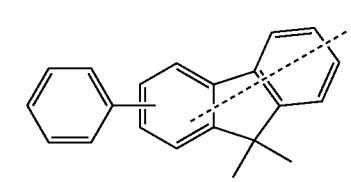
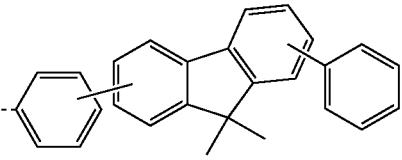
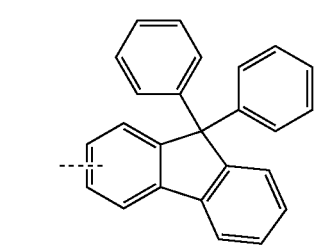
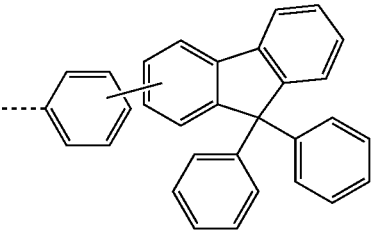
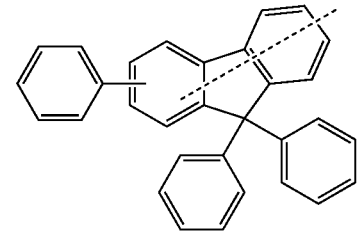
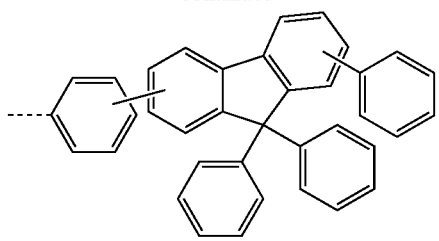
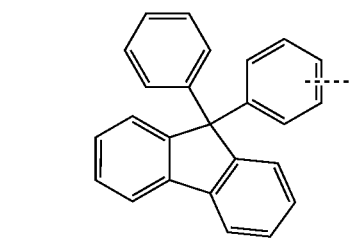
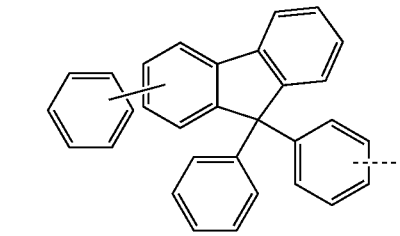
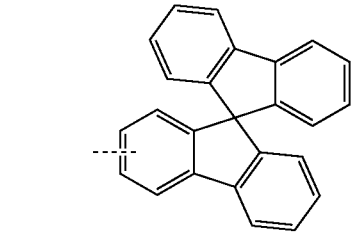
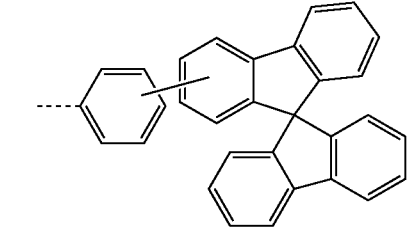
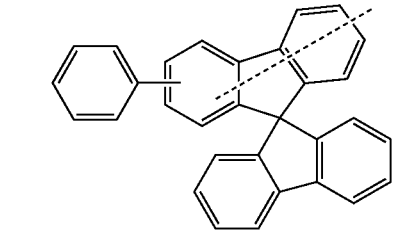
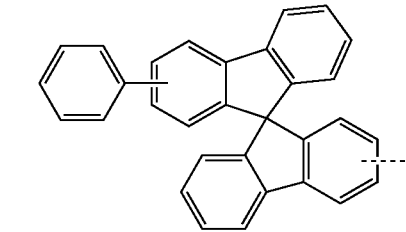

-continued
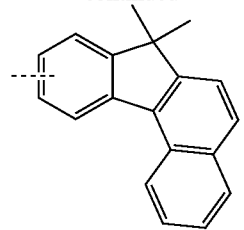
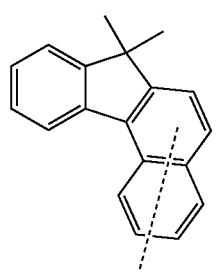
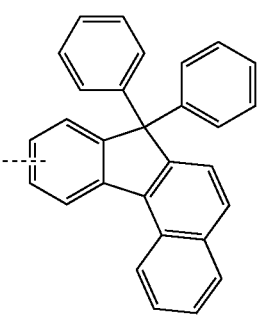
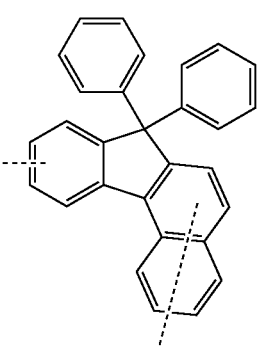
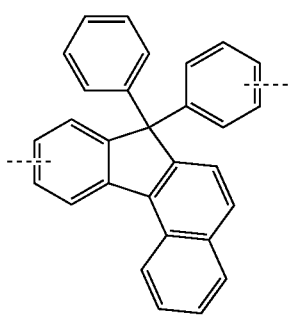
-continued
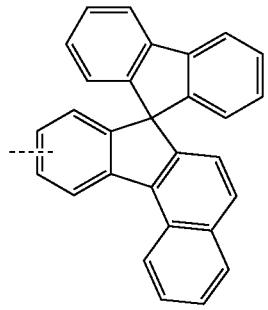
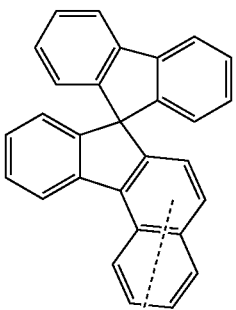
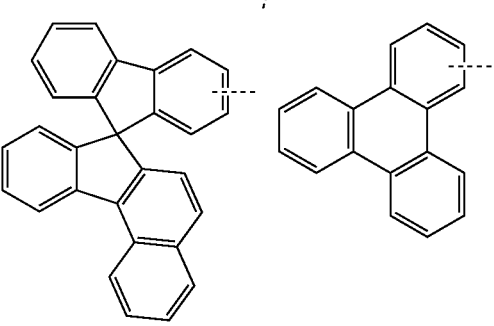
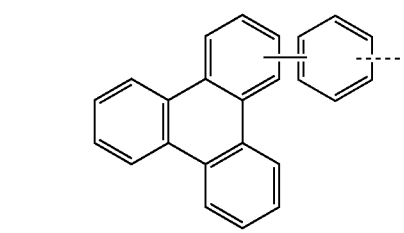
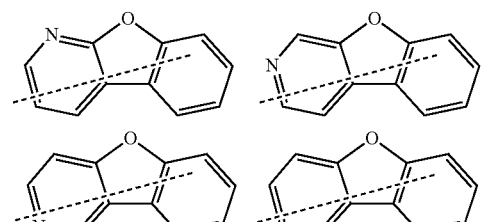
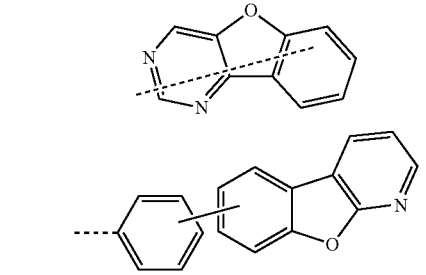

-continued

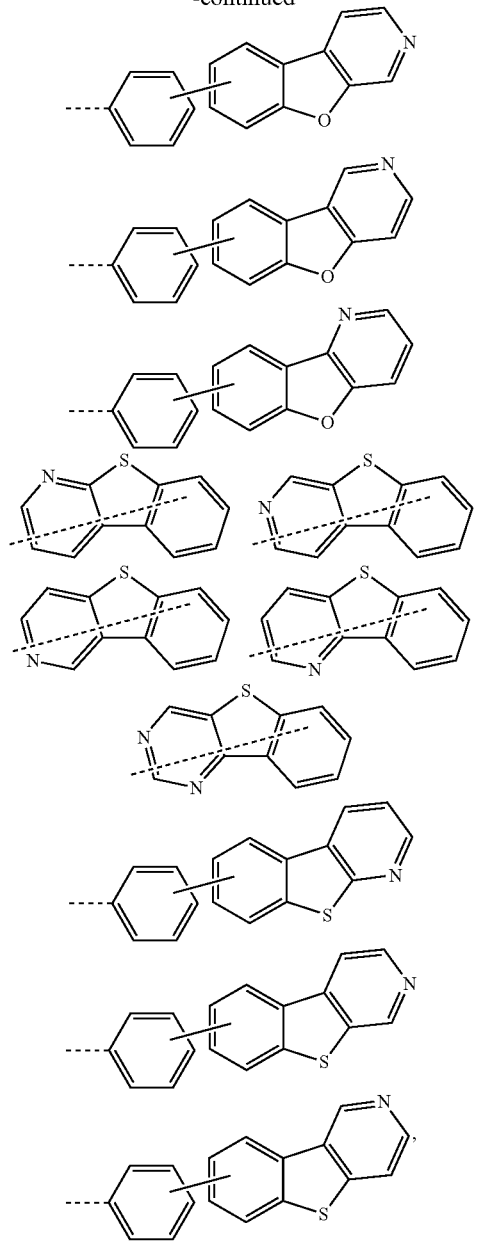

and combinations thereof.

According to an embodiment of the present invention, $Ar_2$ and $Ar_3$ are each independently selected from the group consisting of: phenyl, biphenyl, terphenyl, naphthyl, 9,9-dimethylfluorene, 9,9-diphenylfluorene, 9,9-spirobifluorene, dibenzofuran, dibenzothiophene, triphenylene, phenanthrene, N-phenylcarbazole, azadibenzofuran, azadibenzothiophene, and combinations thereof.

According to an embodiment of the present invention, wherein $L_1$, $L_2$ and $L_3$ are each independently selected from the group consisting of:

-continued

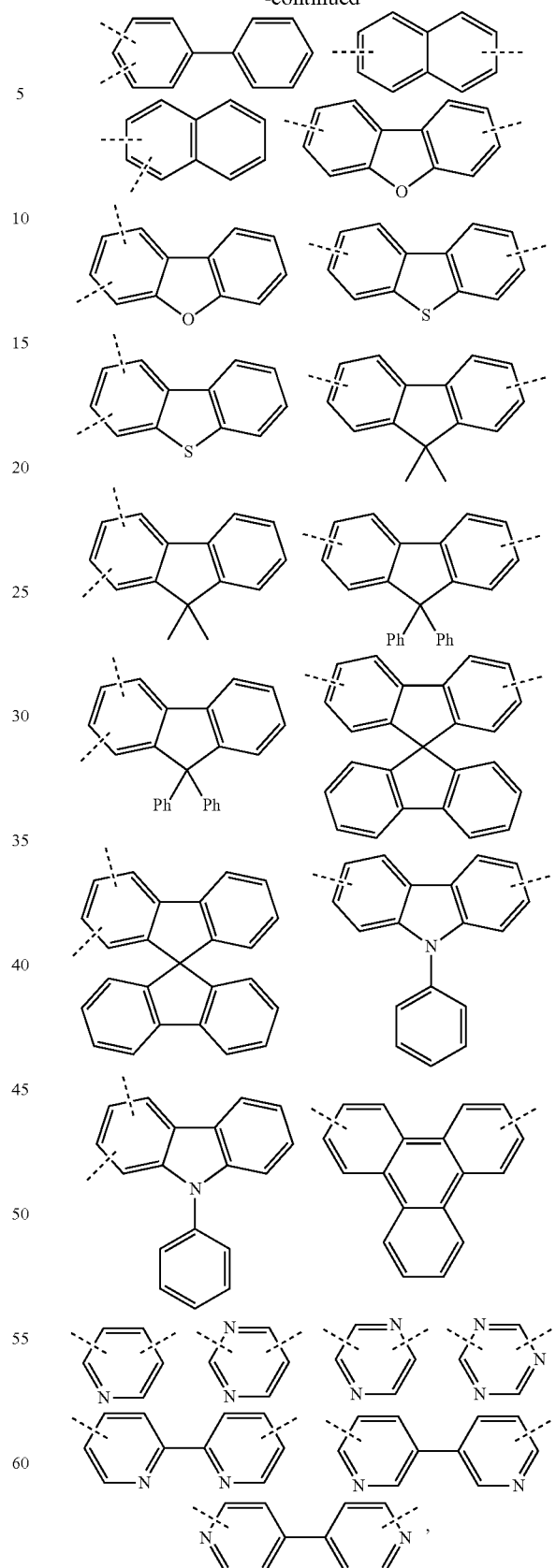

and combinations thereof.

According to an embodiment of the present invention, $L_1$, $L_2$ and $L_3$ are each independently selected from single bond or phenylene.
According to an preferred embodiment of the present invention, wherein the compound is selected from the group consisting of:
Compound 1
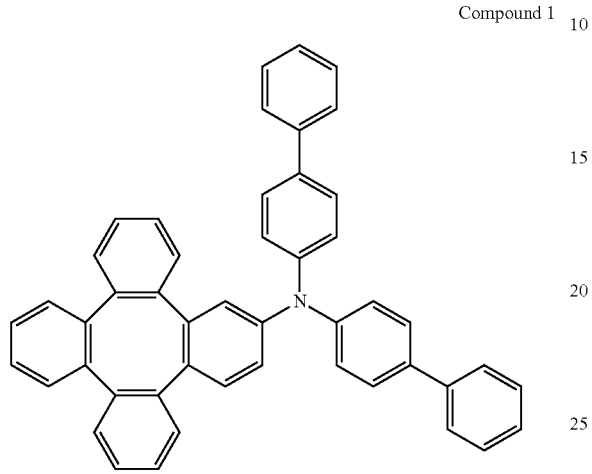
Compound 2
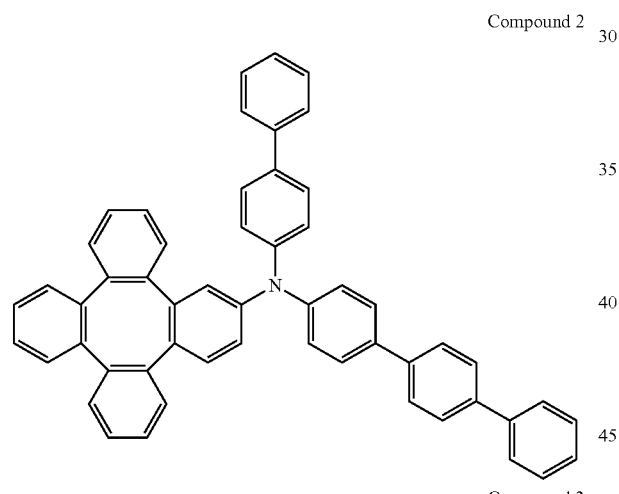
Compound 3
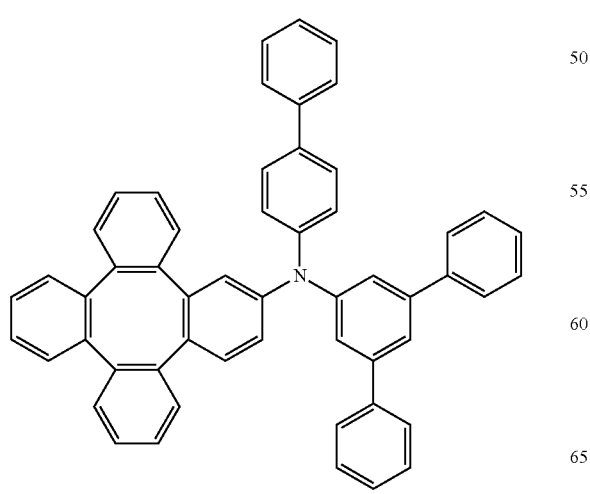
-continued
Compound 4
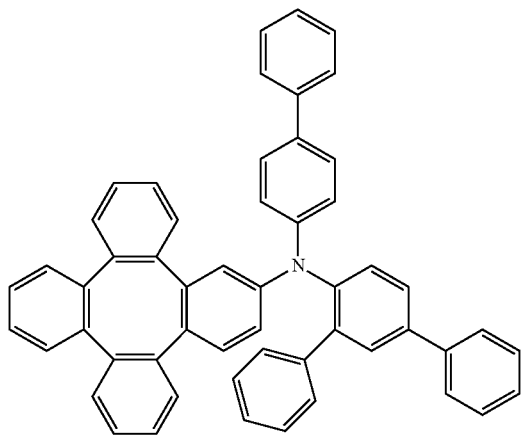
Compound 5
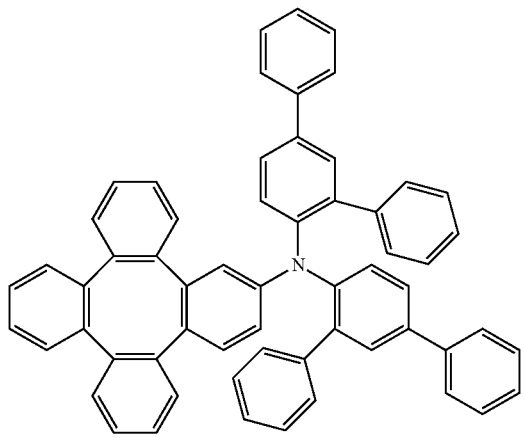
Compound 6
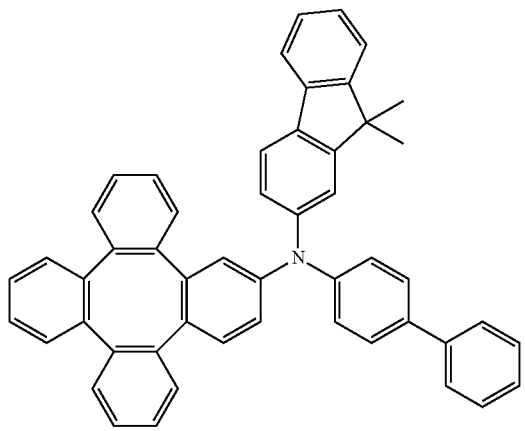

Compound 7
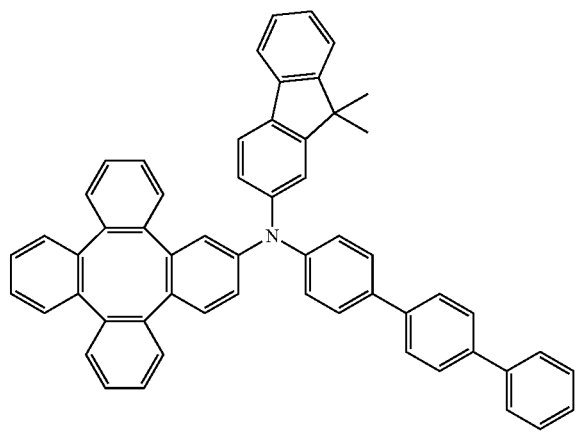
Compound 8
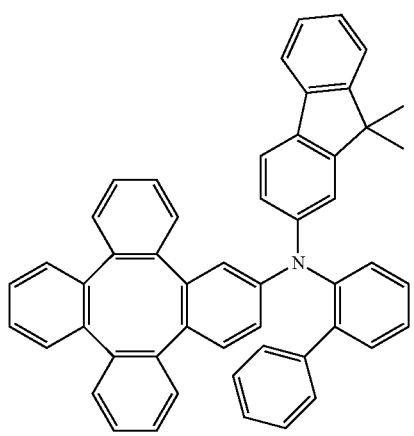
Compound 9
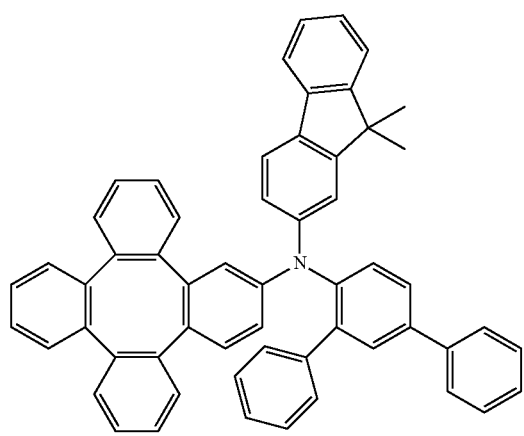
Compound 10
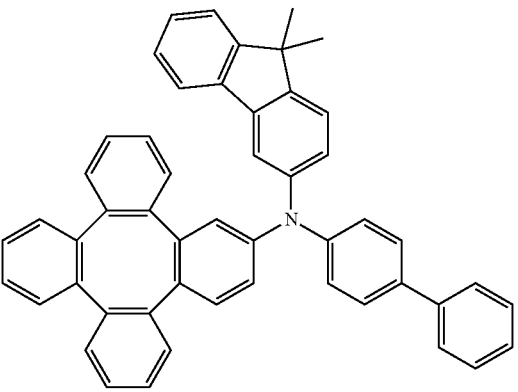
Compound 11
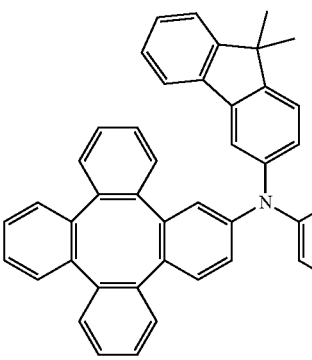
Compound 12
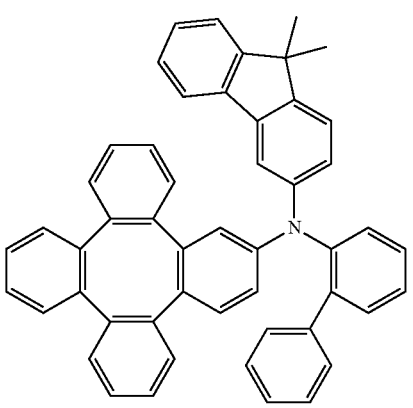
Compound 13
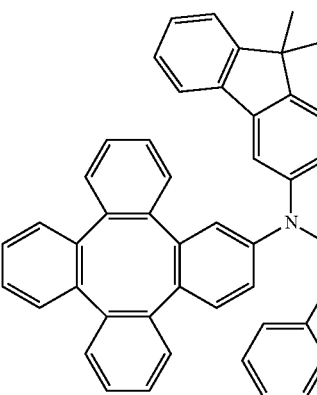

Compound 14
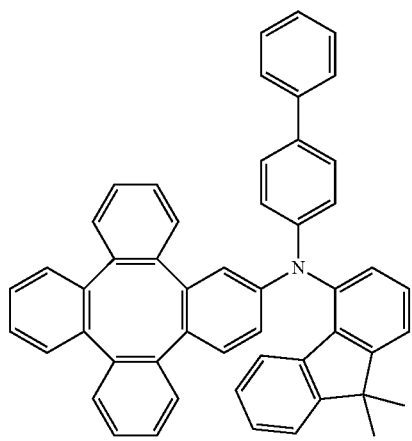
Compound 15
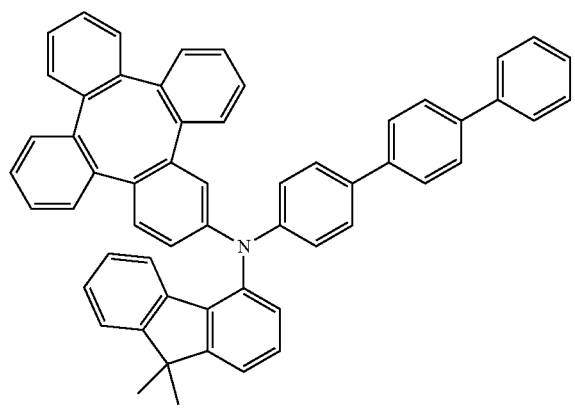
Compound 16
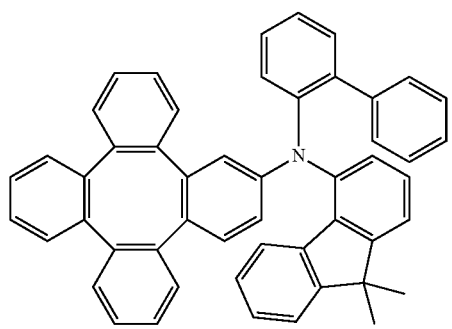
Compound 17
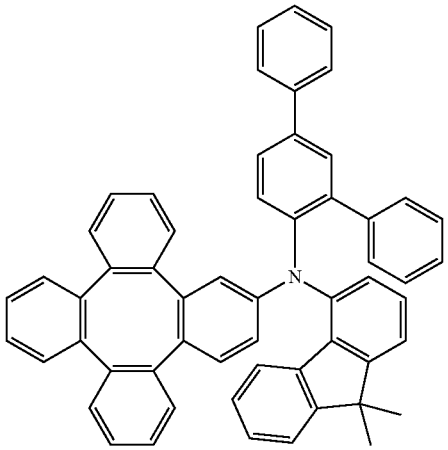
Compound 18
Compound 19
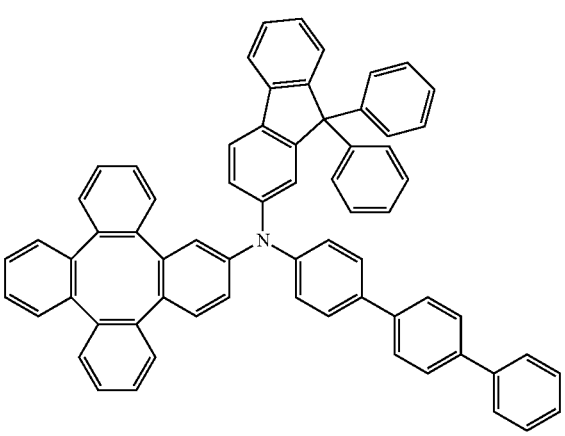

Compound 20
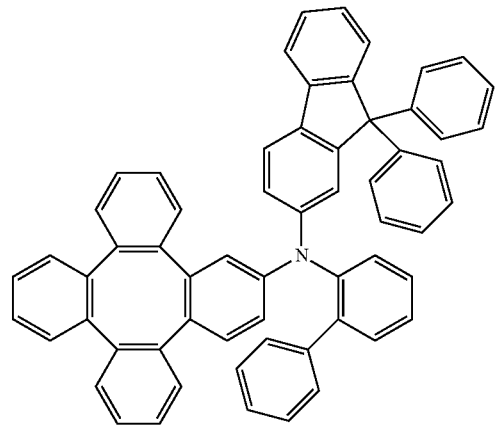
Compound 21
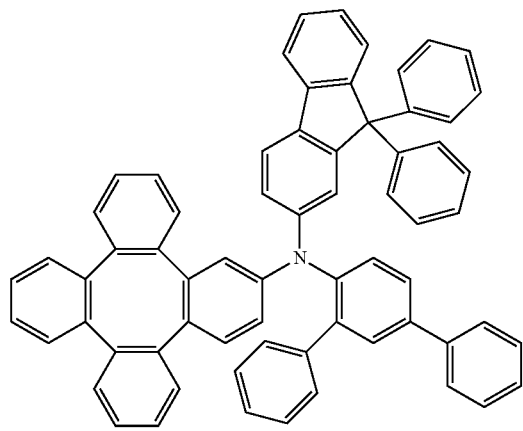
Compound 22
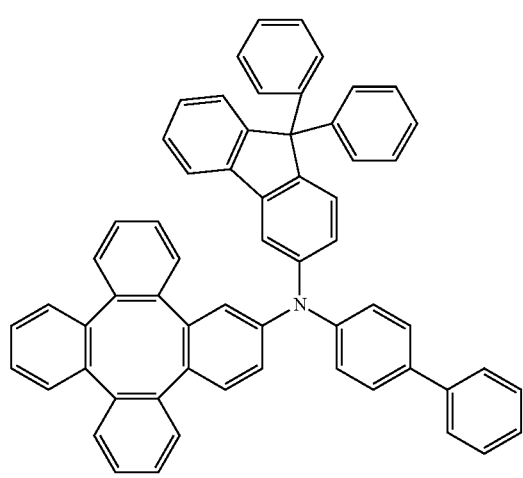
Compound 23
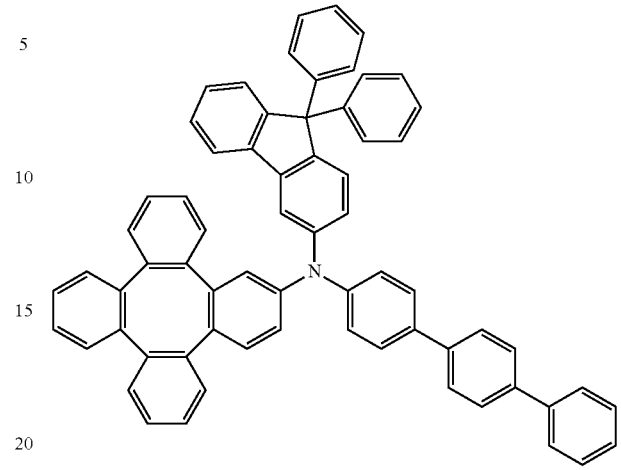
Compound 24
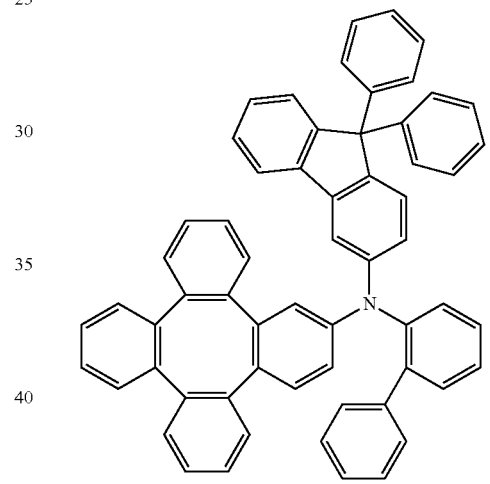
Compound 25
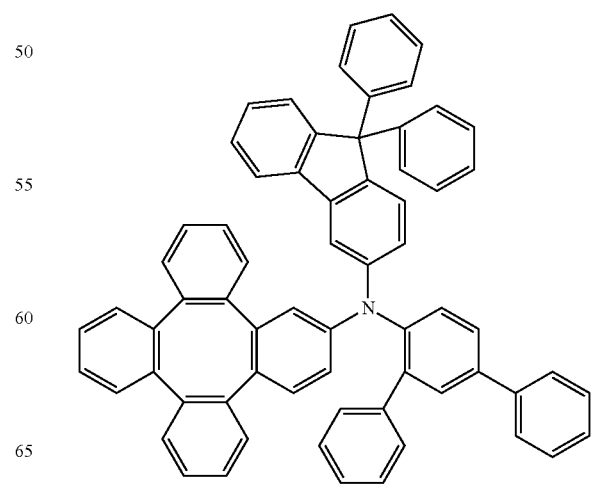

Compound 26
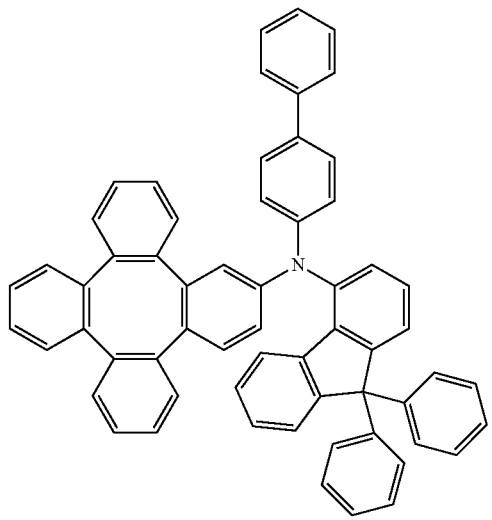
Compound 27
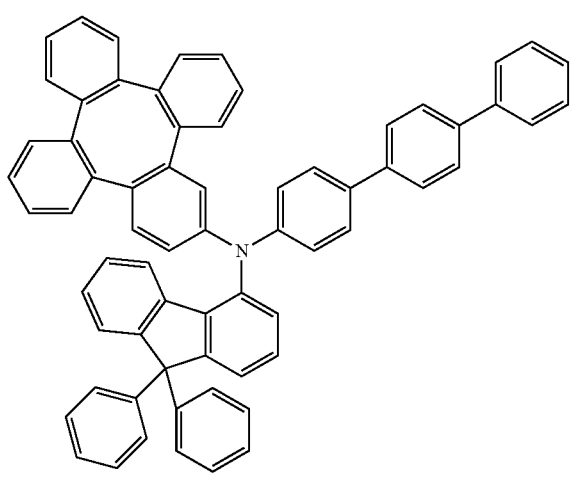
Compound 28
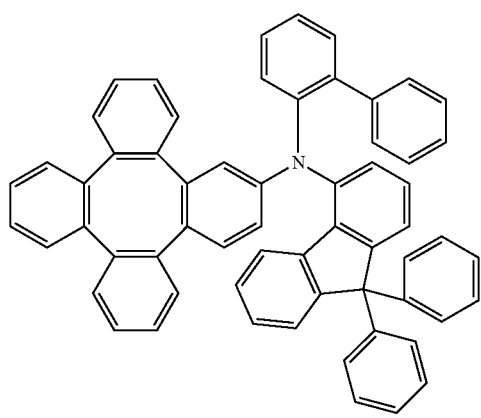
Compound 29
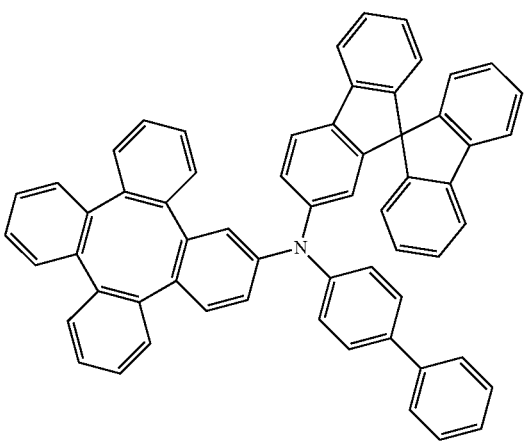
Compound 30
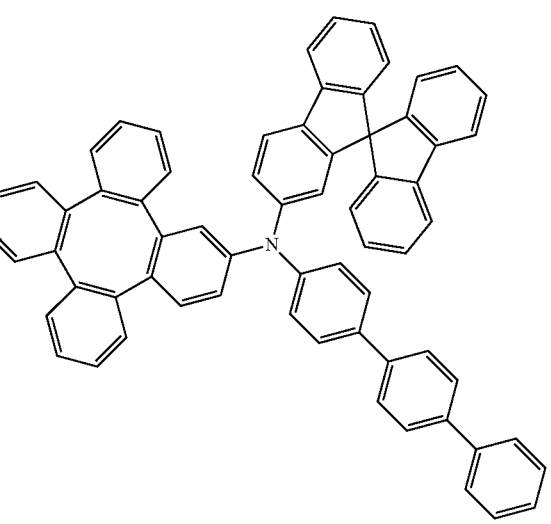
Compound 31

Compound 32
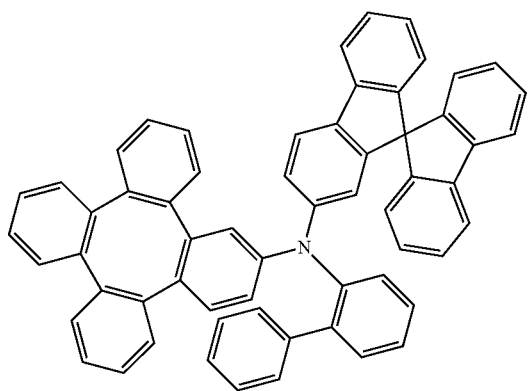
Compound 33
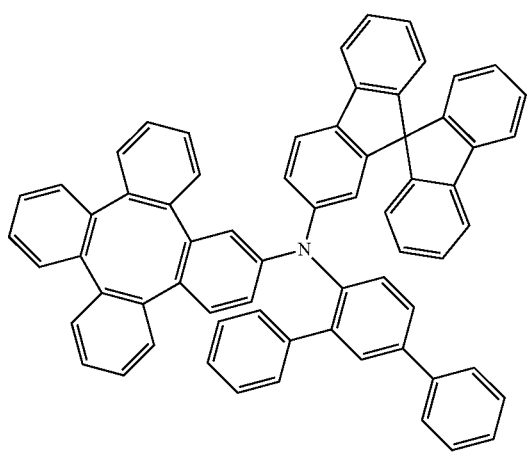
Compound 34
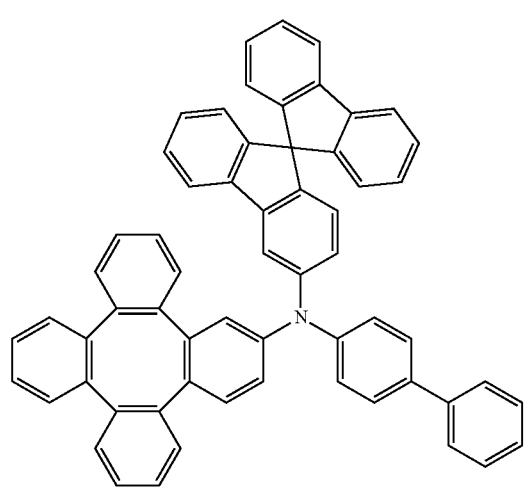
Compound 35
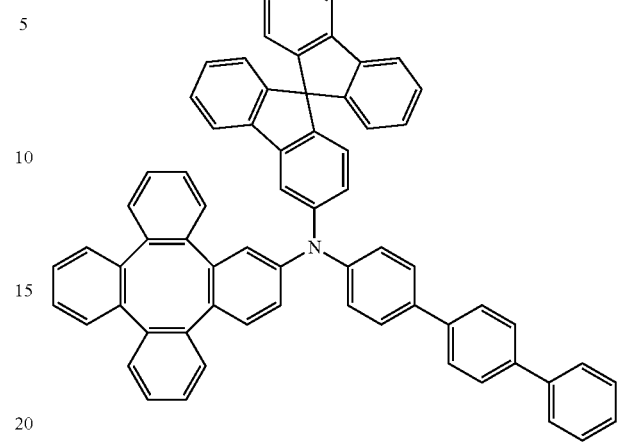
Compound 36
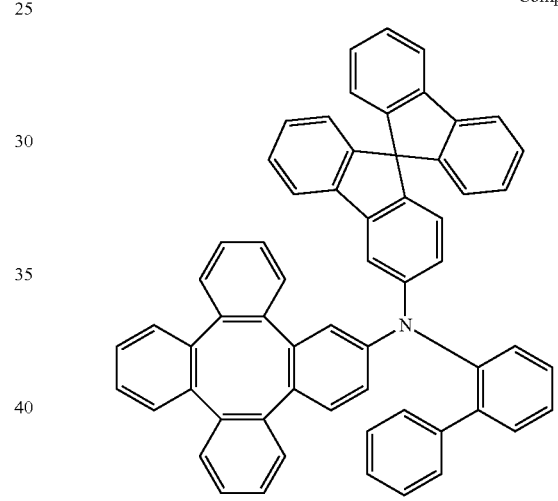
Compound 37
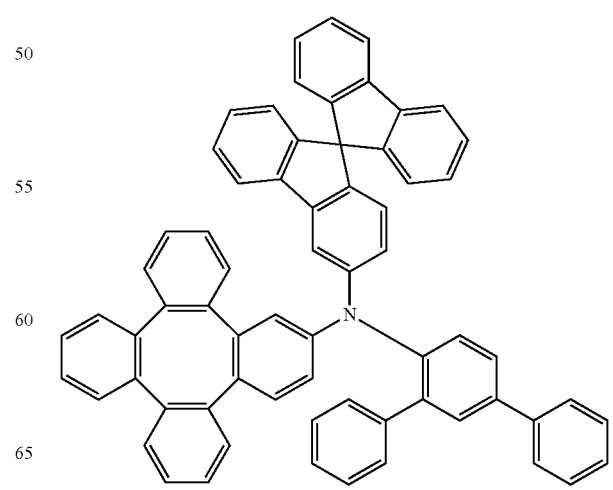

Compound 38
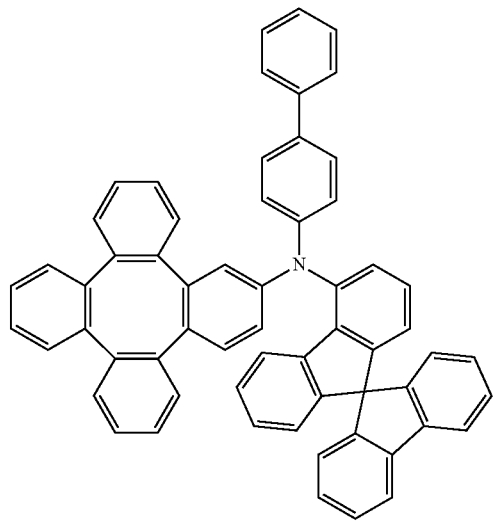
Compound 39
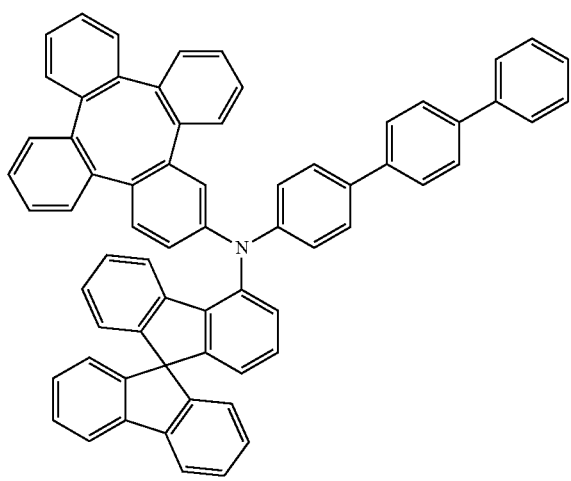
Compound 40
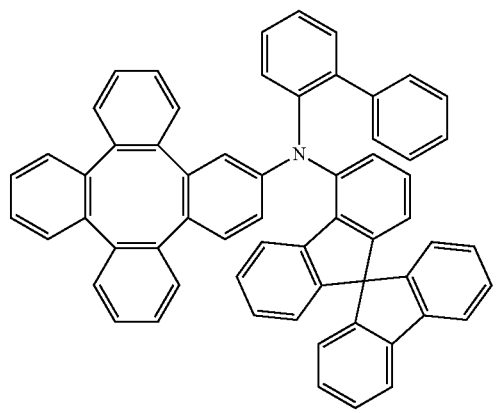
Compound 41
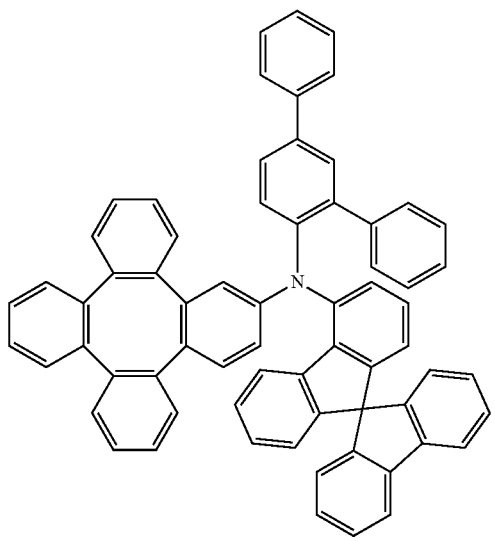
Compound 42
Compound 43
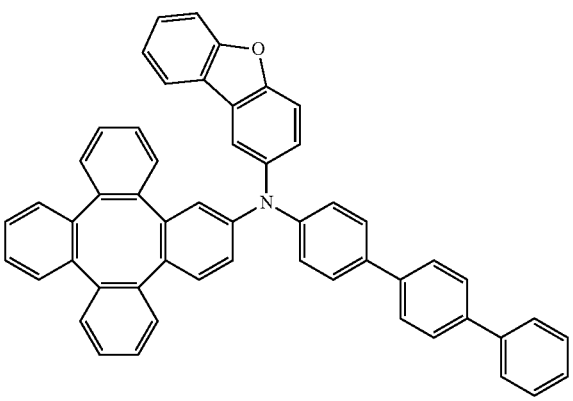

Compound 44
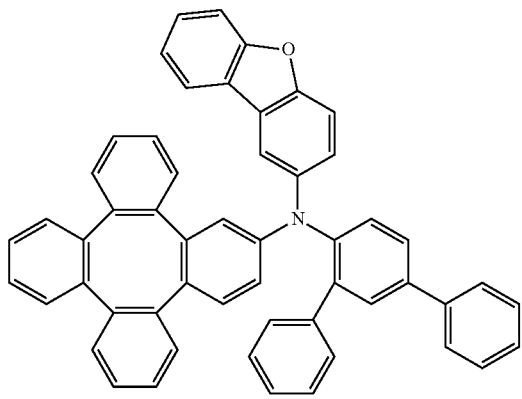
Compound 45
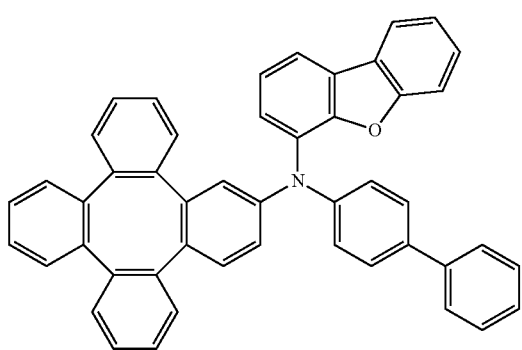
Compound 46
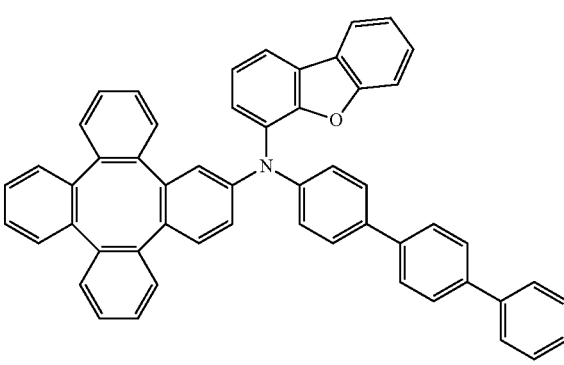
Compound 47
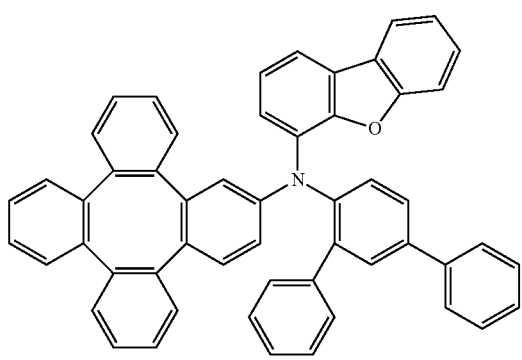
Compound 48
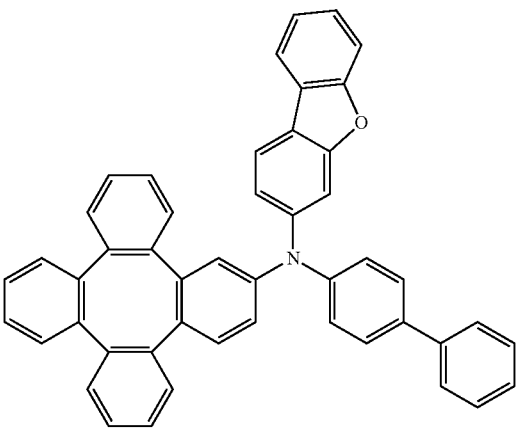
Compound 49
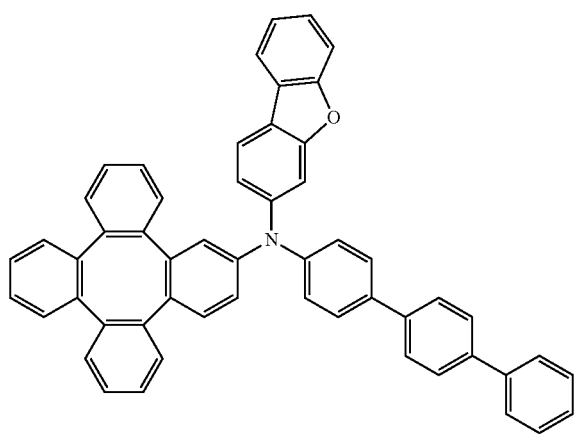
Compound 50
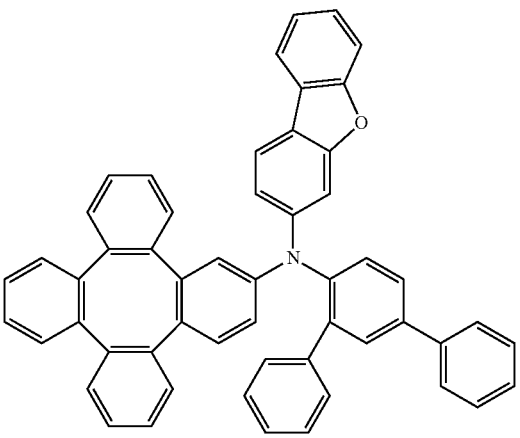

Compound 51
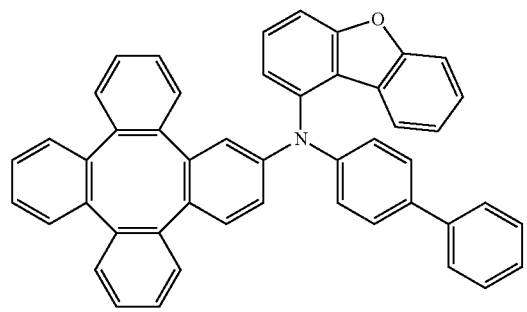
Compound 52
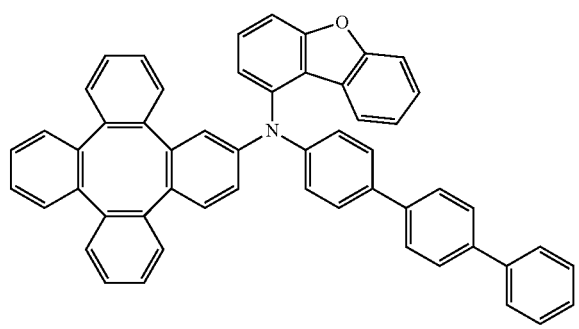
Compound 53
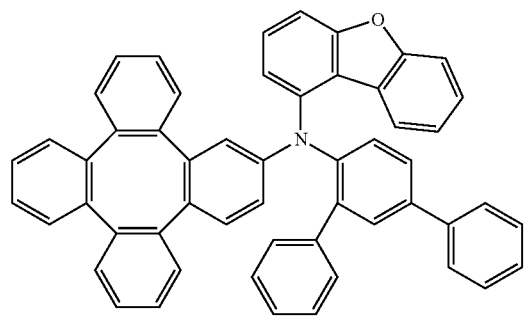
Compound 54
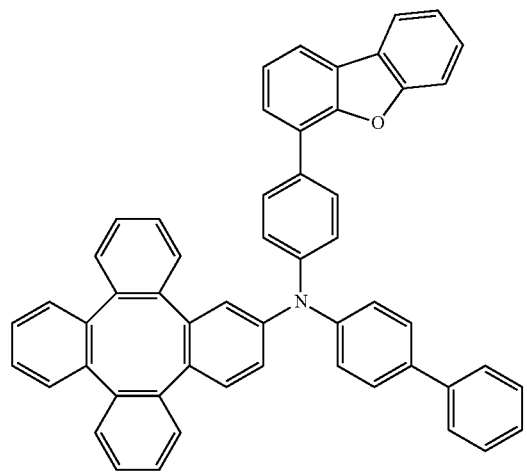
Compound 55
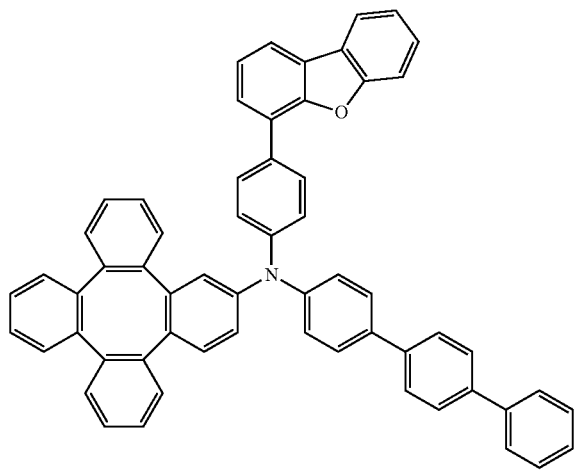
Compound 56
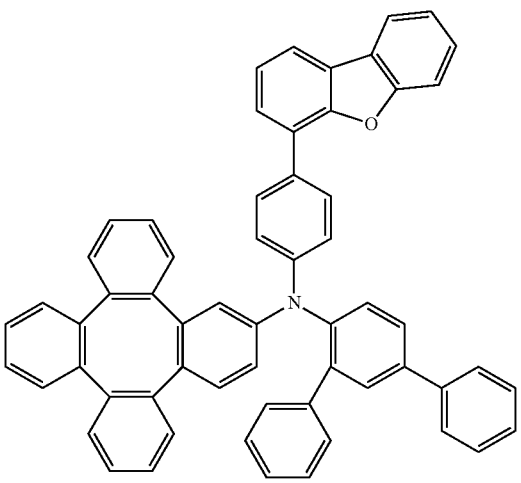
Compound 57
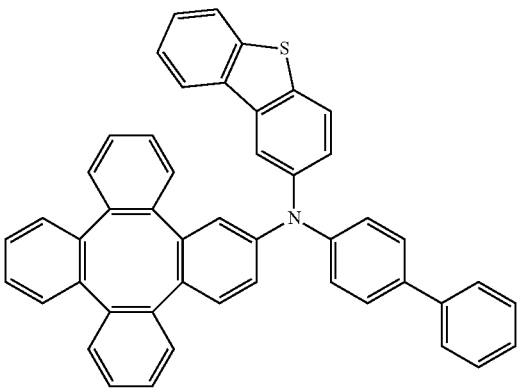

Compound 58
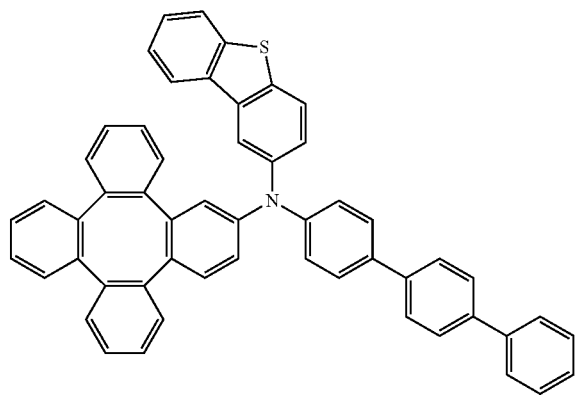
Compound 59
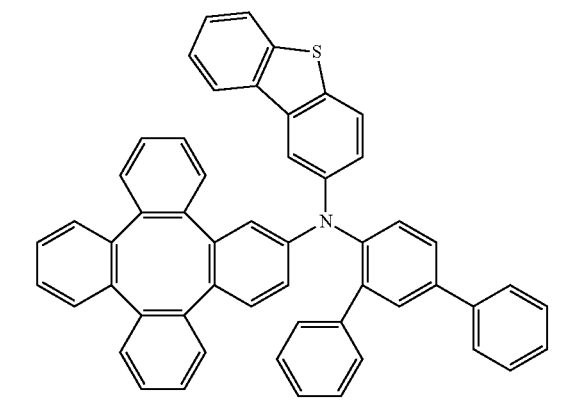
Compound 60
Compound 61
Compound 62
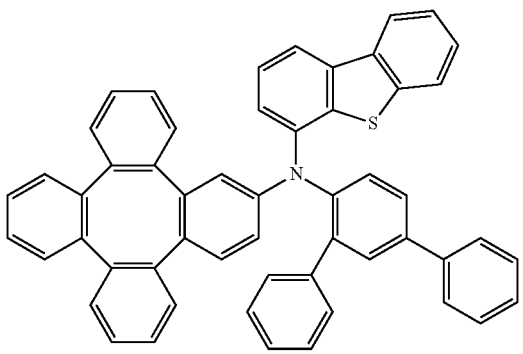
Compound 63
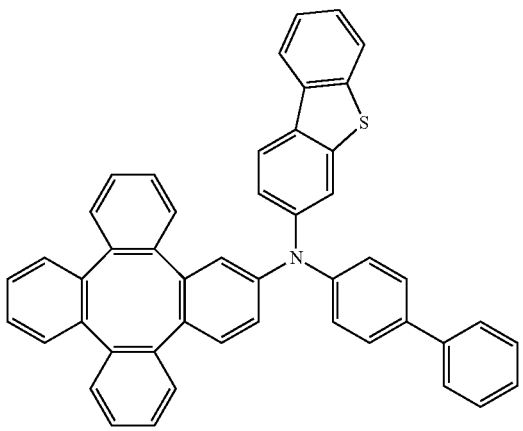
Compound 64
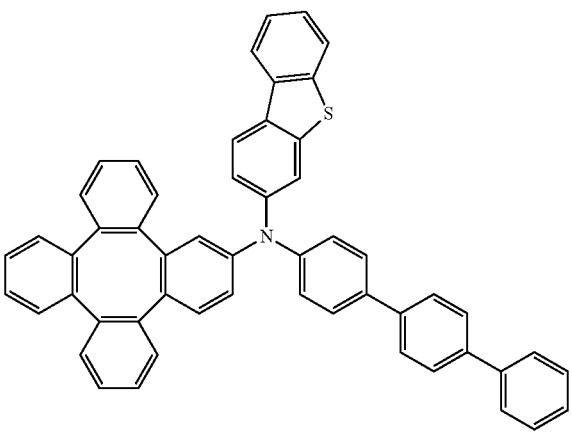

-continued
Compound 65
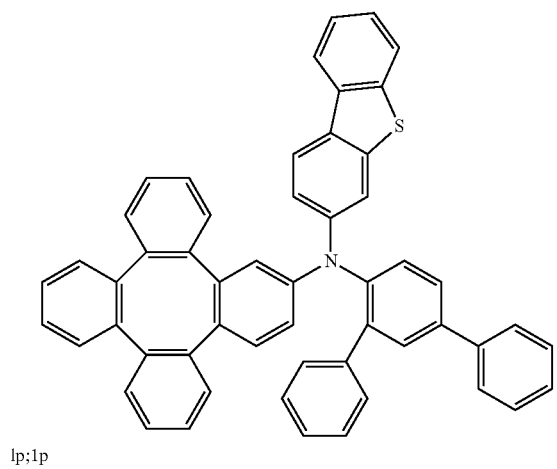
lp;1p
Compound 66
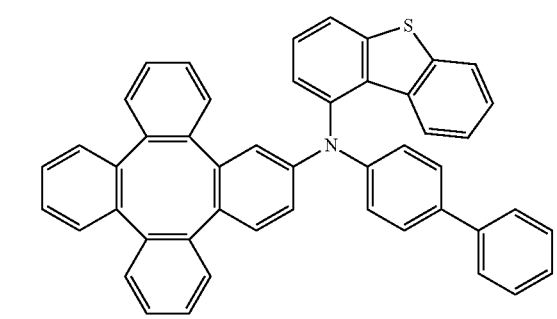
Compound 67
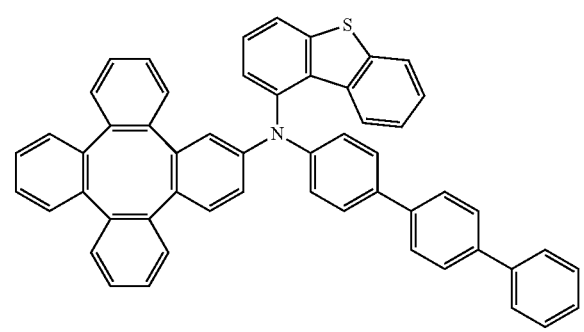
Compound 68
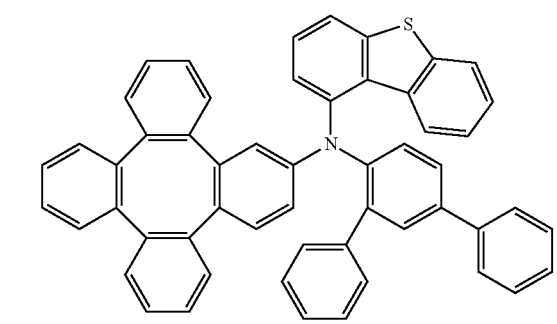
-continued
Compound 69
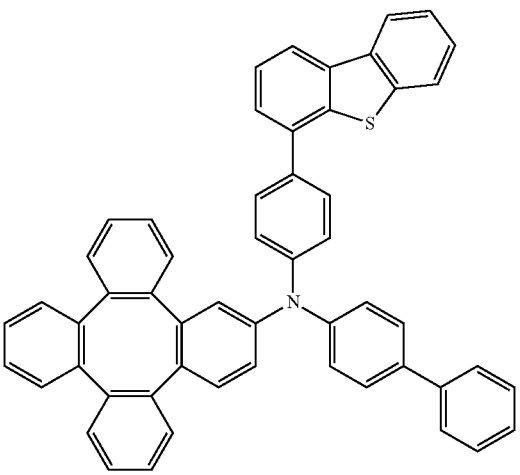
Compound 70
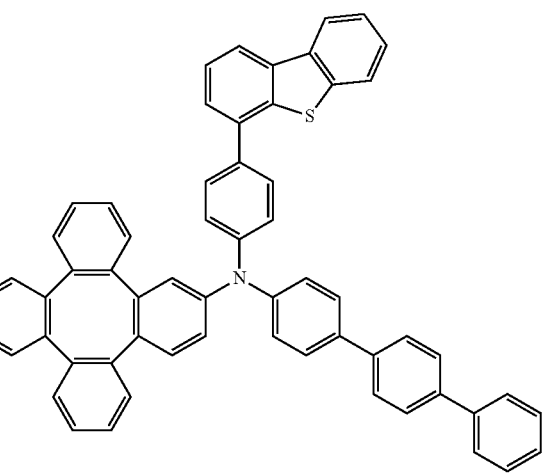
Compound 71
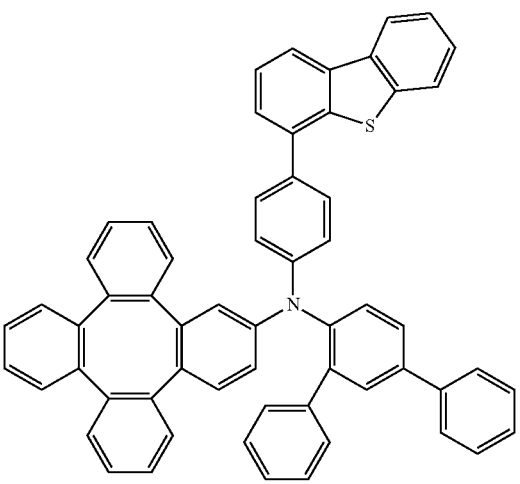

Compound 72
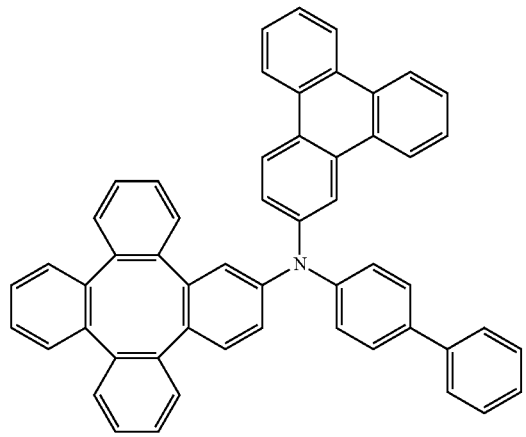
Compound 73
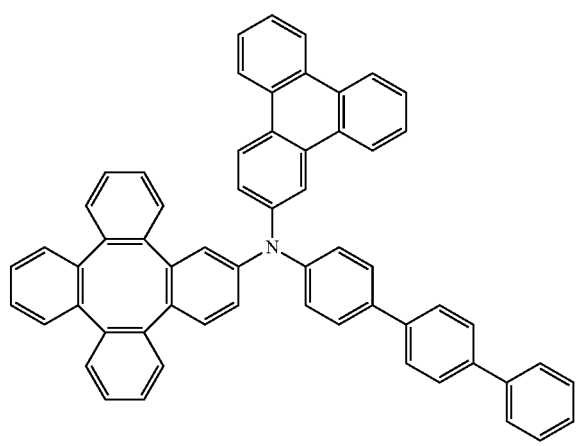
Compound 74
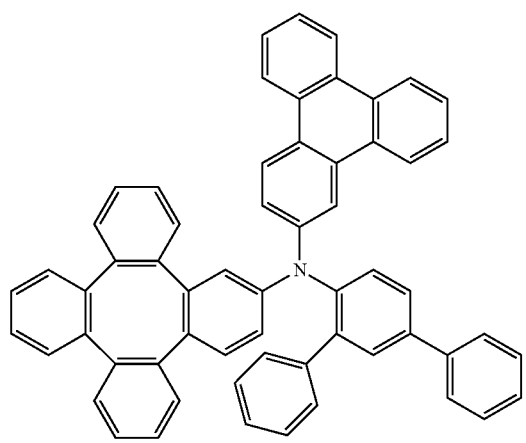
Compound 75
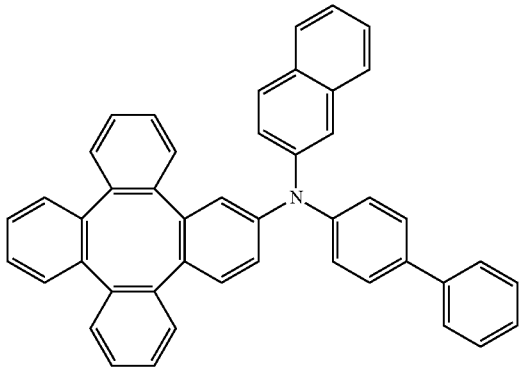
Compound 76
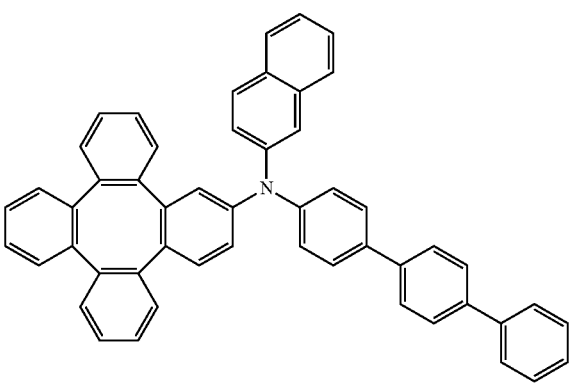
Compound 77
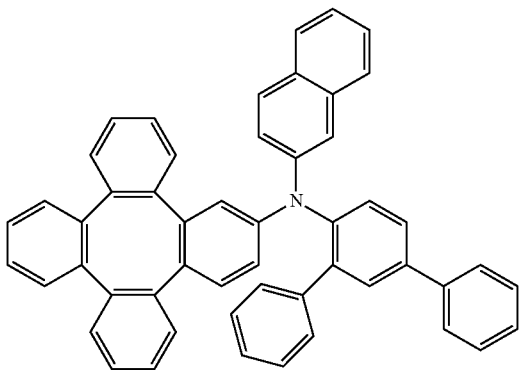
Compound 78
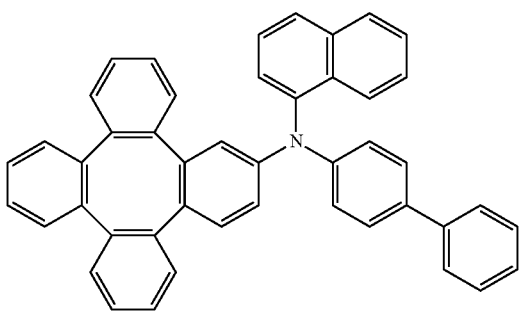

-continued
Compound 79
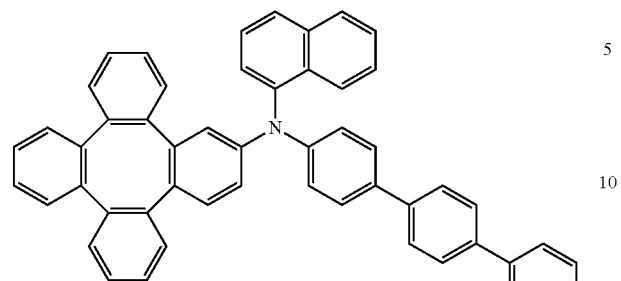
Compound 80
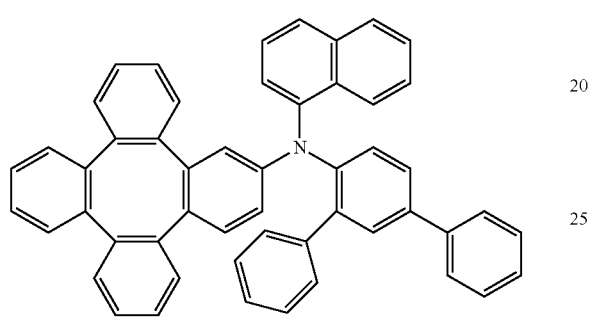
Compound 81
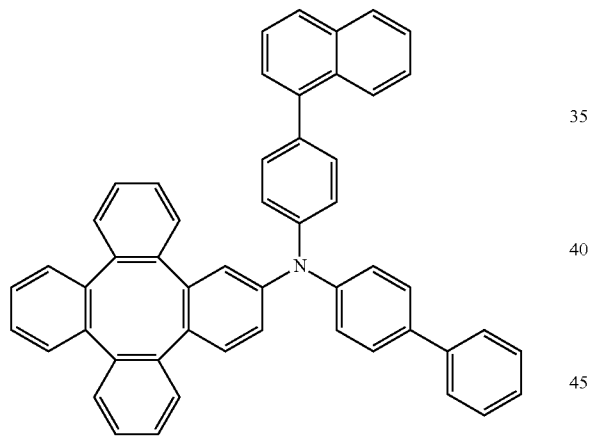
Compound 82
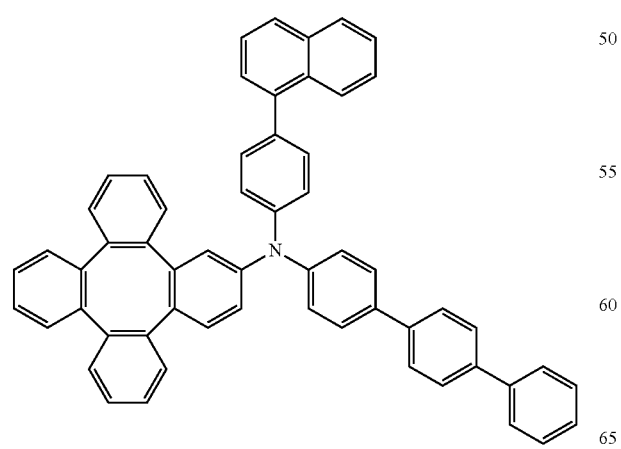
Compound 83
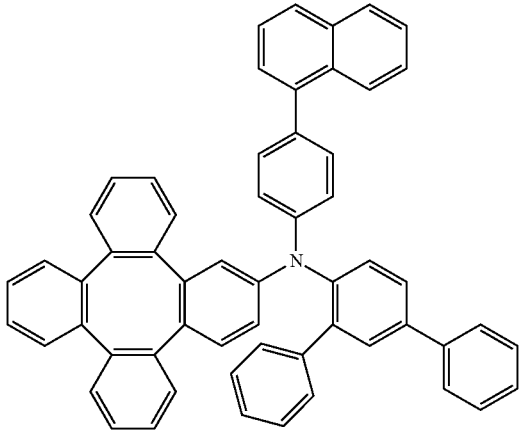
Compound 84
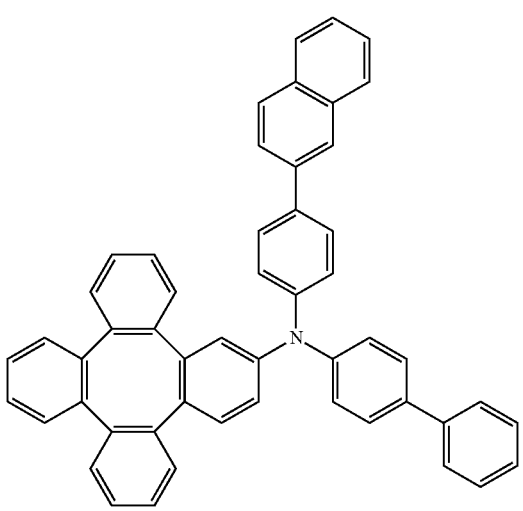
Compound 85
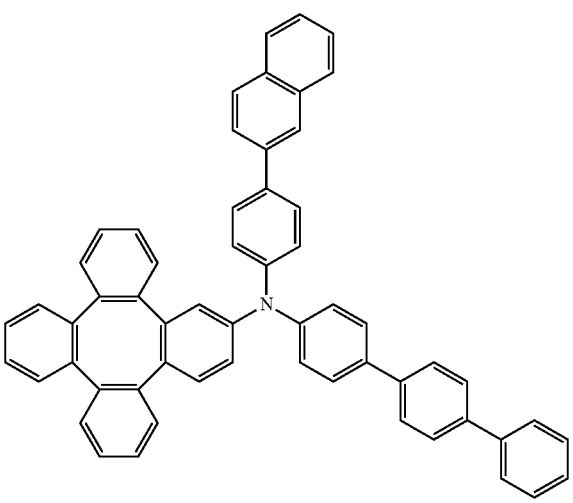

Compound 86
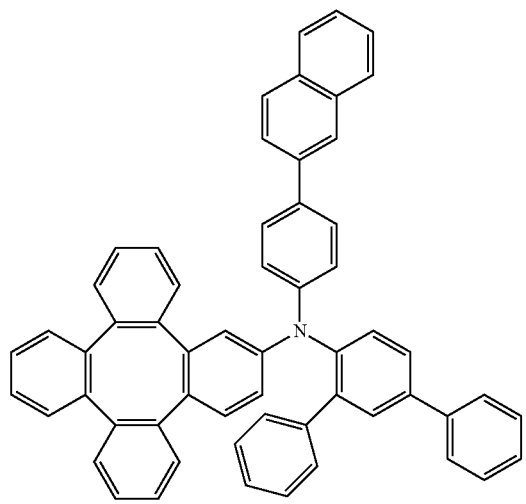
Compound 87
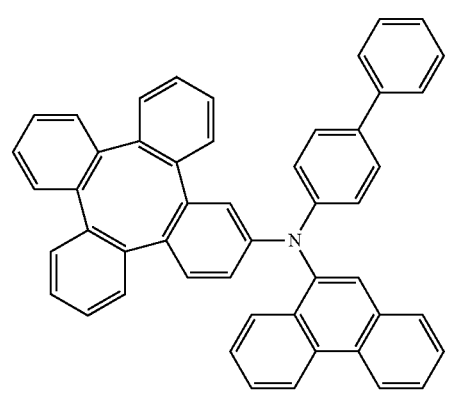
Compound 88
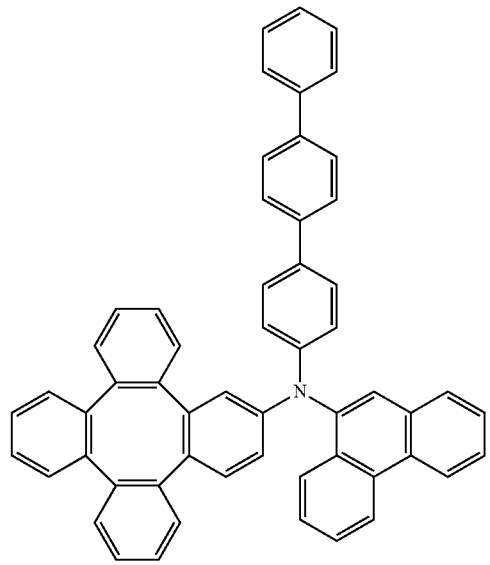
Compound 89
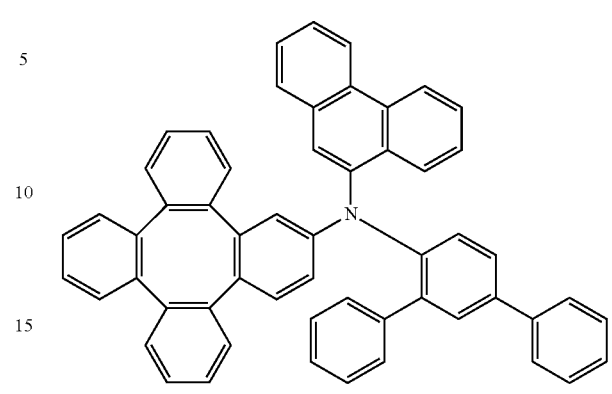
Compound 90
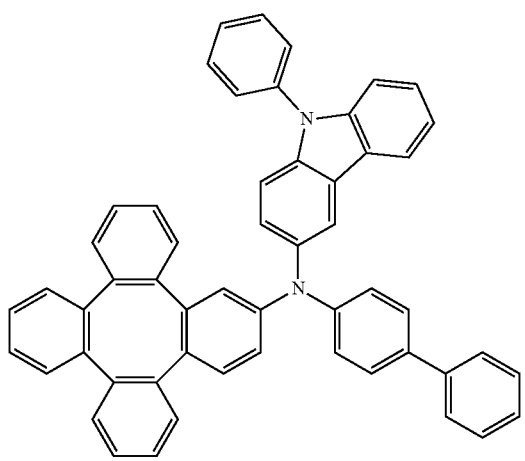
Compound 91
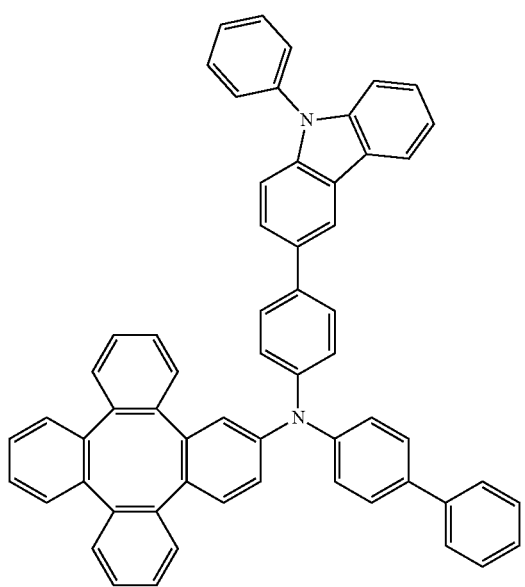

Compound 92
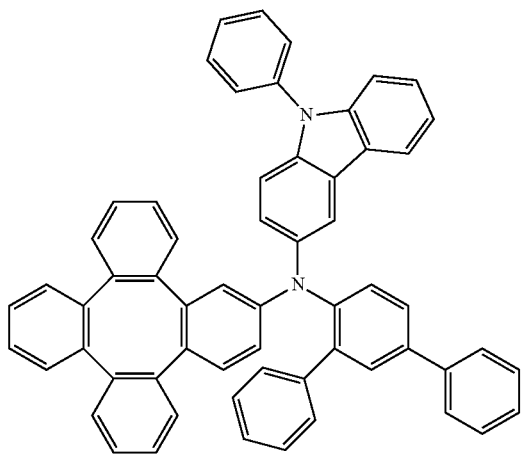
Compound 95
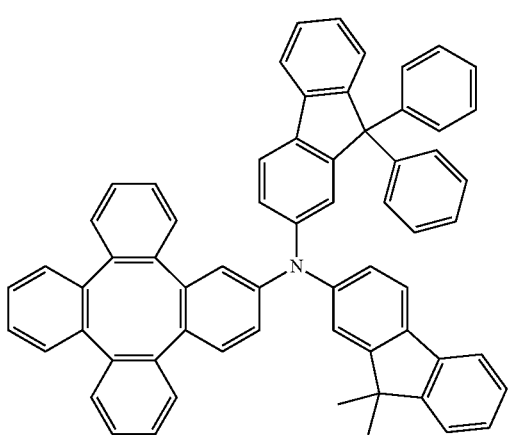
Compound 93
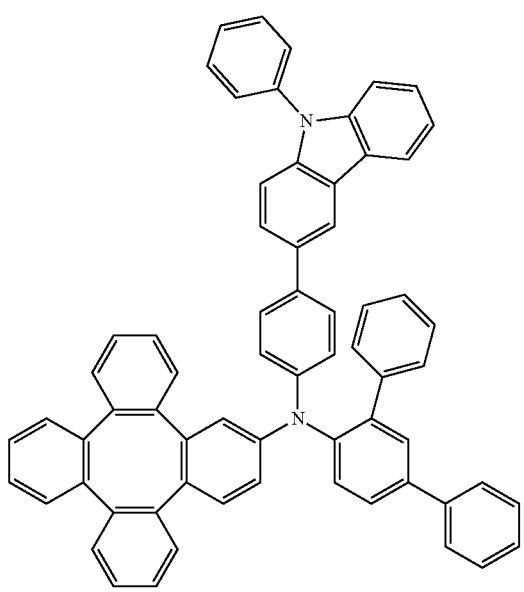
Compound 96
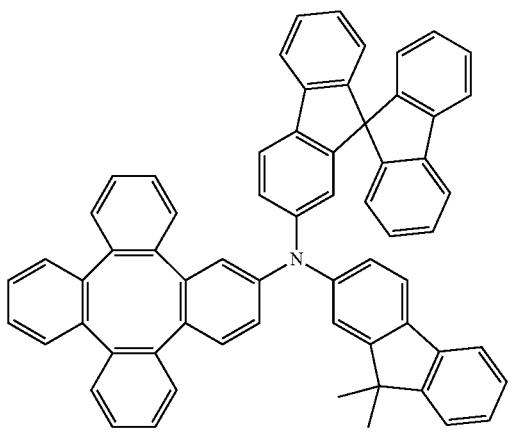
Compound 94
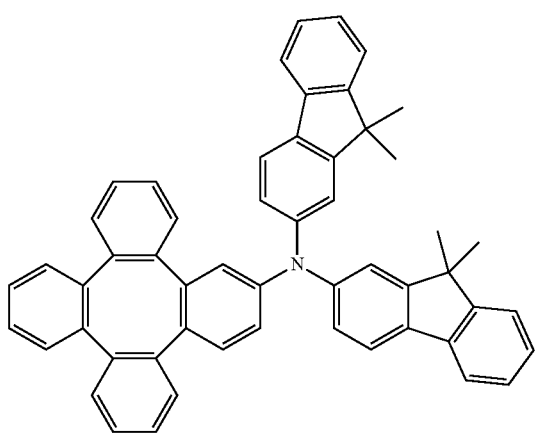
Compound 97
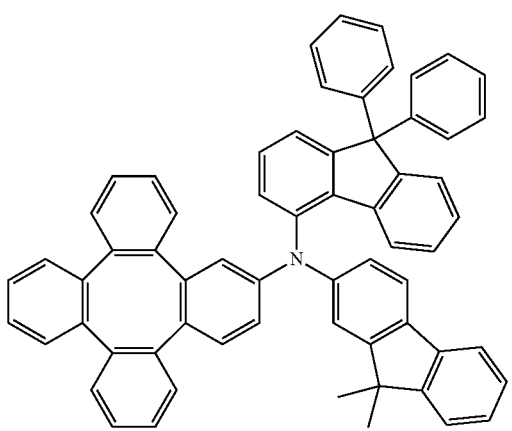

Compound 98
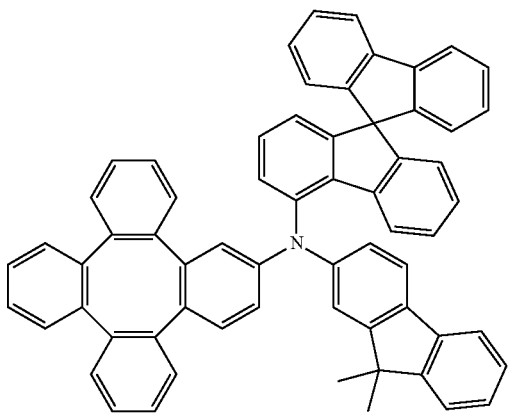
Compound 99
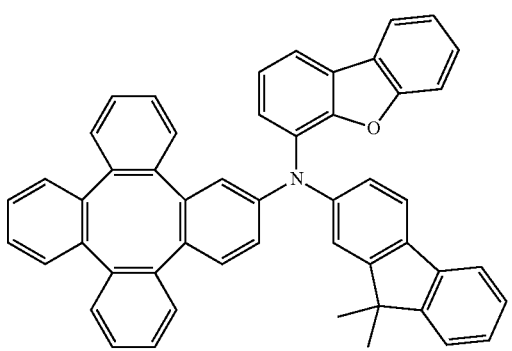
Compound 100
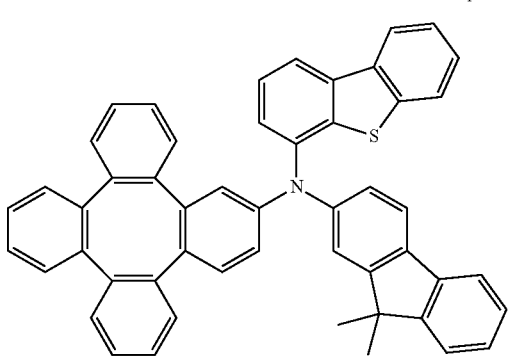
Compound 101
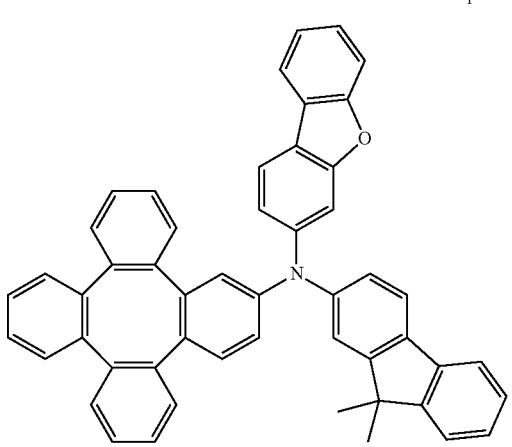
Compound 102
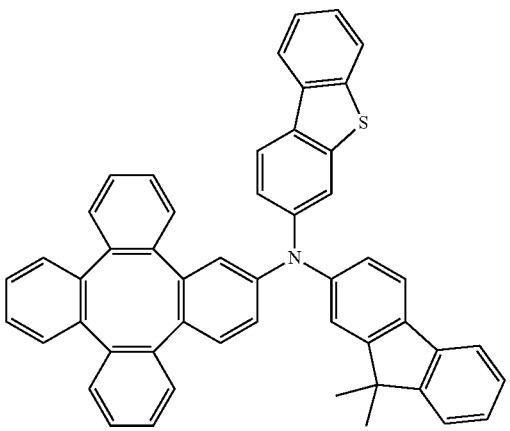
Compound 103
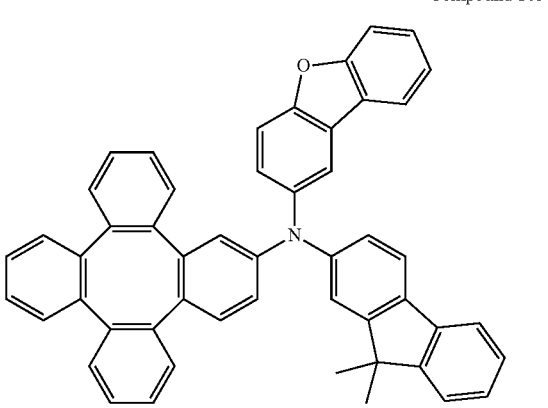
Compound 104
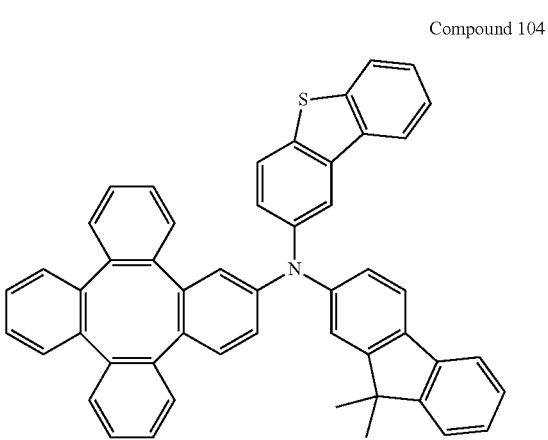

Compound 105
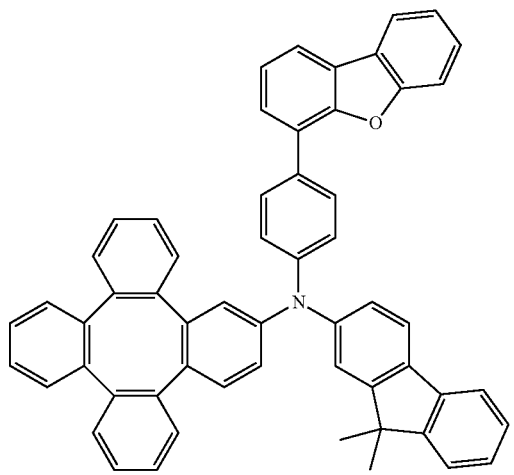
Compound 106
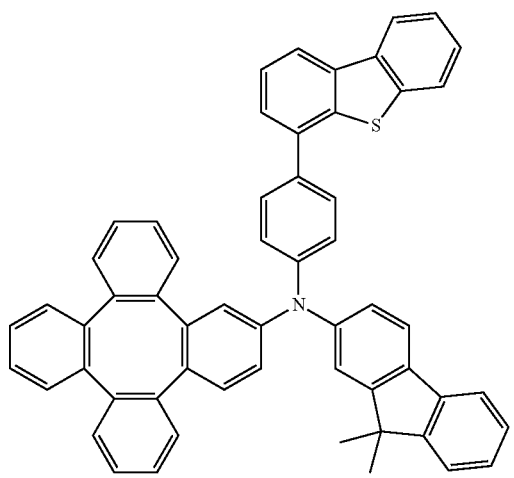
Compound 107
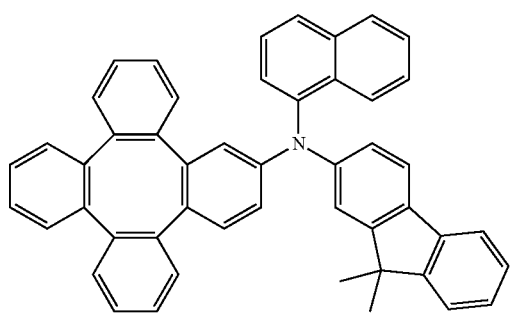
Compound 108
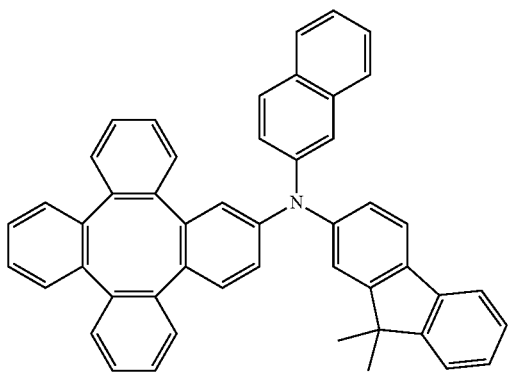
Compound 109
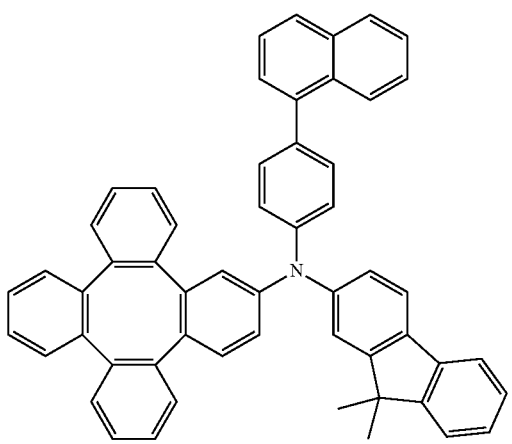
Compound 110
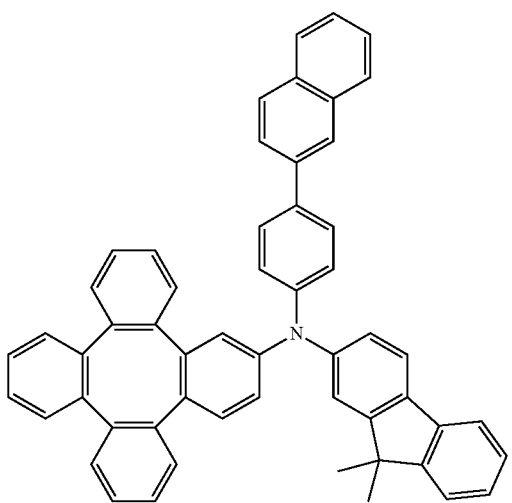

-continued
Compound 111
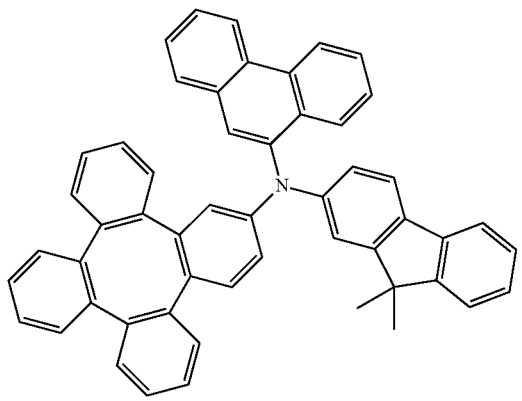
Compound 112
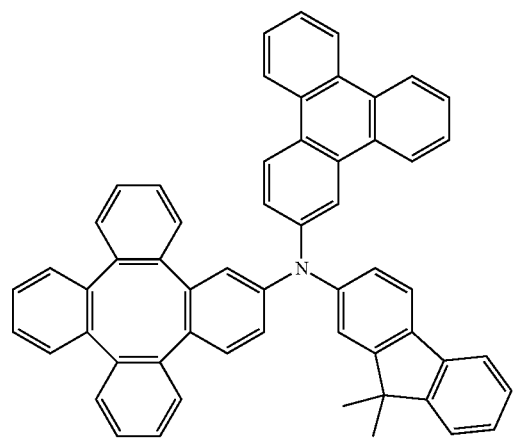
Compound 113
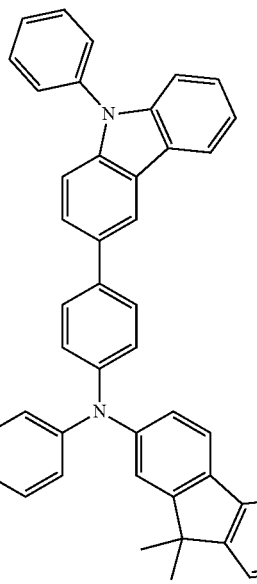
Compound 114
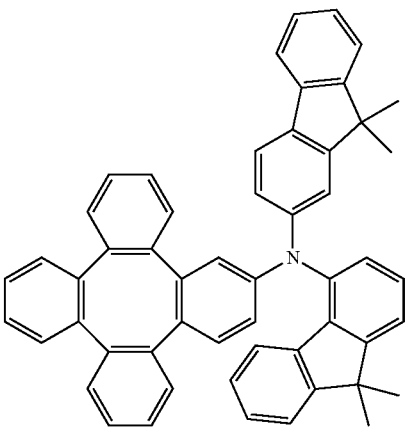
Compound 115
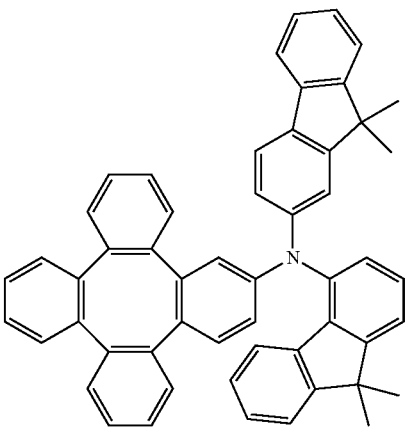
Compound 116
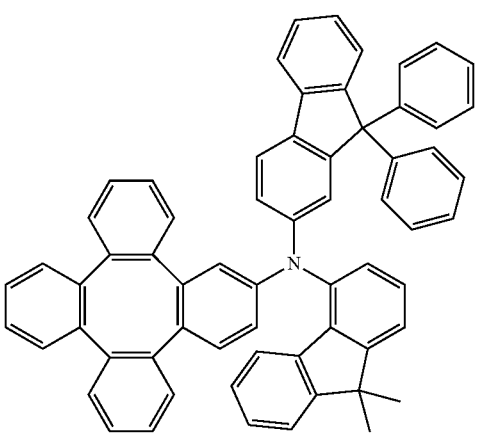

Compound 117
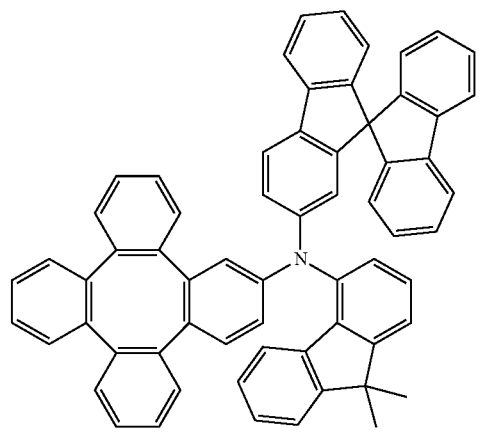
Compound 118
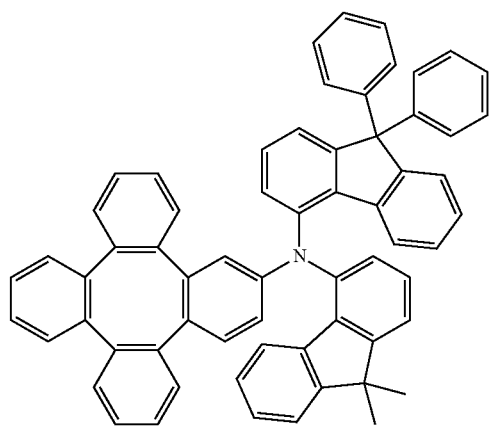
Compound 119
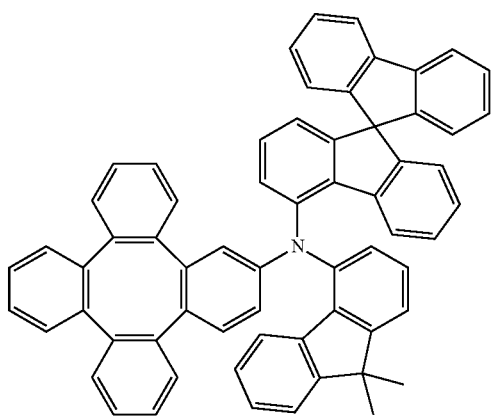
Compound 120
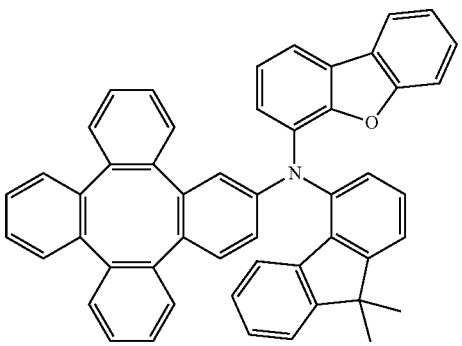
Compound 121
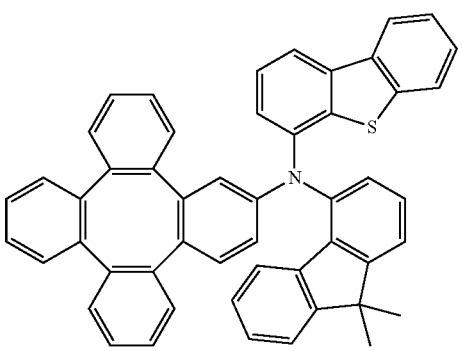
Compound 122
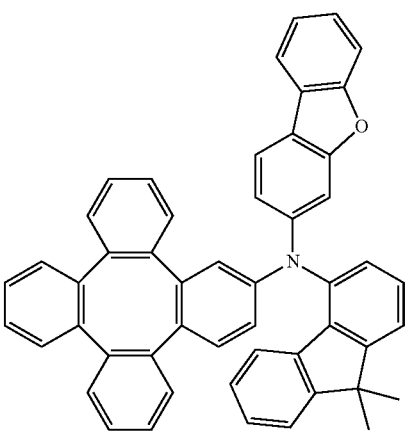
Compound 123
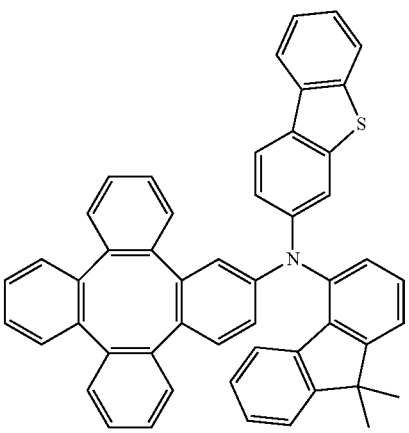

Compound 124
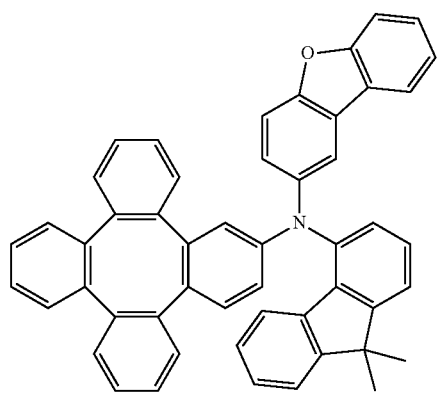
Compound 125
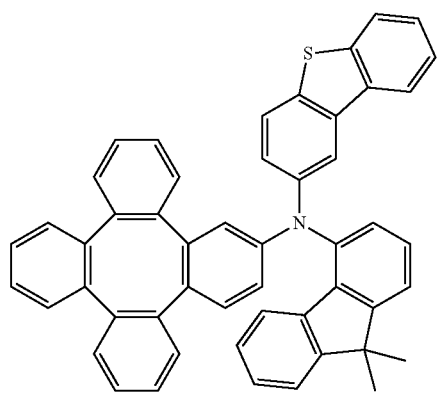
Compound 126
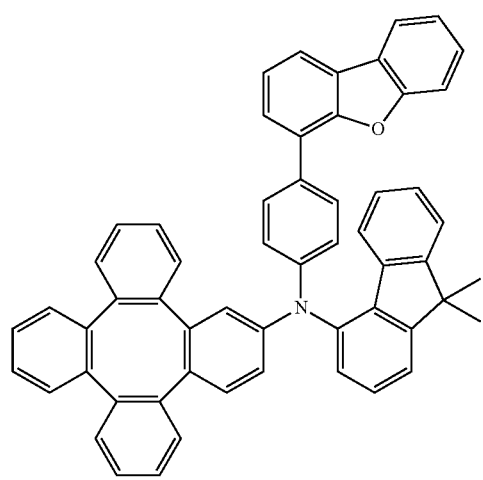
Compound 127
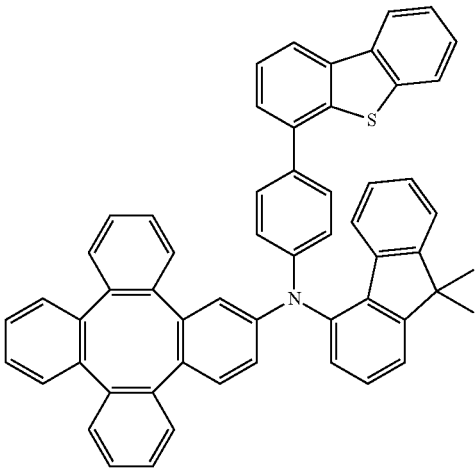
Compound 128
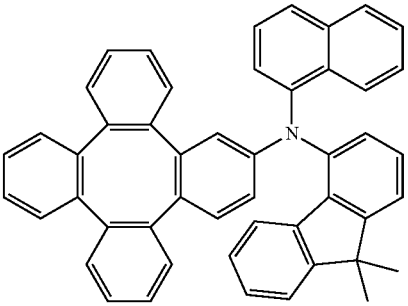
Compound 129
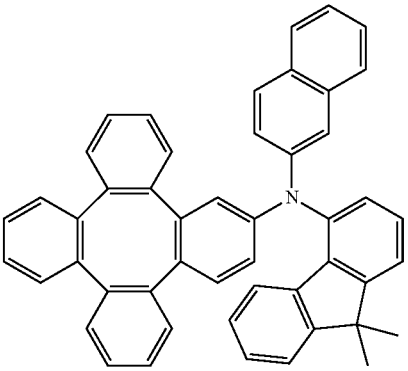
Compound 130
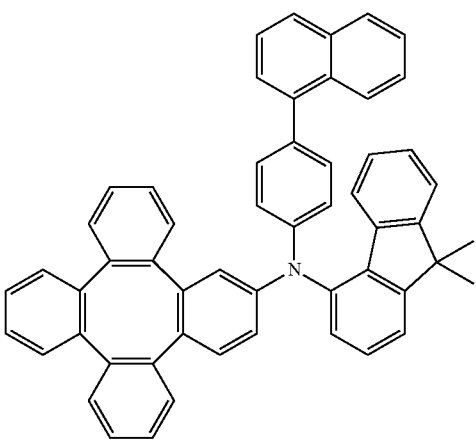

Compound 131
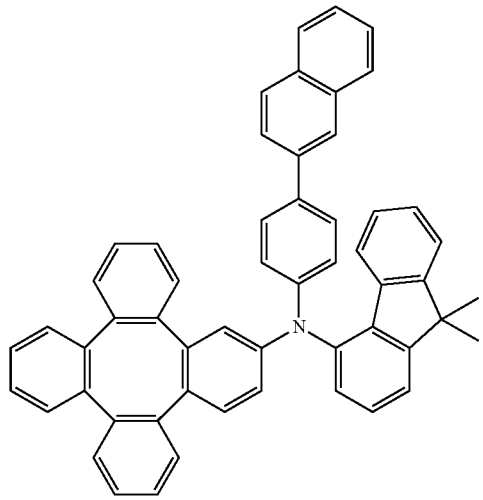
Compound 132
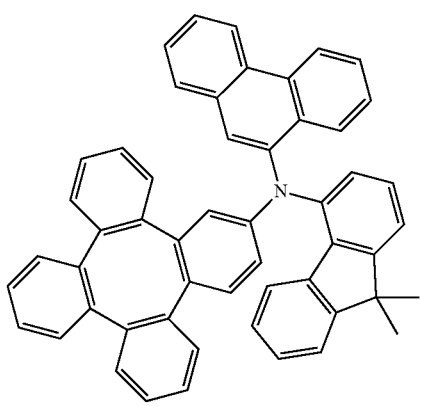
Compound 133
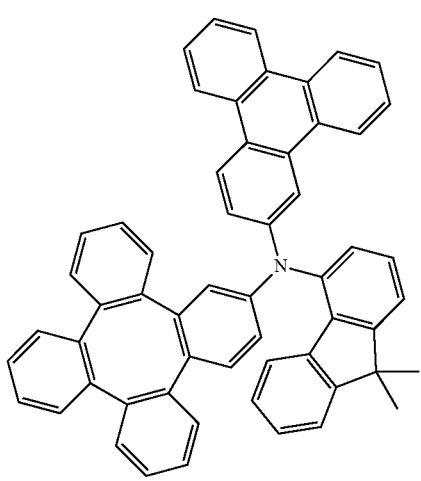
Compound 134
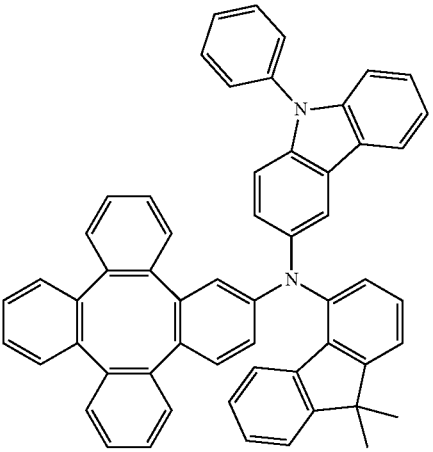
Compound 135
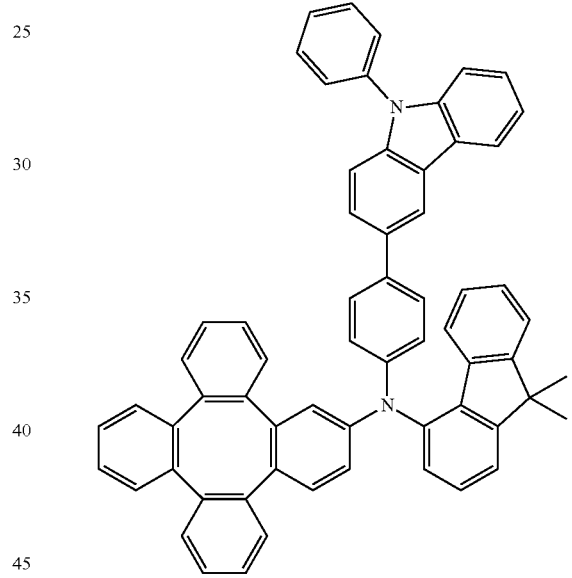
Compound 136
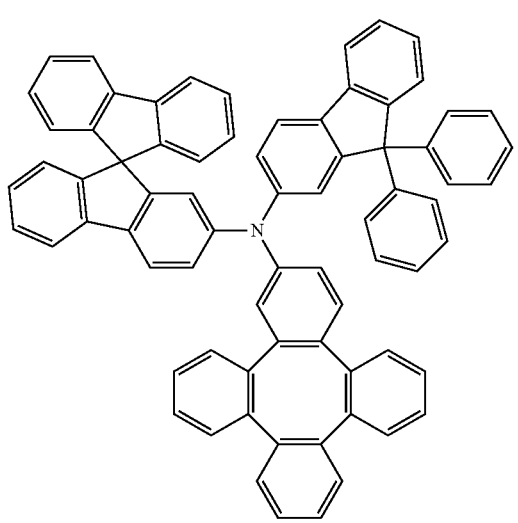

Compound 137
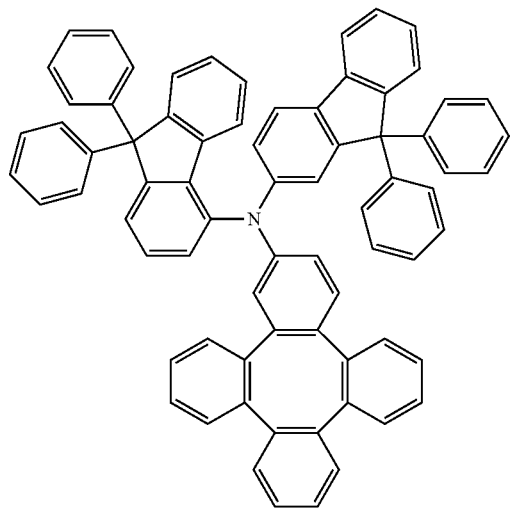
Compound 140
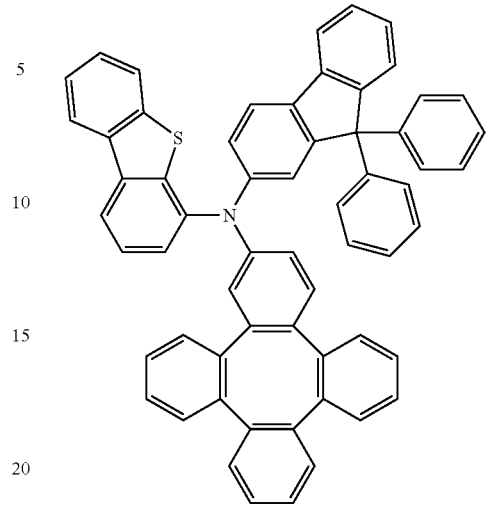
Compound 138
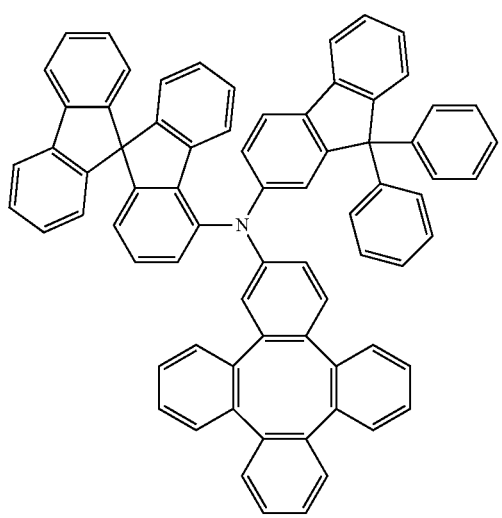
Compound 141
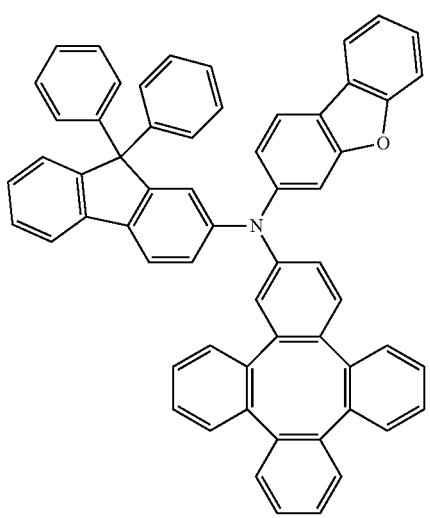
Compound 139
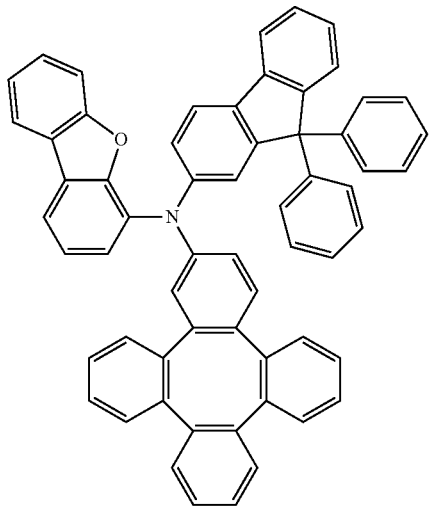
Compound 142
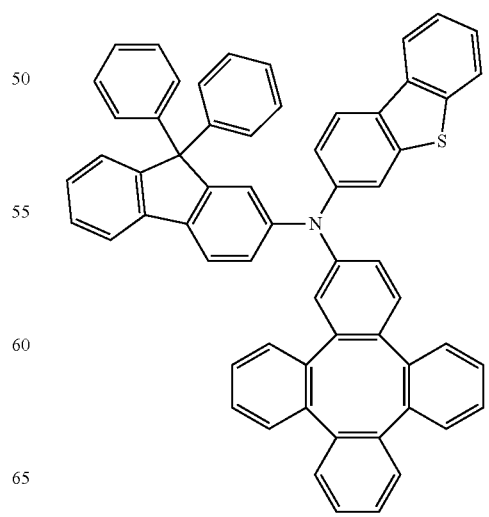

Compound 143
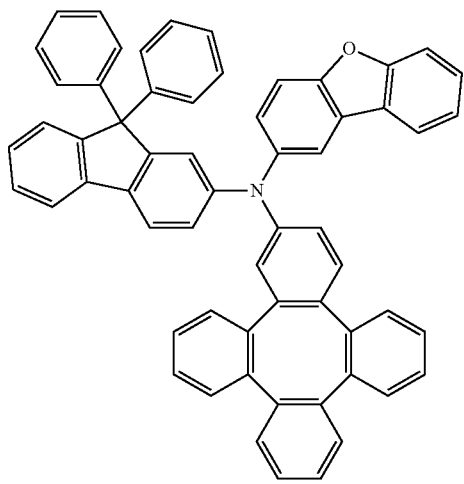
Compound 144
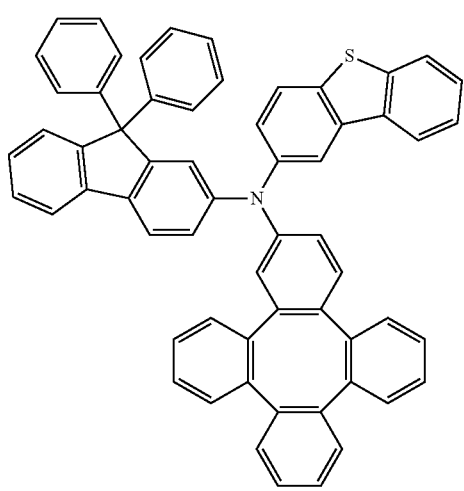
Compound 145
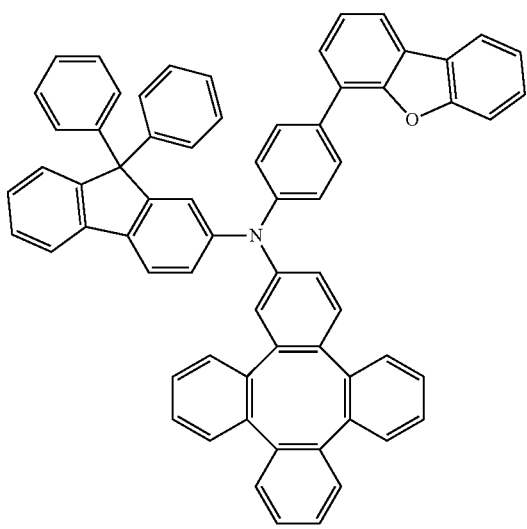
Compound 146
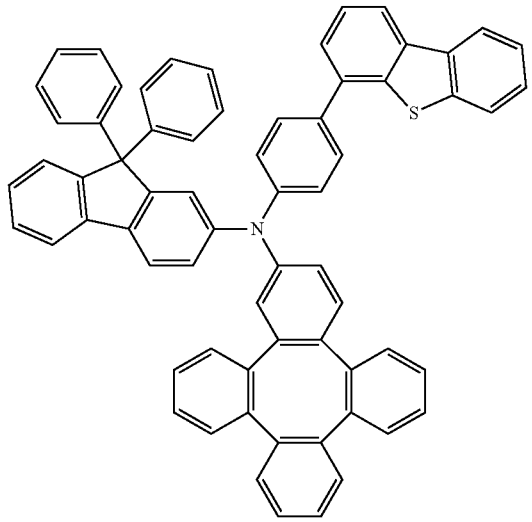
Compound 147
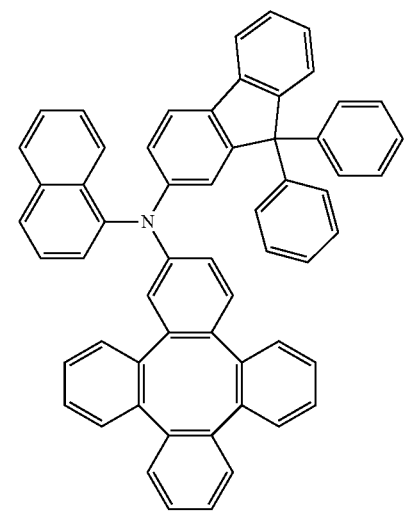
Compound 148
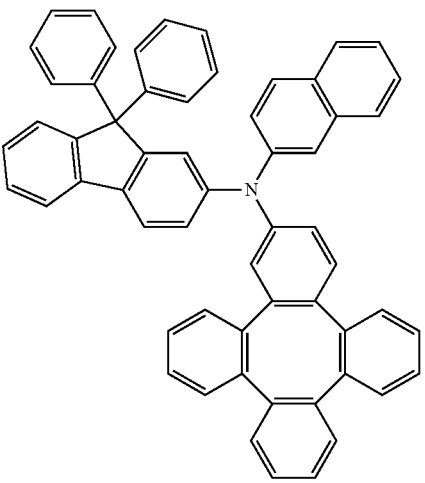

Compound 149
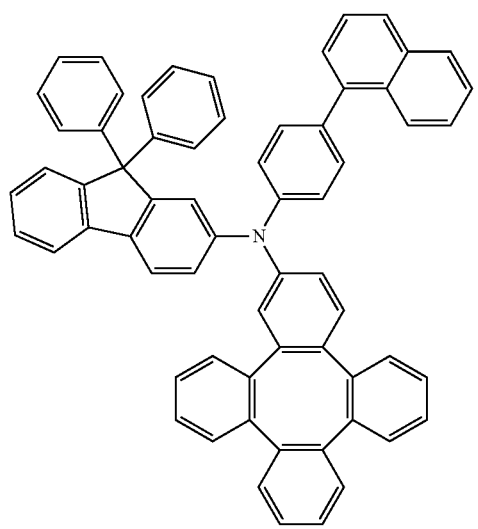
Compound 152
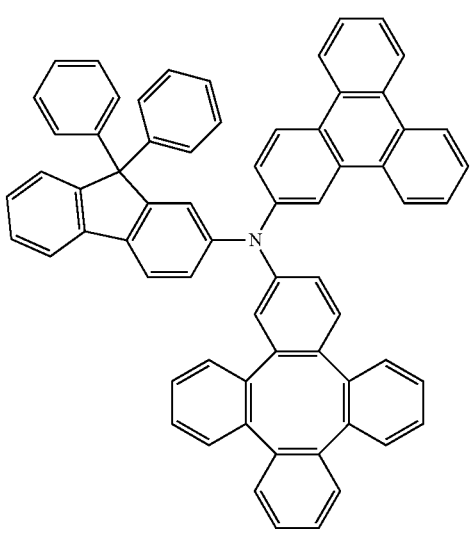
Compound 150
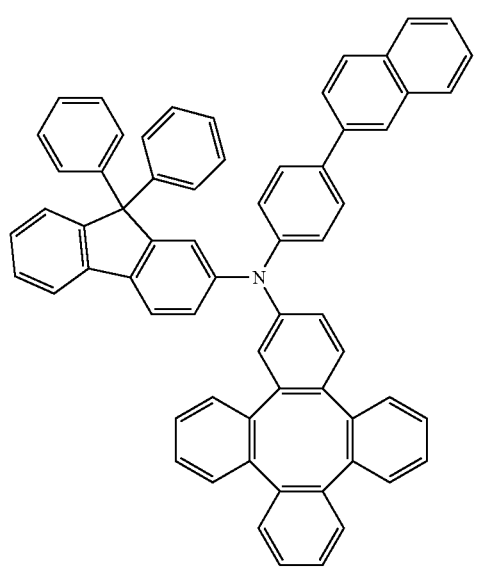
Compound 153
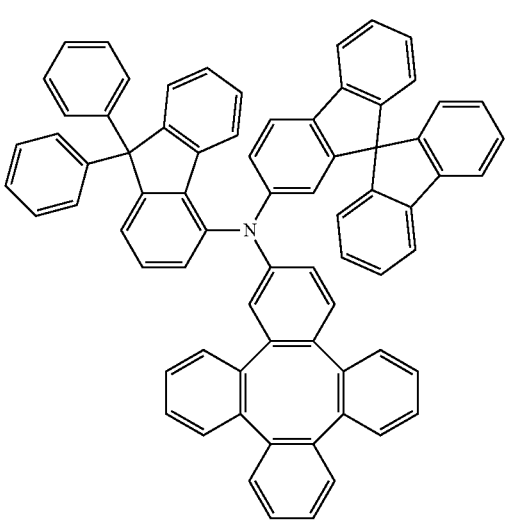
Compound 151
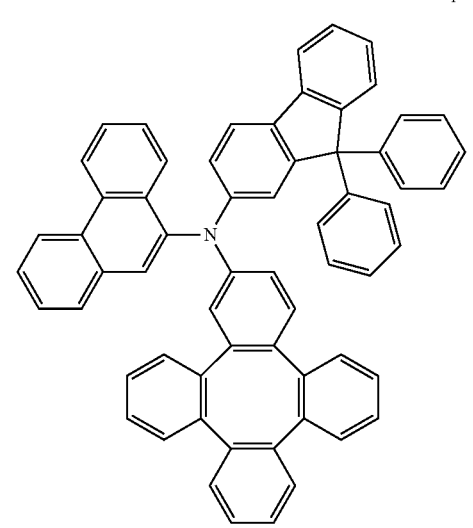
Compound 154
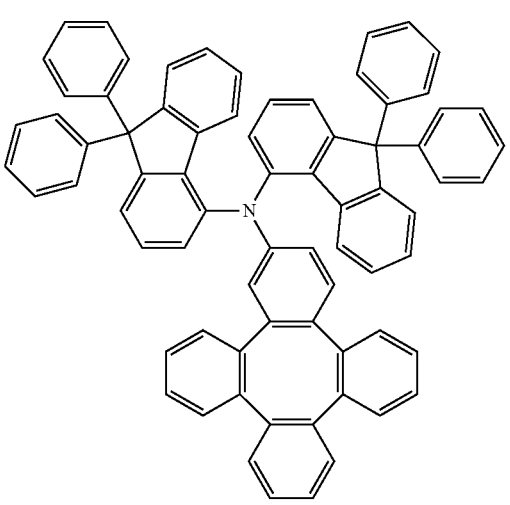

Compound 155
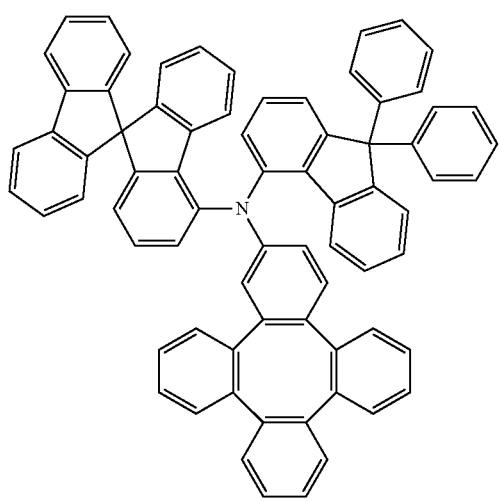
Compound 158
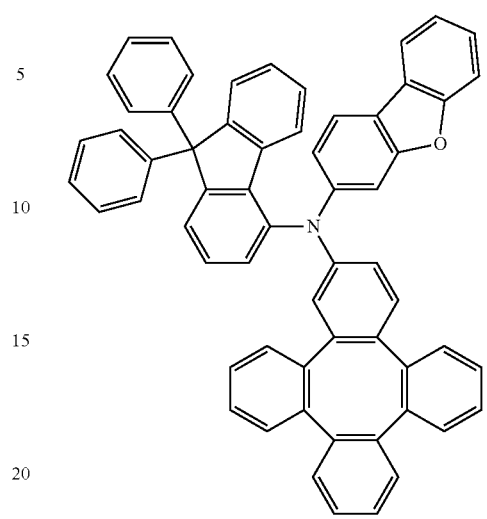
Compound 156
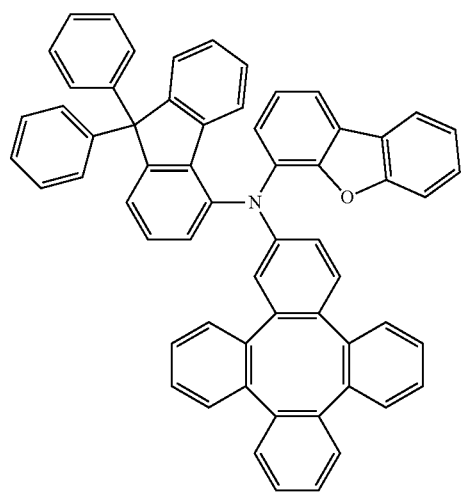
Compound 159
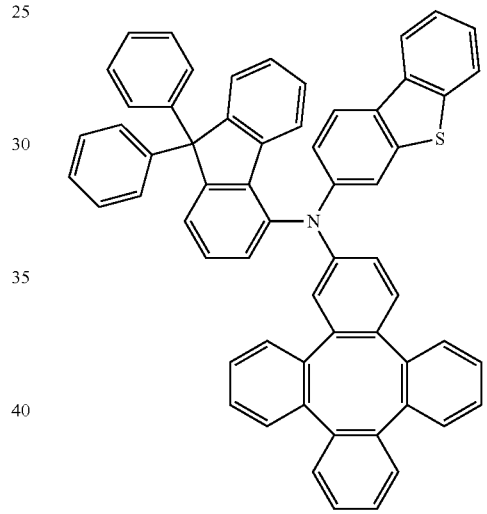
Compound 157
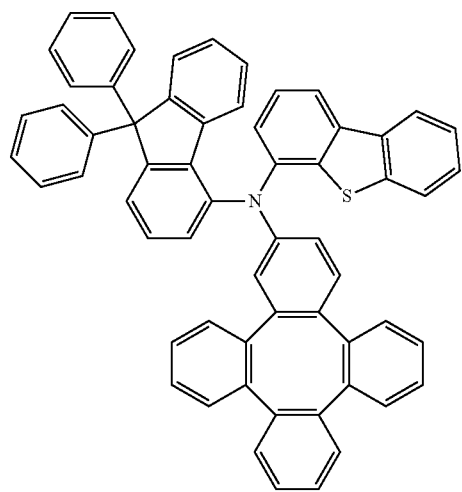
Compound 160
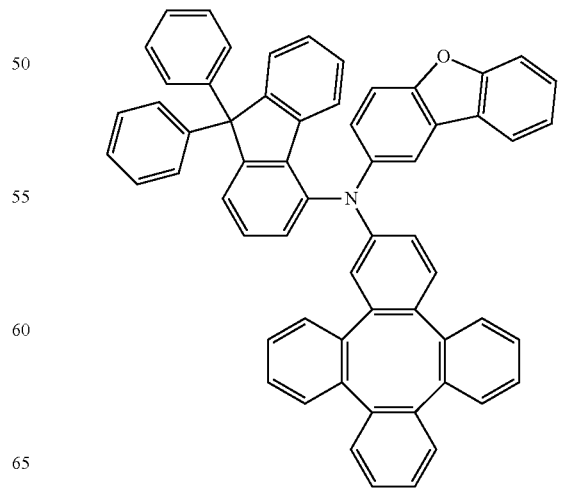

Compound 161
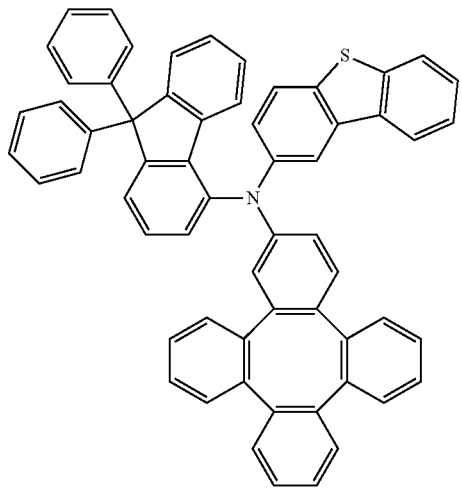
Compound 162
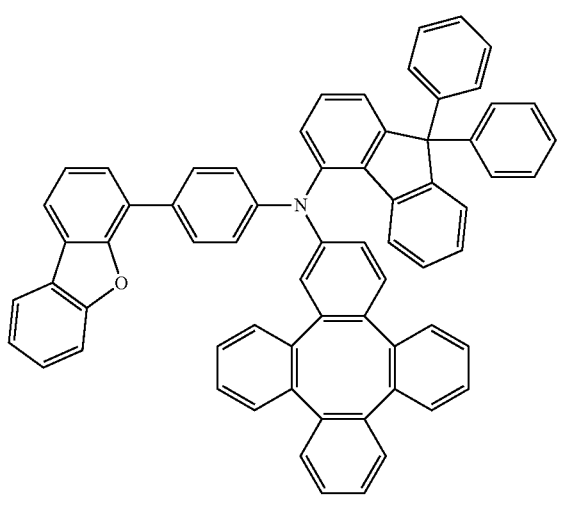
Compound 163
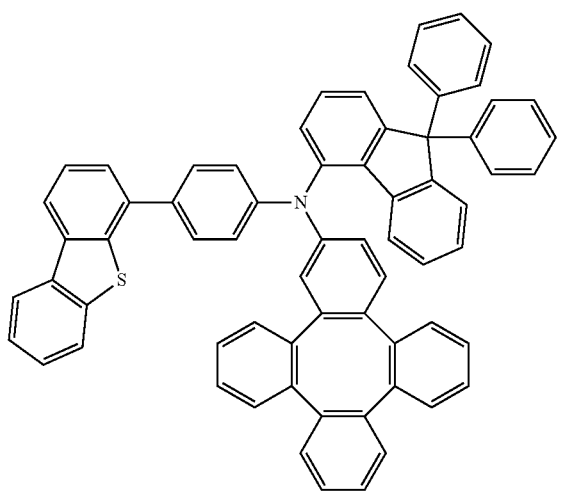
Compound 164
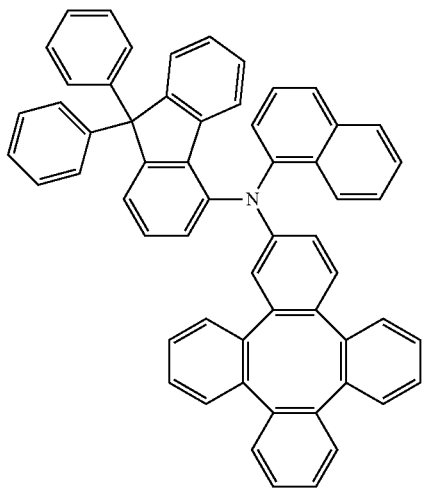
Compound 165
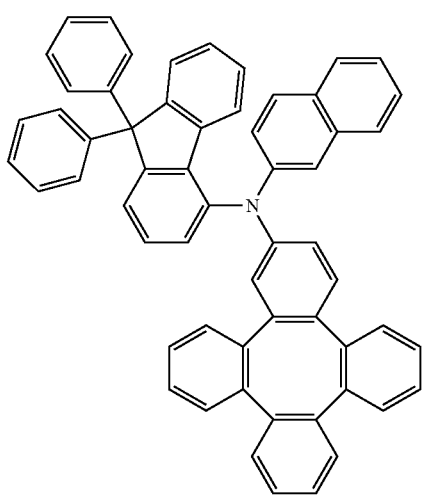
Compound 166
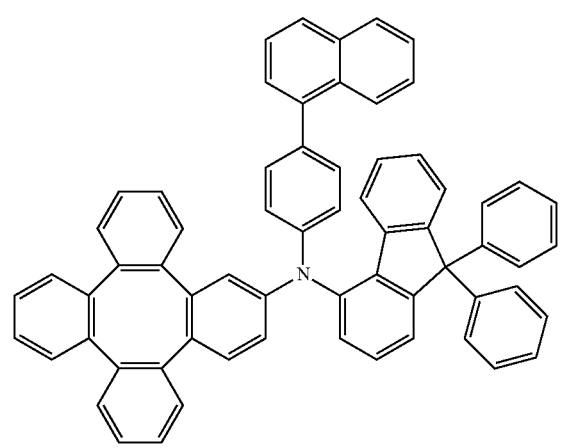

Compound 167
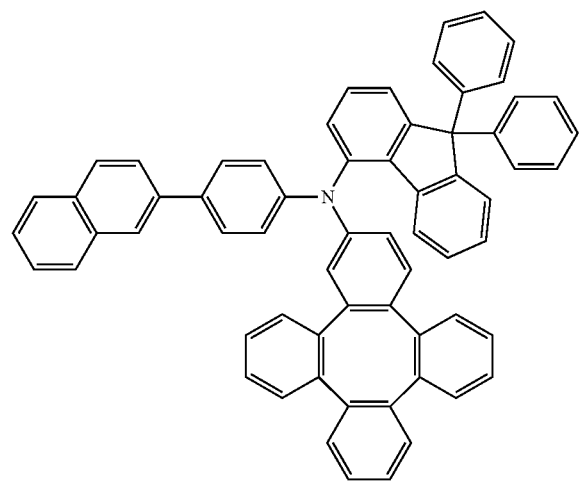
Compound 168
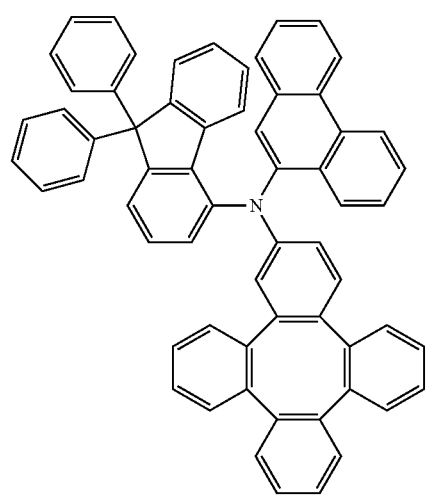
Compound 169
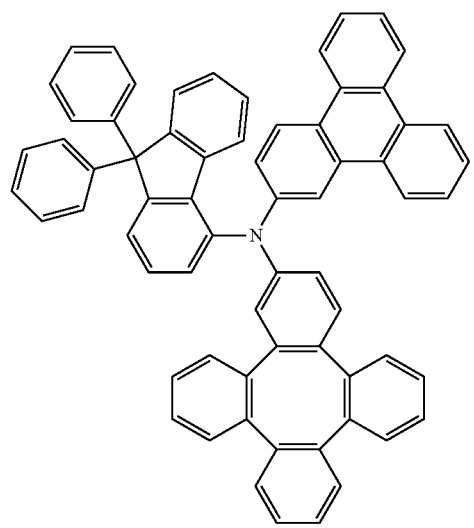
Compound 170
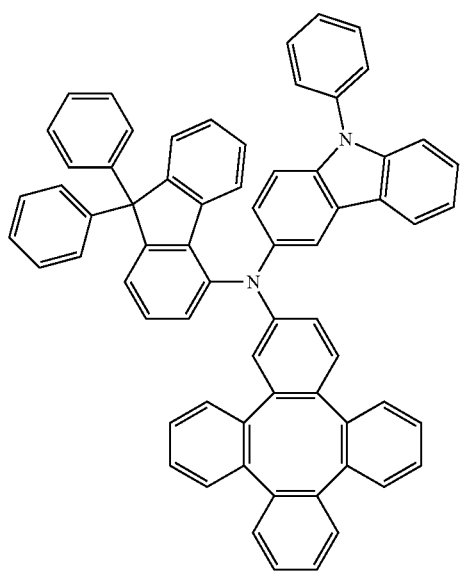
Compound 171
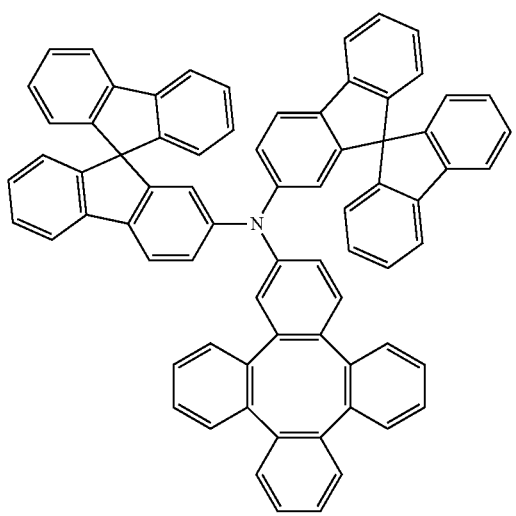
Compound 172

Compound 173
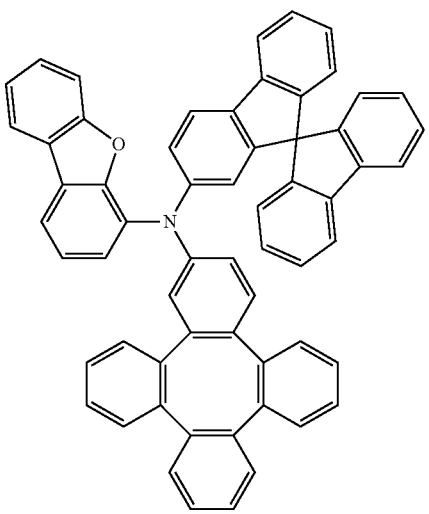
Compound 174
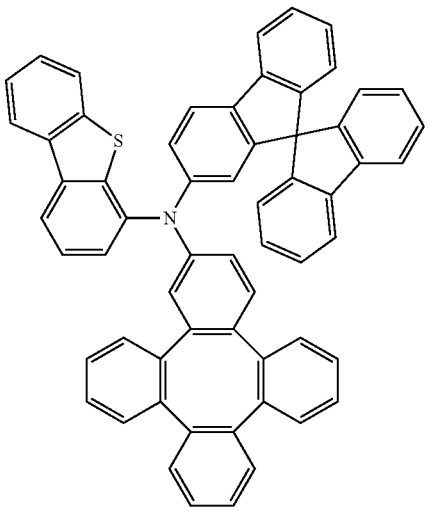
Compound 175
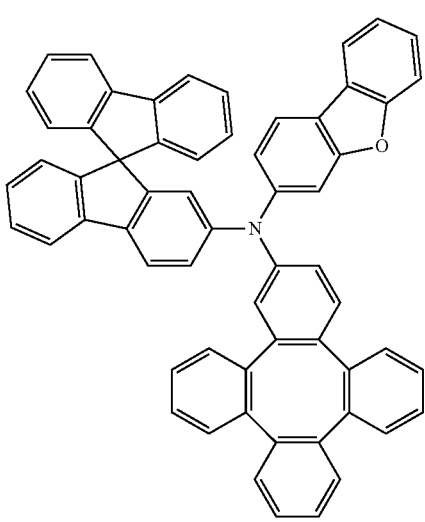
Compound 176
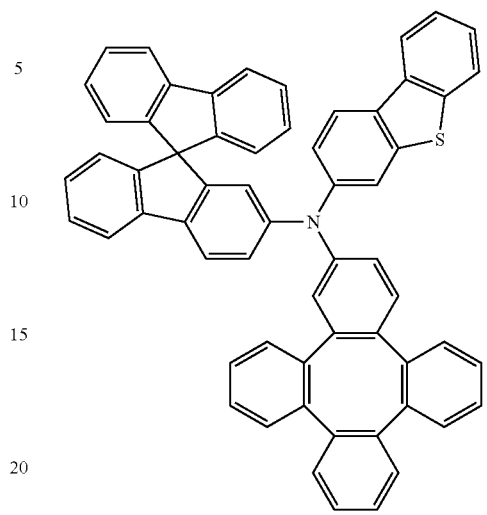
Compound 177
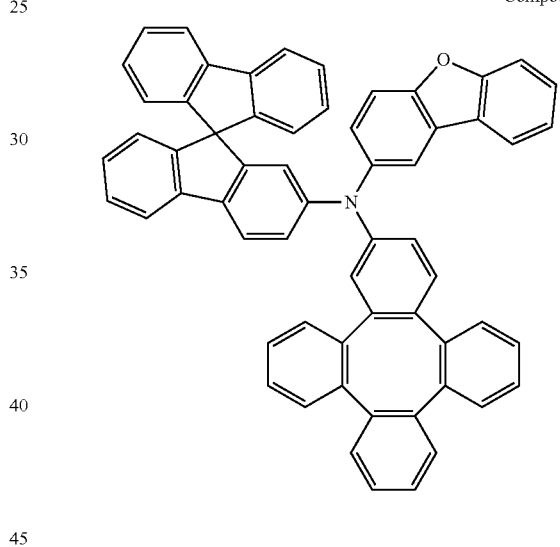
Compound 178
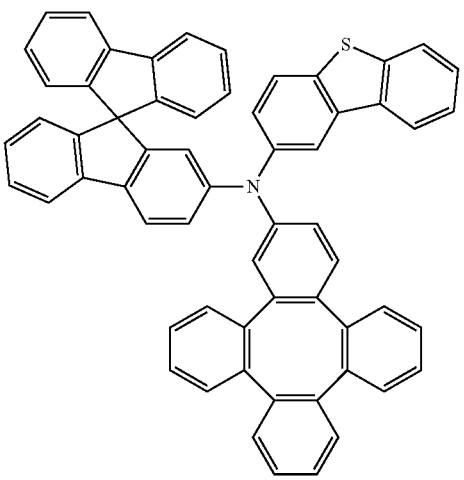

Compound 179
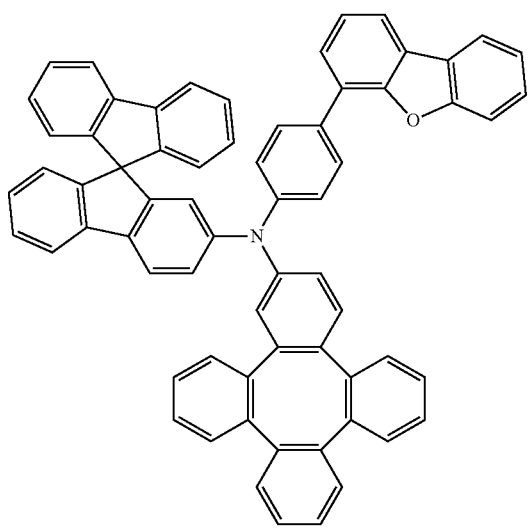
Compound 180
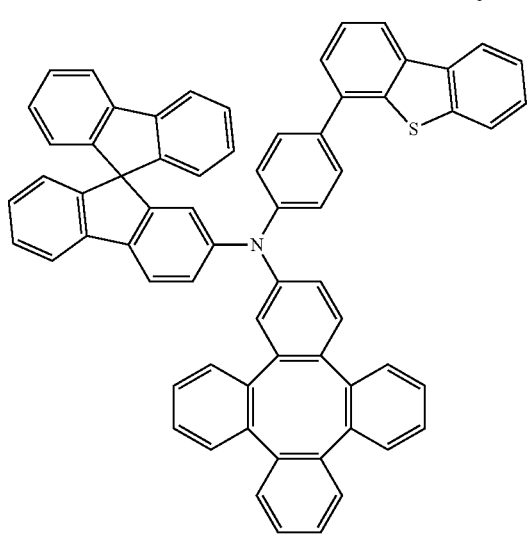
Compound 181
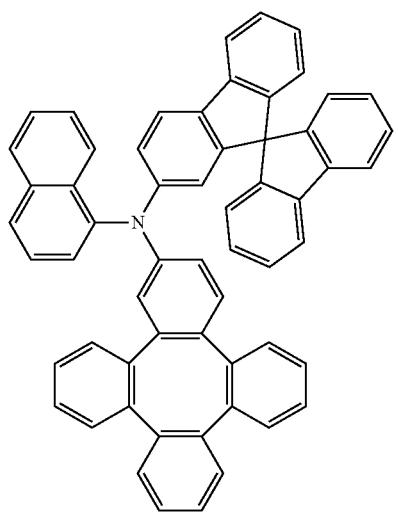
Compound 182
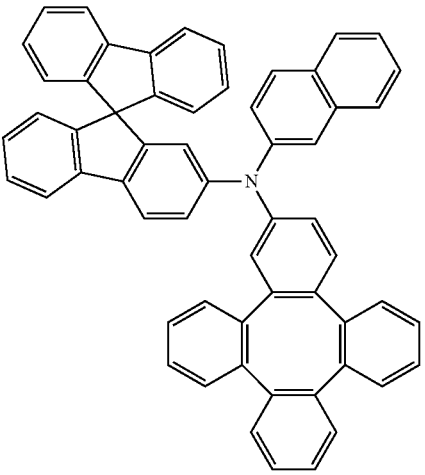
Compound 183
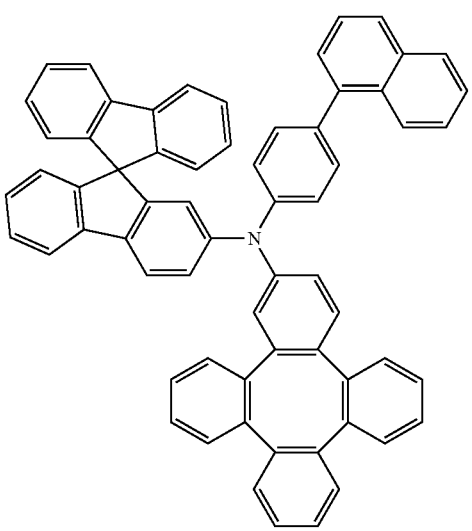
Compound 184
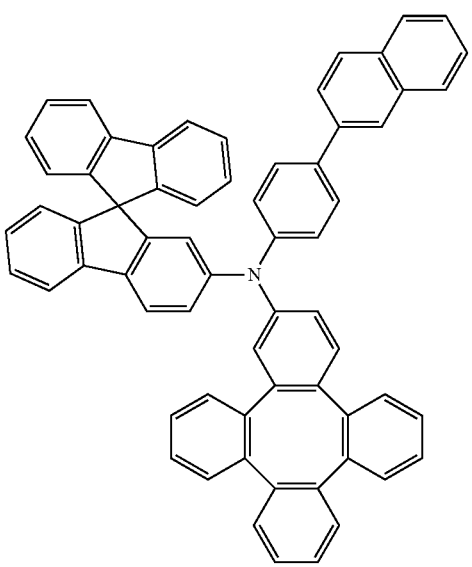

Compound 185
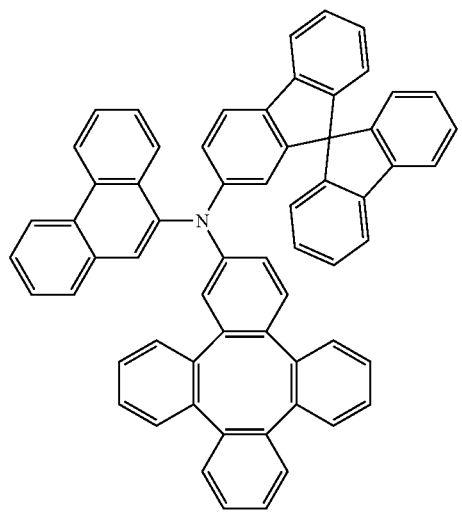
Compound 188
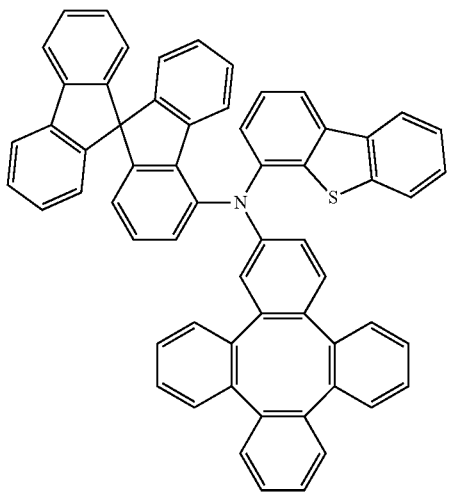
Compound 186
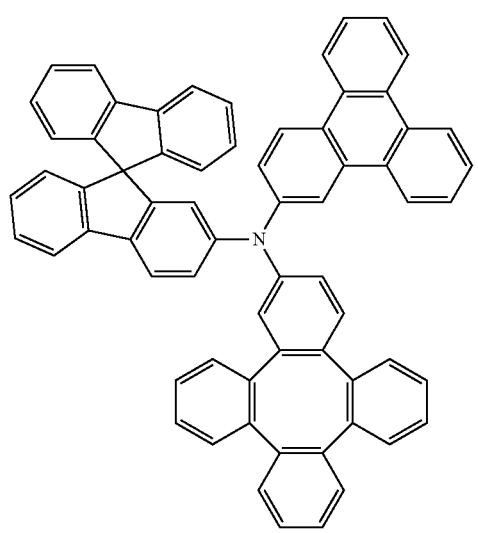
Compound 189
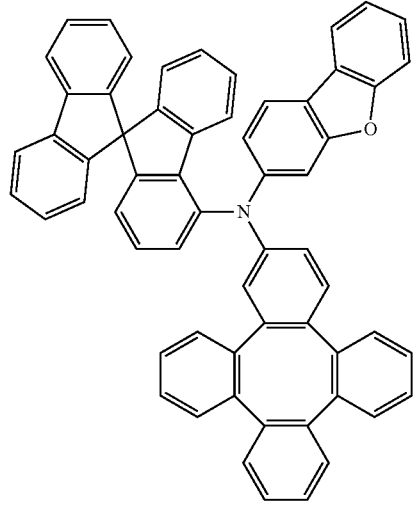
Compound 187
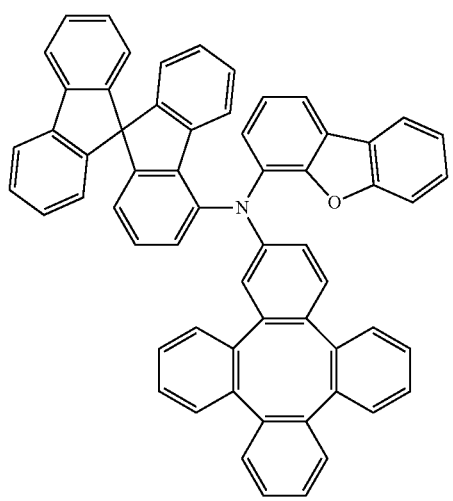
Compound 190
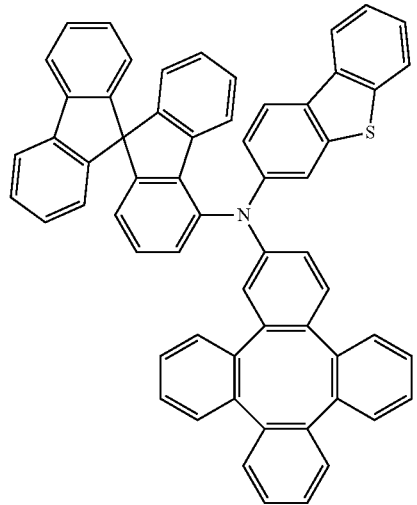

Compound 191
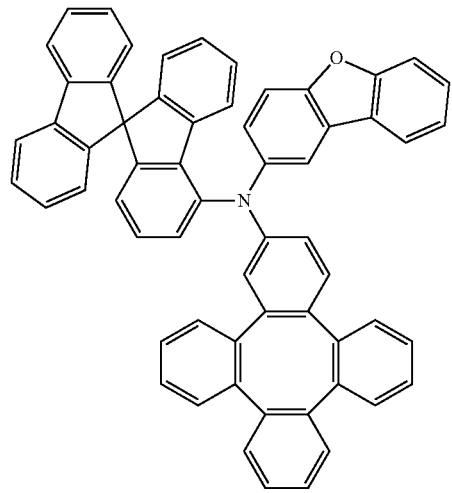
Compound 194
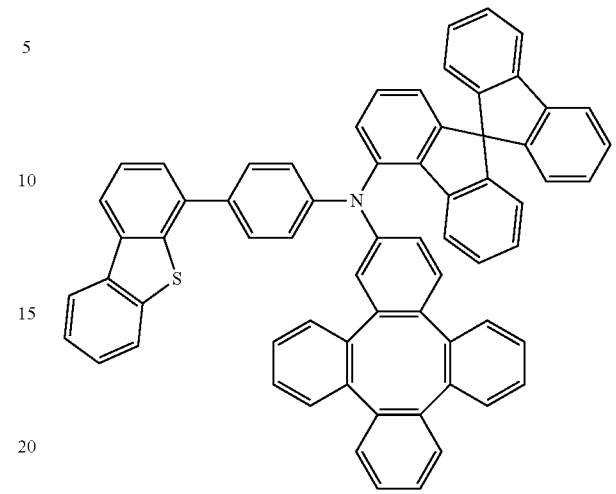
Compound 192
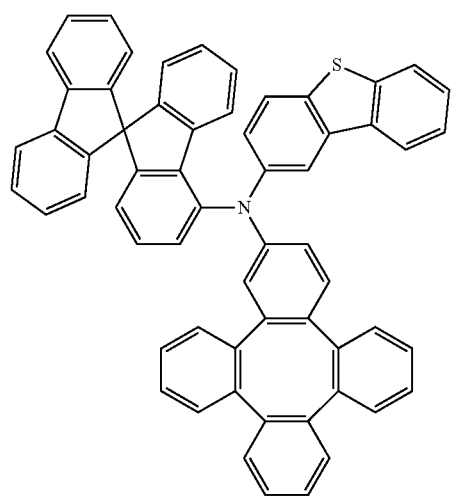
Compound 195
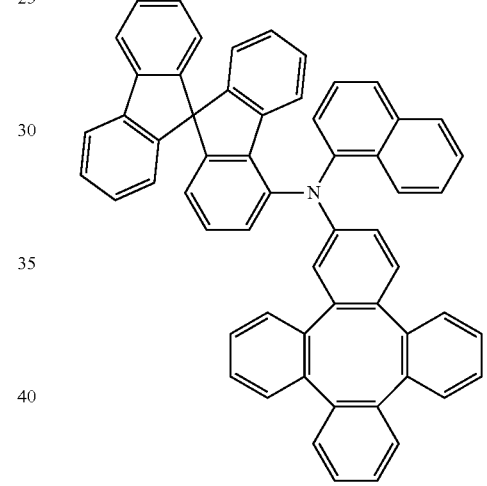
Compound 193
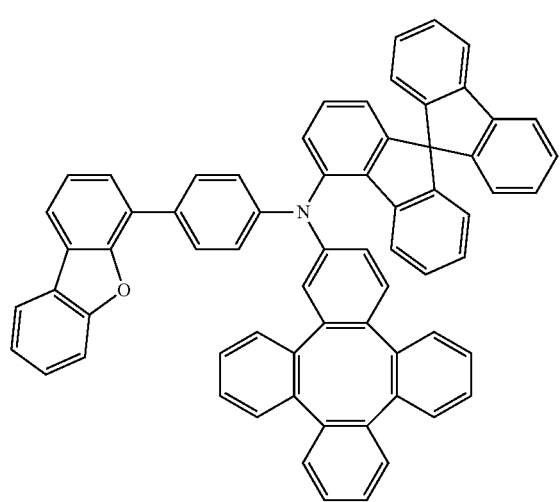
Compound 196
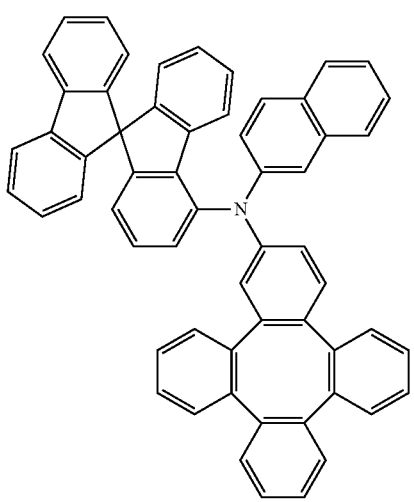

Compound 197
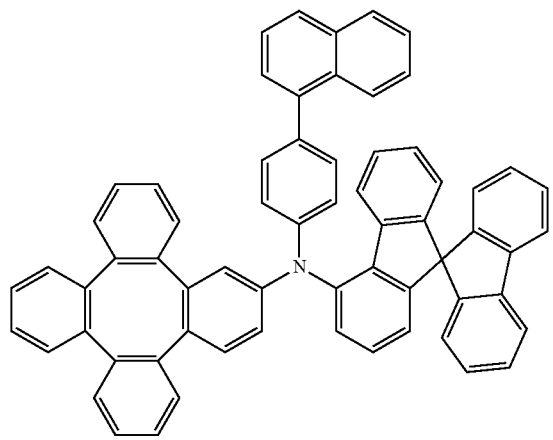
Compound 198
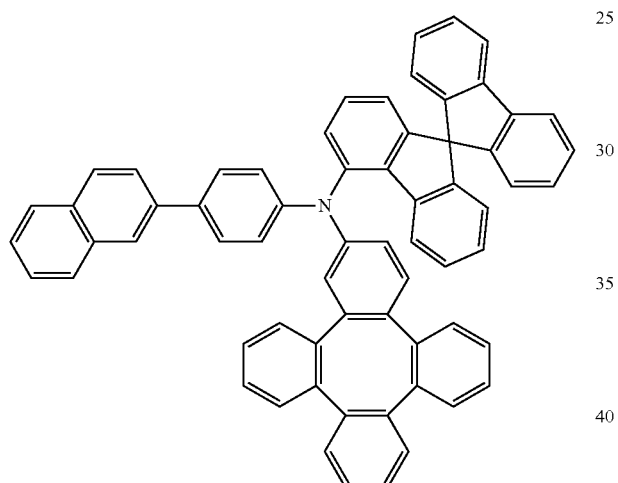
Compound 199
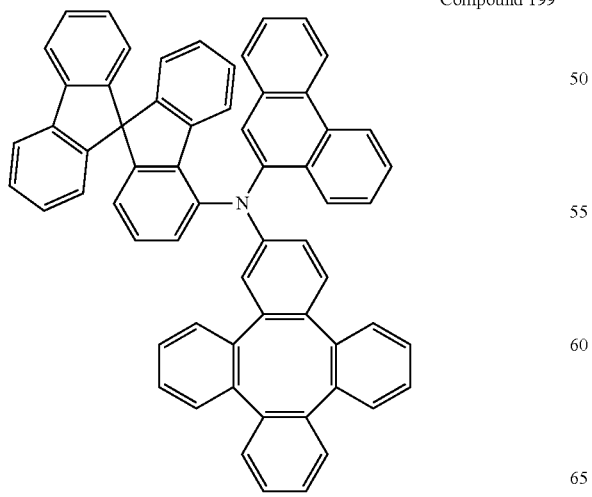
Compound 200
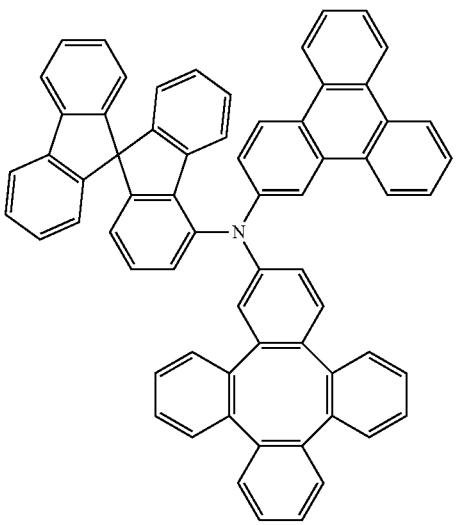
Compound 201
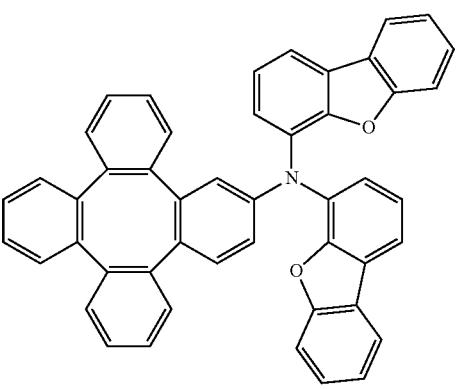
Compound 202
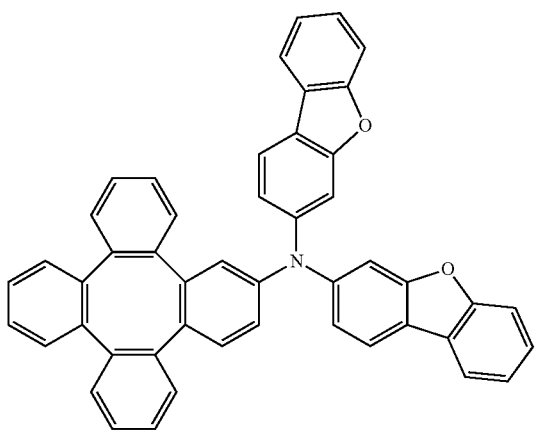

Compound 203
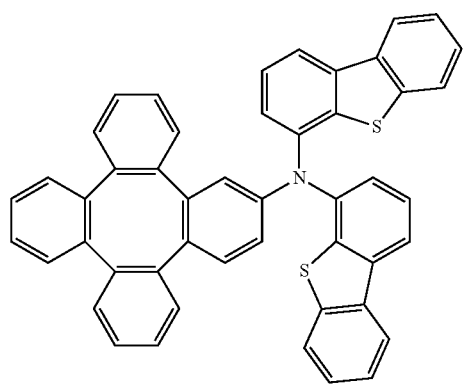
Compound 204
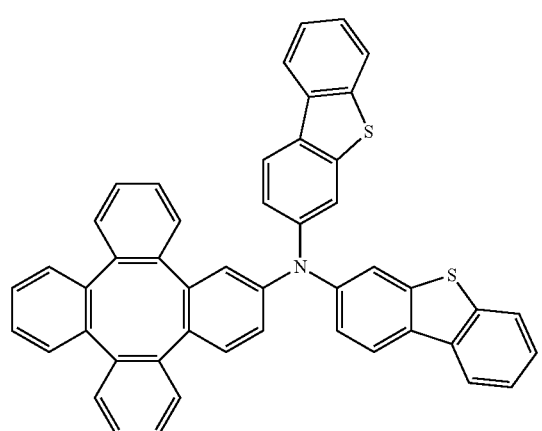
Compound 205
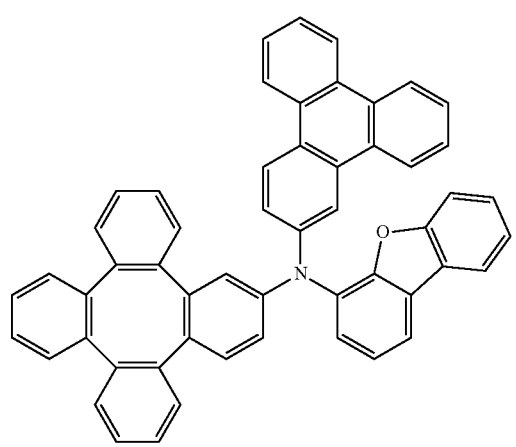
Compound 206
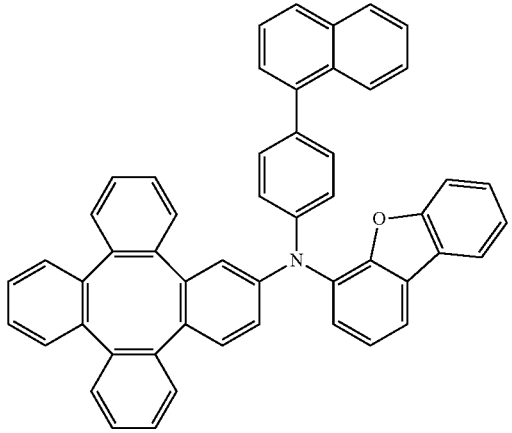
Compound 207
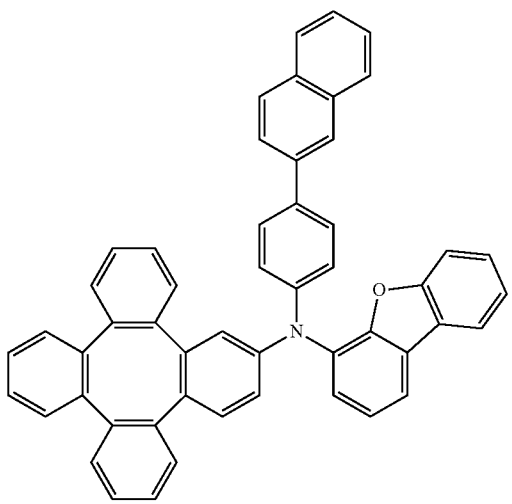
Compound 208
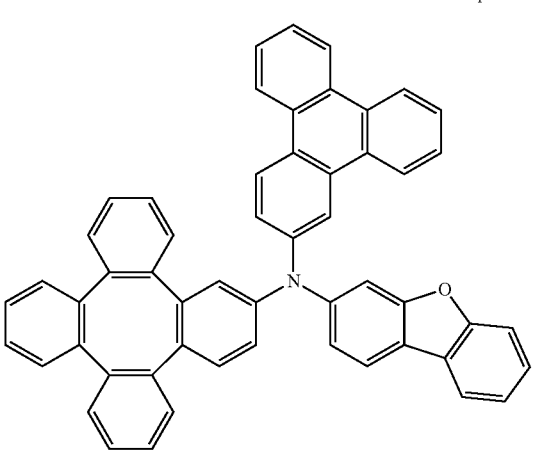

Compound 209
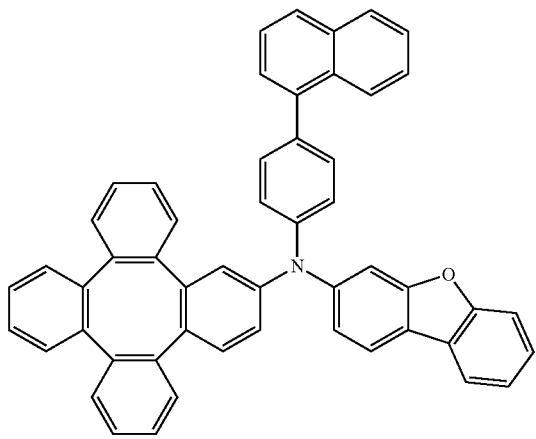
Compound 212
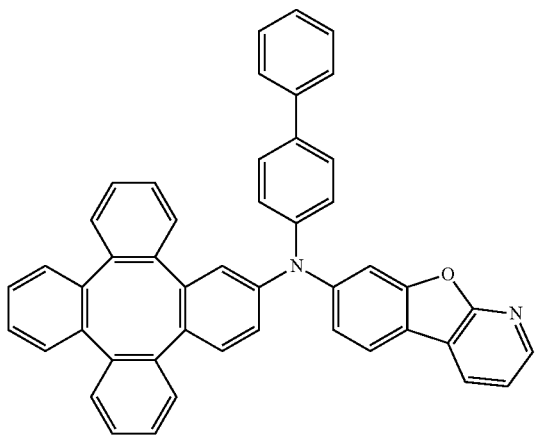
Compound 210
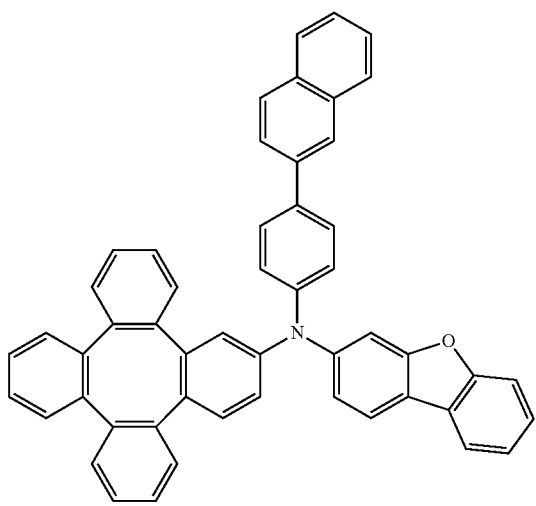
Compound 213
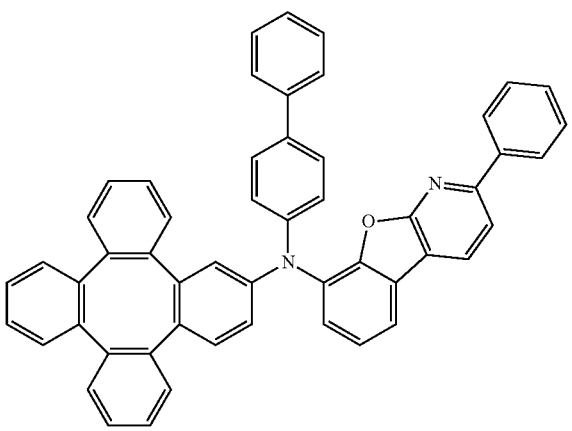
Compound 211
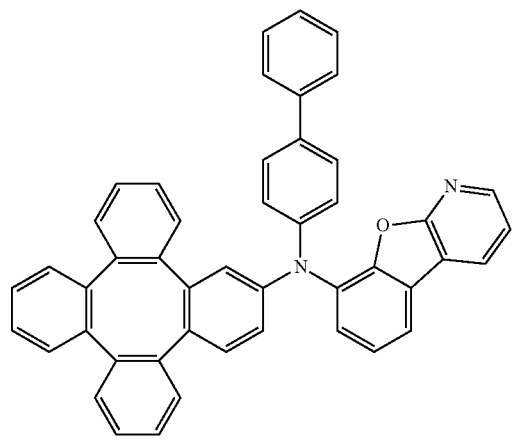
Compound 214
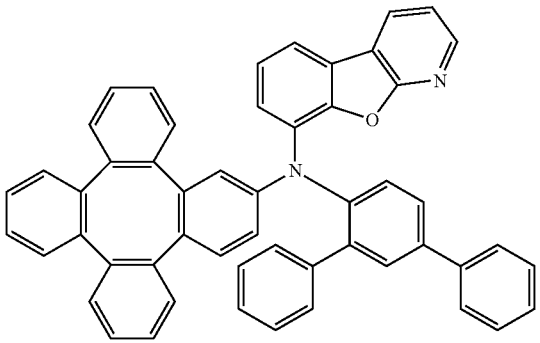

Compound 215
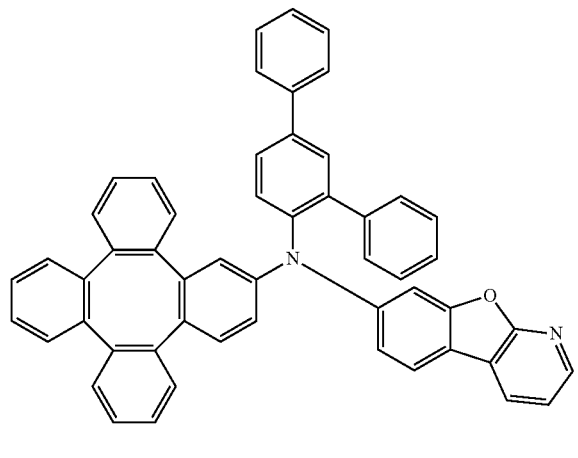
Compound 216
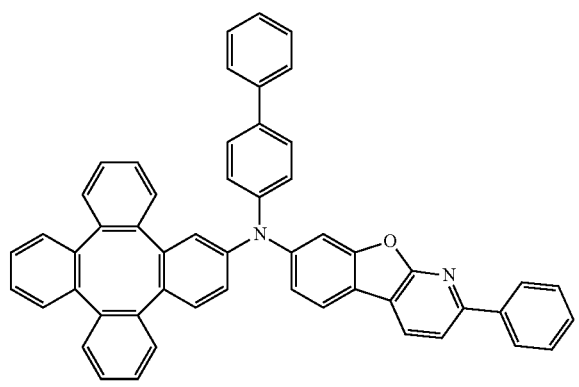
Compound 217
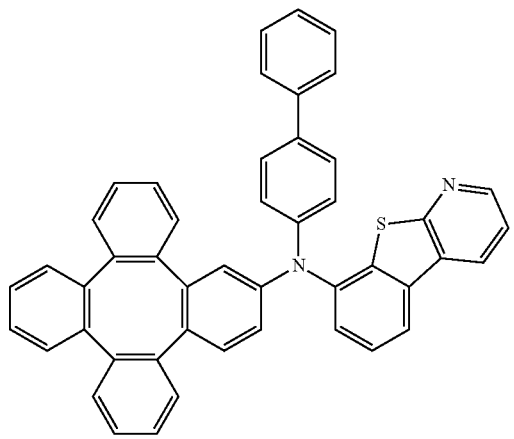
Compound 218
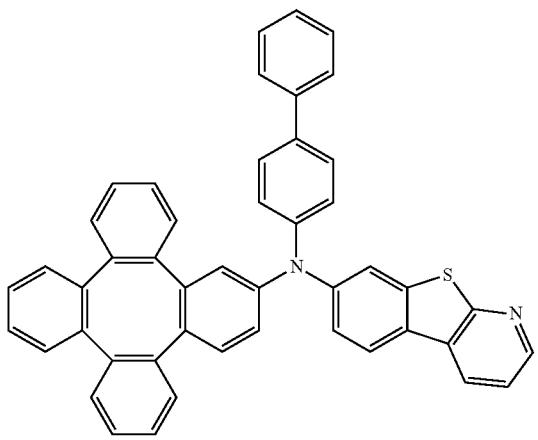
Compound 219
Compound 220
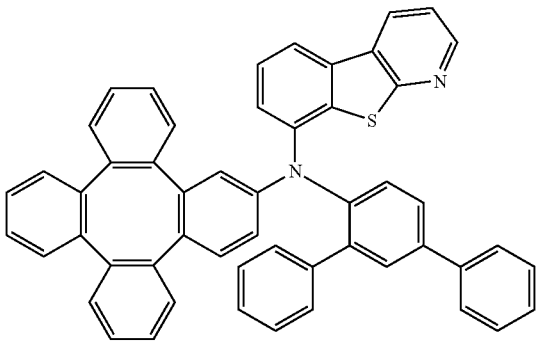

Compound 221
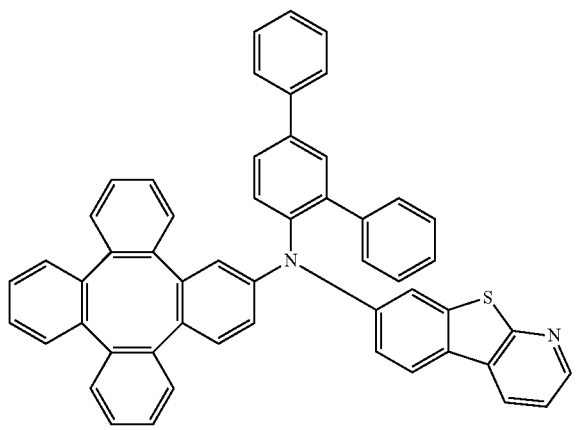
Compound 224
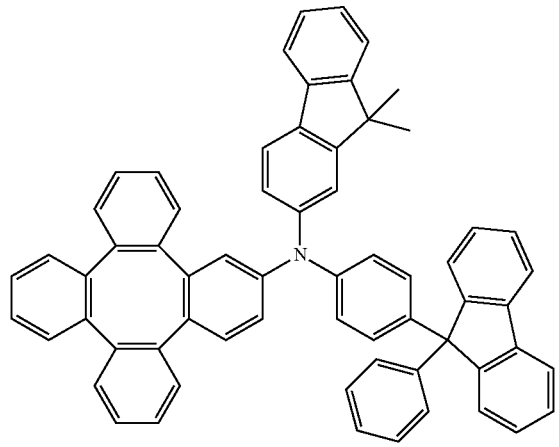
Compound 222
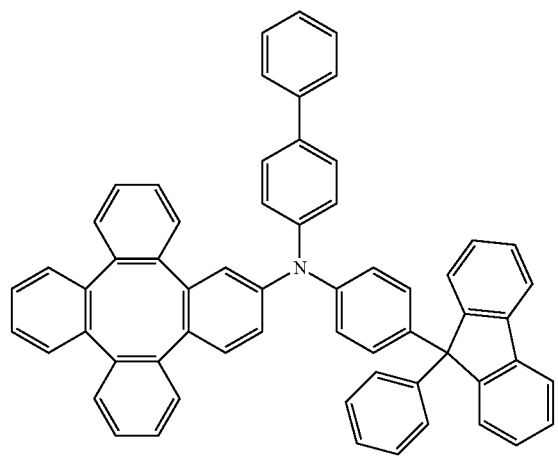
Compound 225
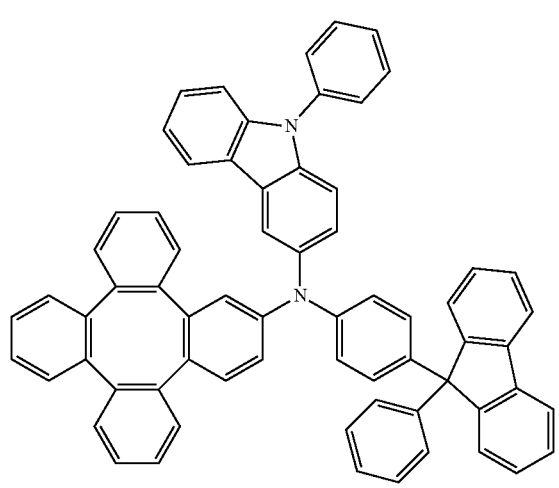
Compound 223
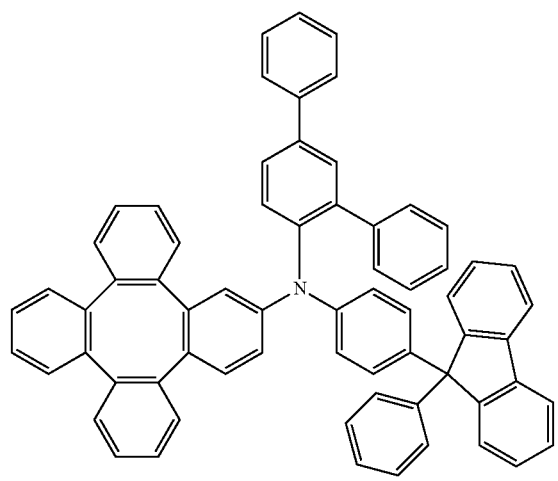
Compound 226
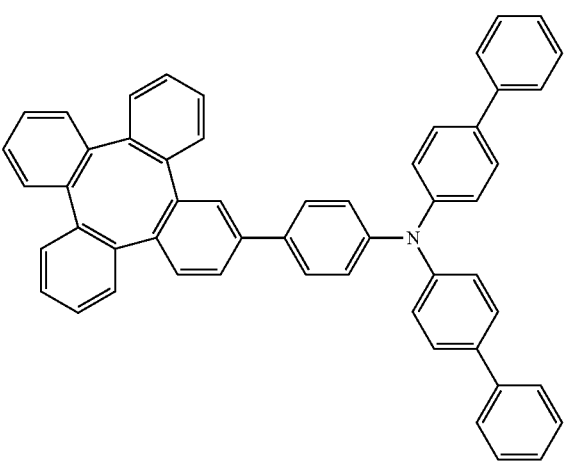

Compound 227
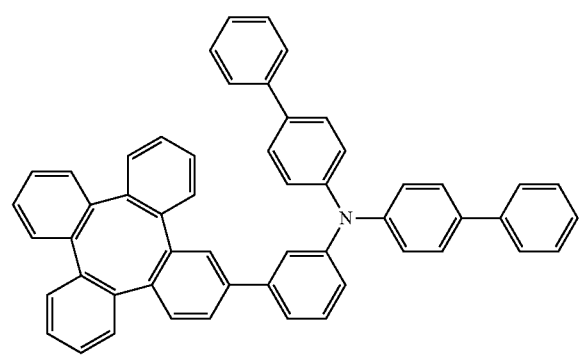
Compound 230
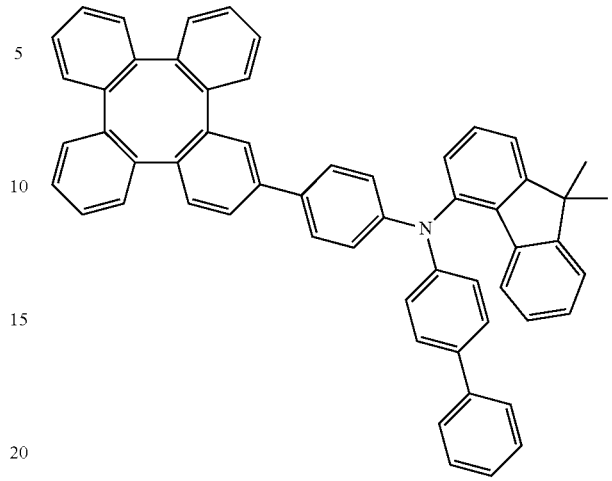
Compound 228
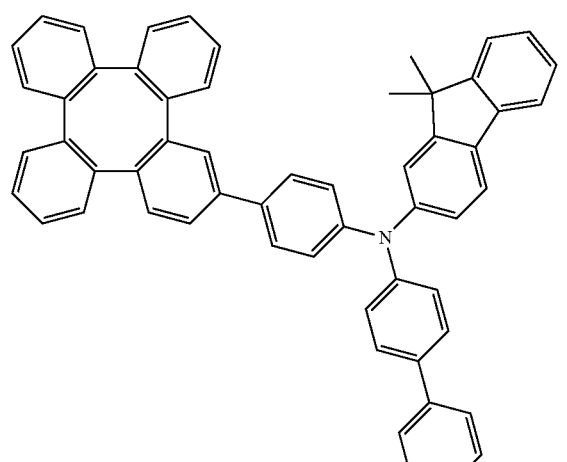
Compound 231
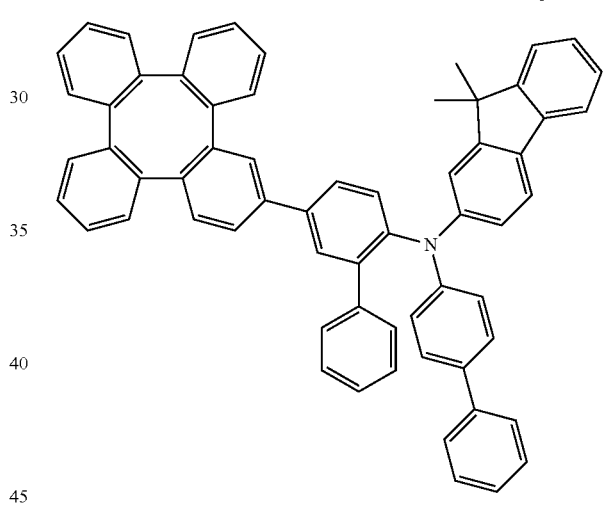
Compound 229
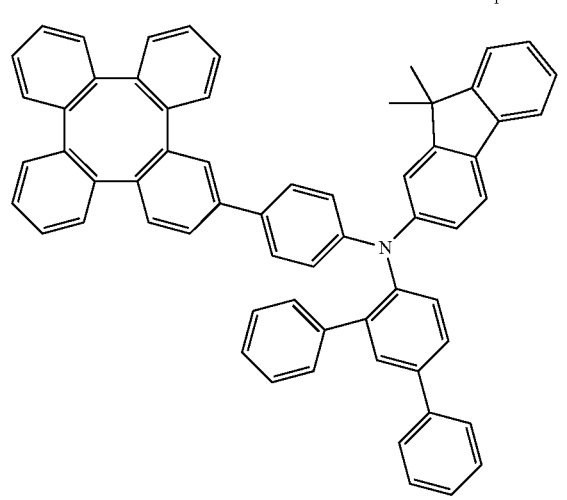
Compound 232
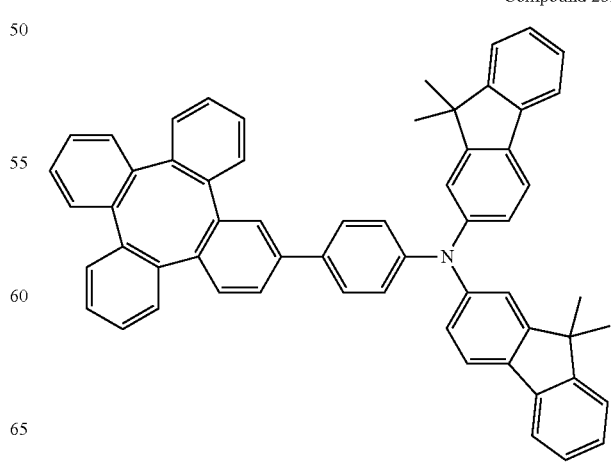

-continued

Compound 233

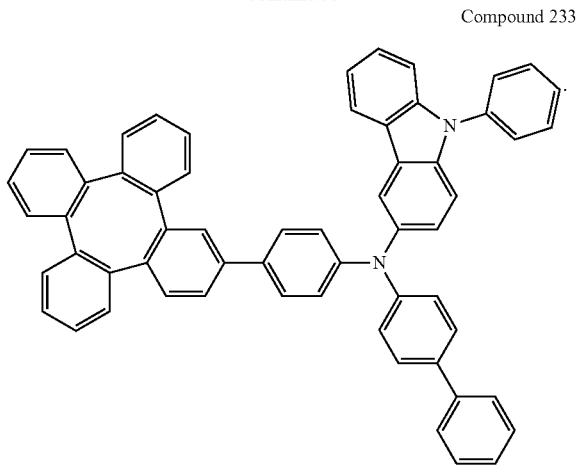

According to an embodiment of the present invention, an electroluminescent device is disclosed. The electroluminescent device comprises:
an anode,
a cathode,
and a series of organic layers disposed between the anode and cathode, wherein at least one of the organic layers comprises a compound having Formula 1:

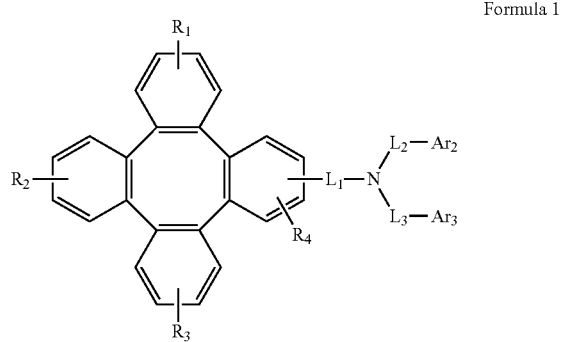

Formula 1 wherein
$R_1$, $R_2$, $R_3$ and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

$Ar_2$ and $Ar_3$ are each independently selected from the group consisting of a substituted or unsubstituted aryl group having 6 to 50 ring carbon atoms, a substituted or unsubstituted heteroaryl group having 5 to 50 ring atoms, and combinations thereof;

$L_1$, $L_2$ and $L_3$ are each independently selected from the group consisting of a single bond, an arylene group having 6 to 30 ring carbon atoms, a heteroarylene group having 5 to 30 ring atoms, and combinations thereof;

Any adjacent substitution can be optionally joined to form a ring or fused structure.

According to an embodiment of the present invention, wherein the device comprises a hole transporting layer, wherein the hole transporting layer comprises a compound having Formula 1.

According to an embodiment of the present invention, wherein the device comprises a hole injection layer, wherein the hole injection layer comprises a compound having Formula 1.

According to an embodiment of the present invention, wherein the device comprises a hole injection layer, wherein the hole injection layer further comprises a p-type conductive dopant.

According to an embodiment of the present invention, wherein the device comprises an electron blocking layer, wherein the electron blocking layer comprises a compound having Formula 1.

According to yet another embodiment of the present invention, a formulation comprising a compound according to Formula 1 is also disclosed. The specific structure of the compound is described in any of the above embodiments.

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, the compounds disclosed herein may be used in combination with a wide variety of emissive dopants, hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHI- MADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

SYNTHESIS EXAMPLES

The method for preparing the compounds of the present invention is not limited. The following compounds are exemplified as a typical but non-limiting example, and the synthesis route and preparation method are as follows:

Synthesis Example 1: Synthesis of Compound 1

Step 1: Synthesis of Intermediate 1-a

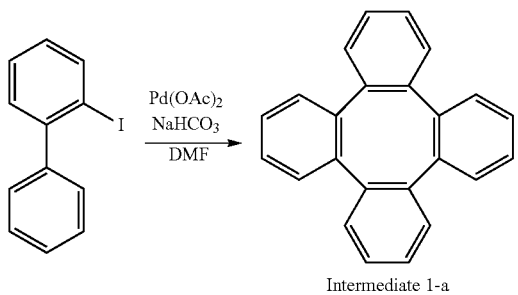

Intermediate 1-a

A mixture of 2-iodobiphenyl (112 g, 400 mmol), Pd(OAc)$_2$ (4.5 g, 20 mmol), NaHCO3 (80 g, 960 mmol) in 1000 mL of DMF was heated at 130° C. in air for 36 h. After cooling to room temperature, the solvent was removed under reduced pressure. The crude product was further purified by column chromatography on silica gel to afford Intermediate 1-a (30.2 g, 24.7% yield).

Step 2: Synthesis of Intermediate 1-b

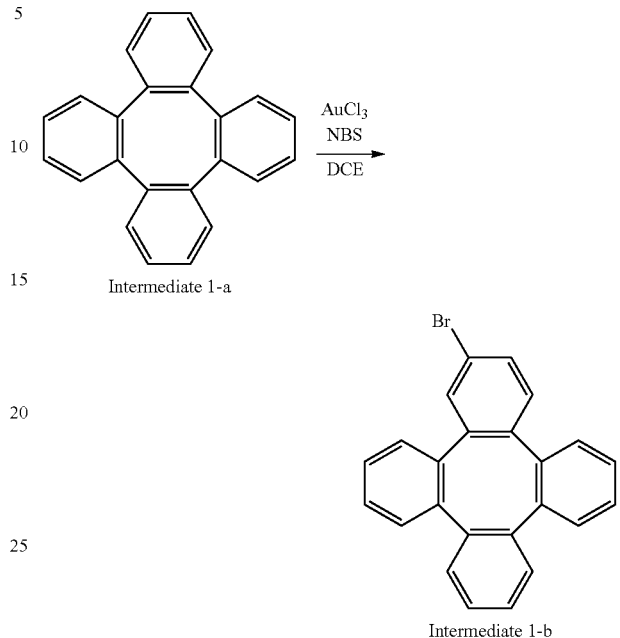

A mixture of Intermediate 1-a (15 g, 50 mmol), AuCl$_3$ (1.0 g, 3.0 mmol), NBS (13.5 g, 75 mmol) in 500 mL of DCE was heated at 80° C. under N$_2$ for 24 h. After cooling to room temperature, the reaction mixture was diluted with ethyl acetate and then filtered through a small pad of Celite. The filtrate was concentrated in vacuo. The crude product was further purified by column chromatography on silica gel to afford Intermediate 1-b (10.3 g, 54% yield).

Step 3: Synthesis of Compound 1

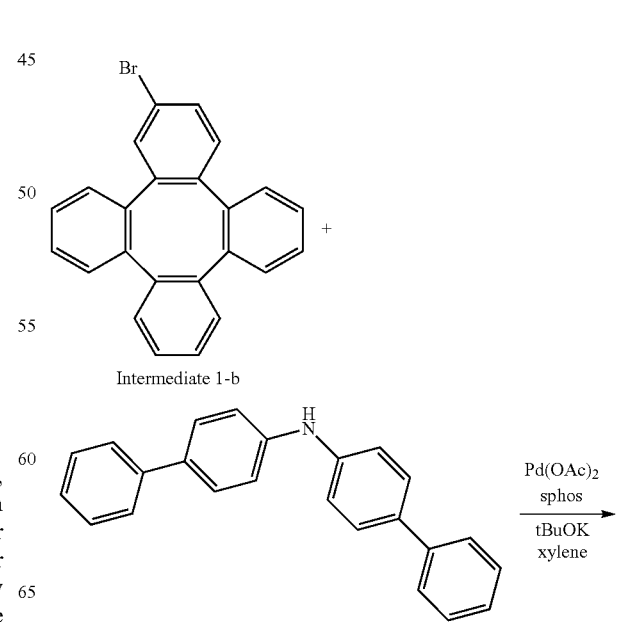

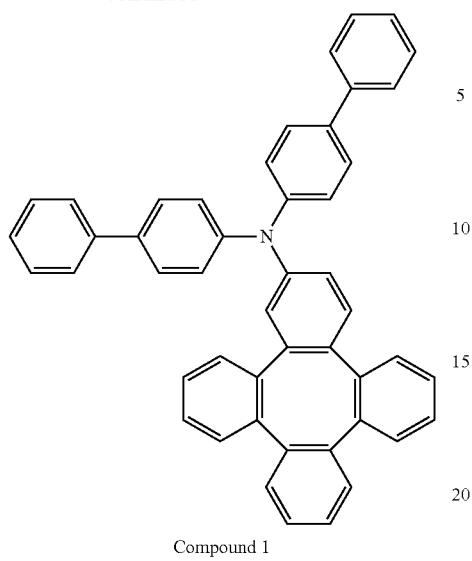

Compound 1

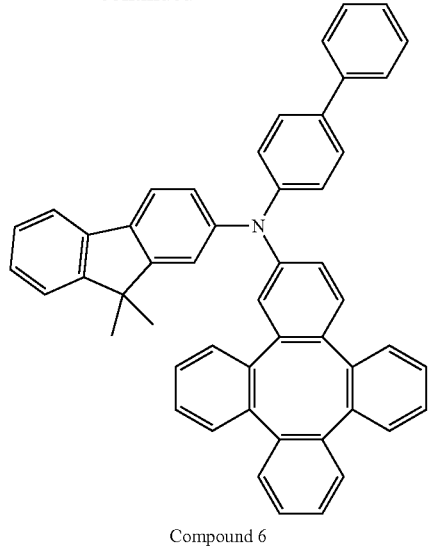

Compound 6

A mixture of Intermediate 1-b (5 g, 13 mmol), bis(4-biphenylyl)amine (4.2 g, 13 mmol), Pd(OAc)₂ (292 mg, 1.3 mmol), sphos (800 mg, 1.9 mmol), potassium tert-butoxide (4.4 g, 39 mmol) in 100 mL of xylene was heated at 140° C. under N₂ for 15 h. After cooling to room temperature, the solvent was removed under reduced pressure. The crude product was extracted with DCM. The organic layer was further purified by column chromatography on silica gel to afford Compound 1 (5.2 g, 60.3% yield). The product was confirmed as the target product, having a molecular weight of 624.

Synthesis Example 2: Synthesis of Compound 6

A mixture of Intermediate 1-b (5 g, 13 mmol), N-(4-biphenyl)-(9,9-dimethylfluoren-2-yl)amine (4.7 g, 13 mmol), Pd(OAc)₂ (292 mg, 1.3 mol), sphos (800 mg, 1.9 mmol), potassium tert-butoxide (4.4 g, 39 mmol) in 100 mL of xylene was heated at 140° C. under N₂ for 15 h. After cooling to room temperature, the solvent was removed under reduced pressure. The crude product was extracted with DCM. The organic layer was further purified by column chromatography on silica gel to afford Compound 6 (6.5 g, 75.4% yield). The product was confirmed as the target product, having a molecular weight of 664.

Synthesis Example 3: Synthesis of Compound 228

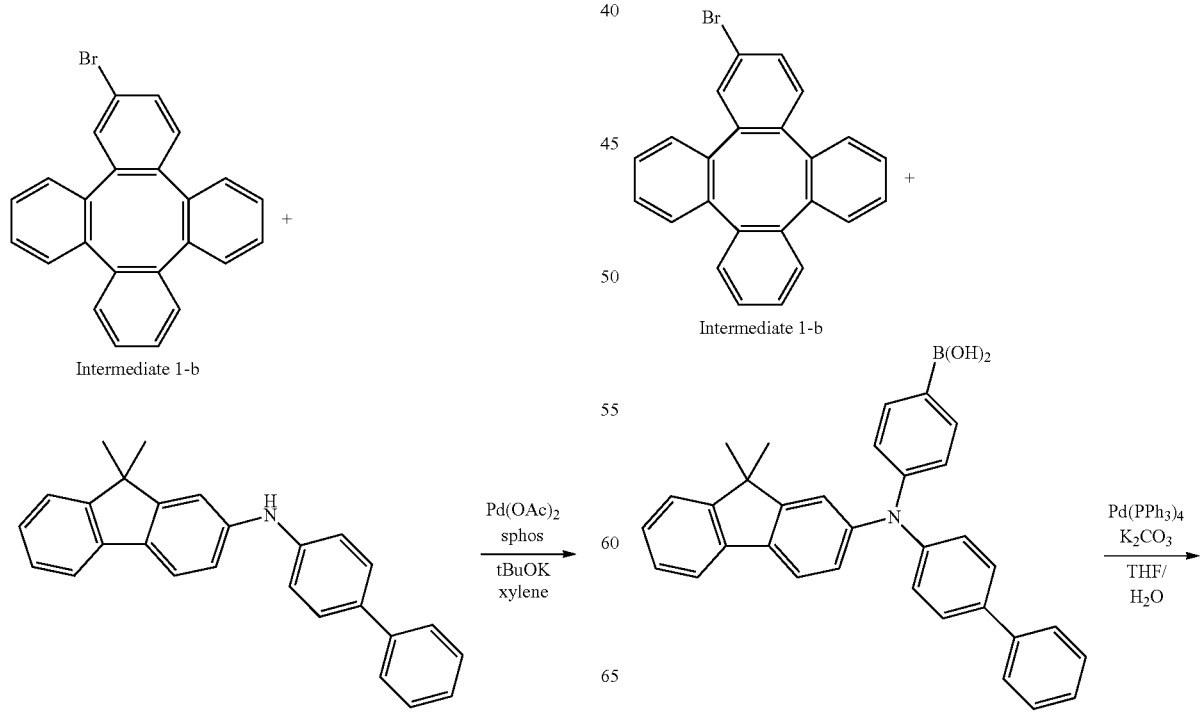

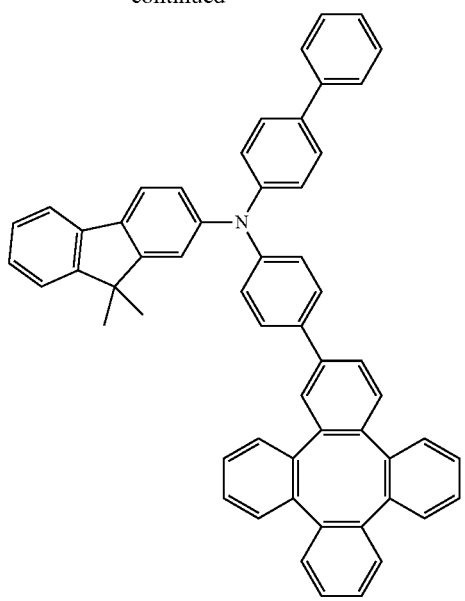

Compound 228

A mixture of Intermediate 1-b (5.4 g, 14 mmol), [4-[[1,1'-biphenyl]-4-yl(9,9-dimethyl-9H-fluoren-2-yl)amino]phenyl]-boronic acid (6.7 g, 14 mmol), Pd(PPh₃)₄ (809 mg, 0.7 mmol), potassium carbonate (5.8 g, 42 mmol) in 90 mL of THF and 30 mL of H₂O was heated at 85° C. under N₂ for 12 h. After cooling to room temperature, the solvent was removed under reduced pressure. The crude product was extracted with DCM. The organic layer was further purified by column chromatography on silica gel to afford Compound 228 (9.3 g, 84.7% yield). The product was confirmed as the target product, having a molecular weight of 740.

Synthesis Example 4: Synthesis of Compound 91

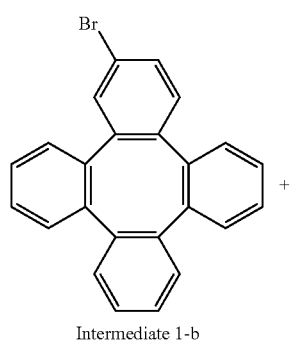

Intermediate 1-b

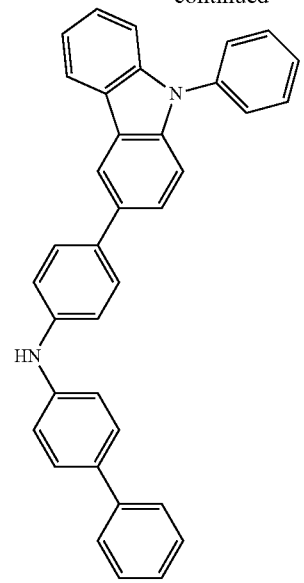

$$\xrightarrow{\text{Pd(OAc)}_2,\ \text{sphos},\ \text{tBuOK},\ \text{xylene}}$$

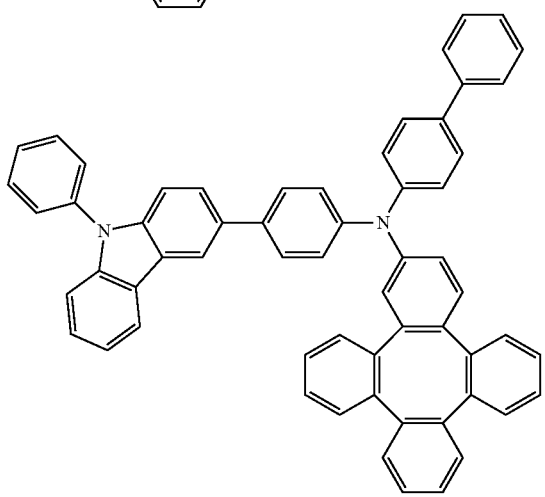

Compound 91

A mixture of Intermediate 1-b (5.6 g, 14.5 mmol), N-(4-(9-phenyl-9H-carbazol-3-yl)phenyl)-[1,1'-biphenyl]-4-amine (7.5 g, 14.5 mmol), Pd(OAc)₂ (325 mg, 1.5 mmol), sphos (895 mg, 2.2 mmol), potassium tert-butoxide (4.8 g, 43 mmol) in 100 mL of xylene was heated at 140° C. under N₂ for 20 h. After cooling to room temperature, the solvent was removed under reduced pressure. The crude product was extracted with DCM. The organic layer was further purified by column chromatography on silica gel to afford Compound 91 (7.5 g, 54.5% yield). The product was confirmed as the target product, having a molecular weight of 789.

The persons skilled in the art should know that the above preparation method is only an illustrative example, and the persons skilled in the art can obtain the structure of other compounds of the present invention by modifying the above preparation method.

Device Example 1

A glass substrate with 80 nm thick indium-tin-oxide (ITO) anode was first cleaned and then treated with oxygen plasma and UV ozone. After the treatments, the substrate was baked dry in a glovebox to remove moisture. The substrate was then mounted on a substrate holder and loaded into a vacuum chamber. The organic layers specified below were deposited in sequence by thermal vacuum deposition on the ITO anode at a rate of 0.2-2 Å/s at a vacuum of around $10^{-8}$ torr. Compound HI (100 Å) was used as the hole injection layer (HIL). Compound HT (350 Å) was used as the hole transporting layer (HTL). Then Compound 1 (50 Å) of the present invention was used as the electron blocking layer (EBL). Compound GD was doped in the host Compound EB and Compound HB (HB:EB:GD=45:45:10) as the emitting layer (EML, 400 Å). On the emitting layer, Compound HB (100 Å) was deposited as the hole blocking layer (HBL). A mixture of Compound ET and 8-quinolinolato-lithium (Liq) (35:65, 350 Å) was deposited as the electron transporting layer (ETL). Finally, 10 Å-thick Liq was deposited as the electron injection layer and 1200 Å of Al was deposited as the cathode. The device was then transferred back to the glovebox and encapsulated with a glass lid and a moisture getter to complete the device.

Device Example 2

Device Example 2 was fabricated in the same manner as Device Example 1, except that Compound 6 was used as electron blocking layer (EBL) in place of Compound 1.

Device Example 3

Device Example 3 was fabricated in the same manner as Device Example 1, except that Compound 228 was used as electron blocking layer (EBL) in place of Compound 1.

In the layers in which more than one material were used, they were obtained by doping different compounds in the weight ratios described therein. The partial device layer structure and thicknesses are shown in the table below:

TABLE 1

Partial structure of device examples

| Device ID | EBL |
|---|---|
| Example 1 | Compound 1 (50 Å) |
| Example 2 | Compound 6 (50 Å) |
| Example 3 | Compound 228 (50 Å) |

Structure of the materials used in the devices are shown as below:

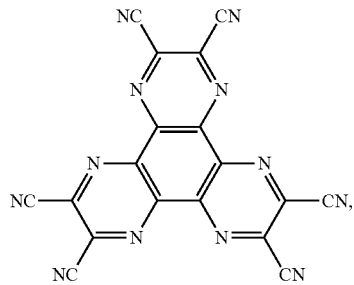

Compound HI

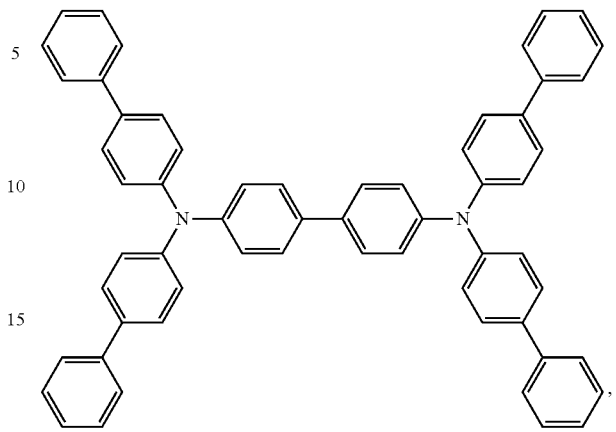

Compound HT

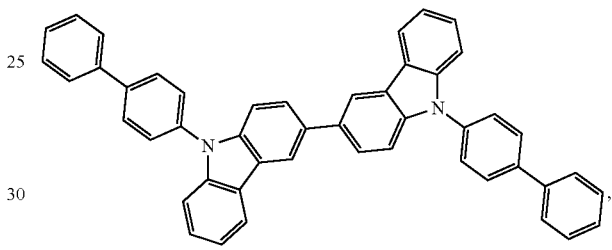

Compound EB

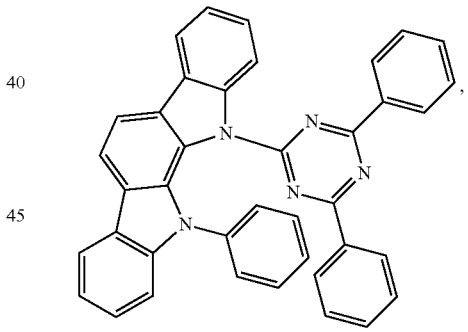

Compound HB

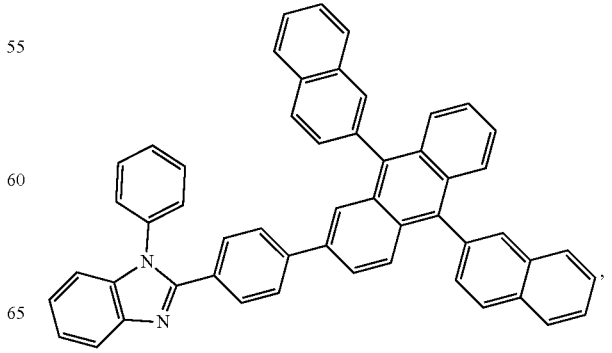

Compound ET

Compound 6

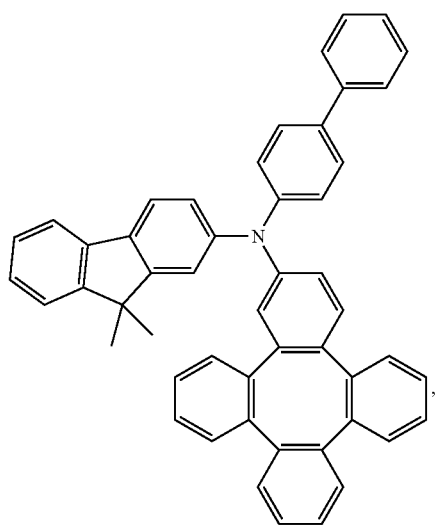

Compound 1

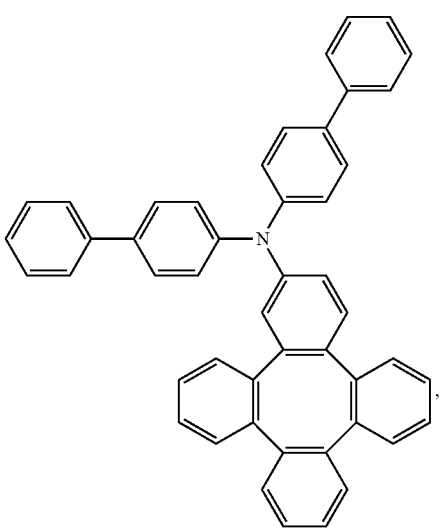

Compound 228

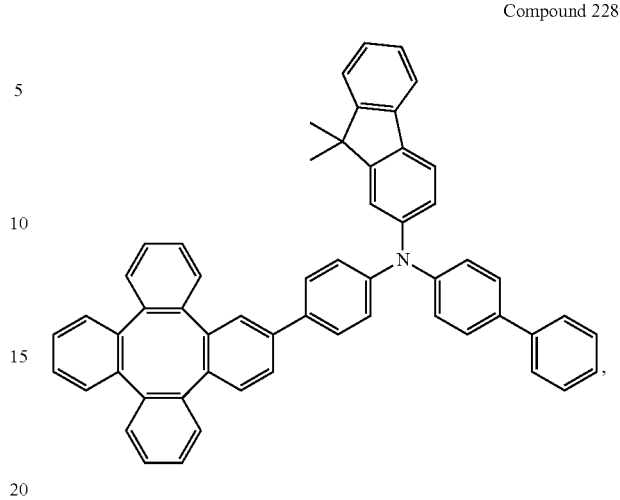

Compound GD

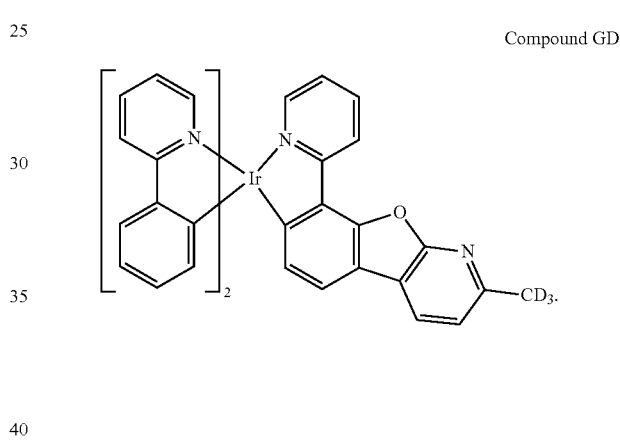

The IVL characteristics of the devices were measured at various current densities and voltages. The luminance efficiency (LE), external quantum efficiency (EQE), λmax, full width at half maximum (FWHM), voltage (V) and CIE data were measured at 1000 nits. The sublimation temperature (Sub T) of the compounds of the invention were also recorded in table 2.

TABLE 2

| Device data | | | | | | | |
|---|---|---|---|---|---|---|---|
| Device ID | Sub T (° C.) | CIE (x, y) | λmax (nm) | FWHM (nm) | Voltage (V) | LE (cd/A) | EQE (%) |
| Device Example 1 | 231 | (0.336, 0.633) | 527 | 58.5 | 2.97 | 88.19 | 22.82 |
| Device Example 2 | 234 | (0.337, 0.632) | 527 | 58.9 | 2.97 | 87.74 | 22.73 |
| Device Example 3 | 258 | (0.335, 0.633) | 526 | 58.4 | 2.98 | 87.93 | 22.74 |

DISCUSSION

The data in table 2 show that Device Examples 1-3 have high efficiencies (>22%), low voltages (<3 V). In addition, the inventive compounds have low sublimation temperatures. Therefore, the above experimental results indicate that the compounds having Formula 1 have good sublimation characters, and can offer good performances in OLED, especially as hole conducting materials and/or electron blocking materials.

It is understood that the various embodiments described herein are by way of example only, and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:

1. A hole transporting compound represented by any one of Formula 2 to Formula 5:

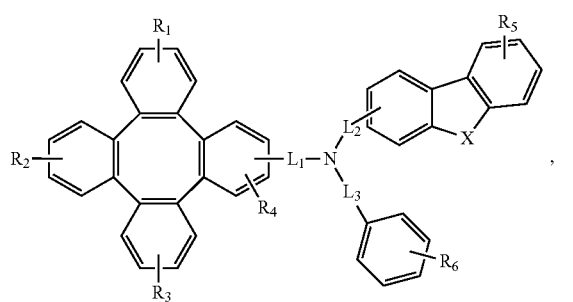

Formula 2

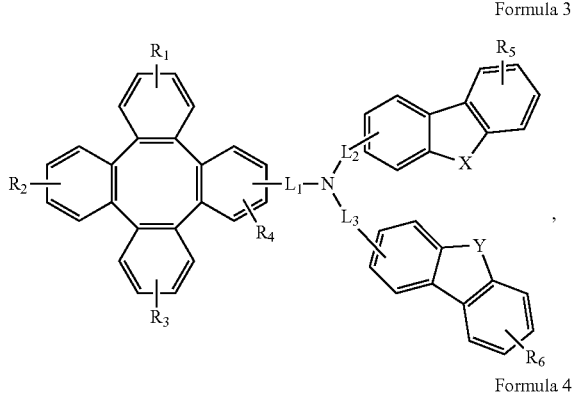

Formula 3

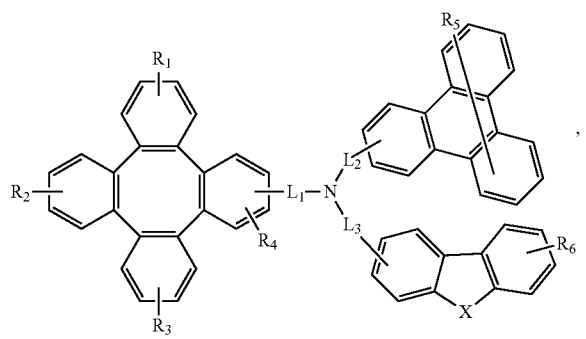

Formula 4

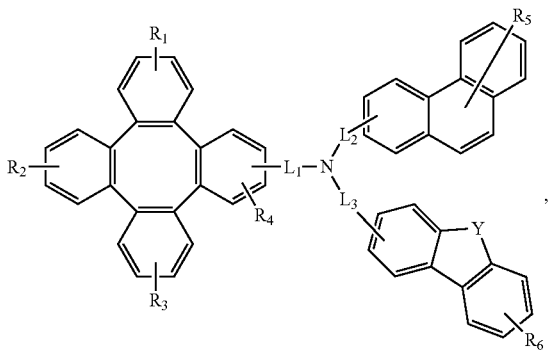

Formula 5 wherein

X and Y are each independently selected from the group consisting of O, S, Se, NR, and CR'R";

in formula 3, Y is selected from CR'R";

R, R', R", $R_1$, $R_2$, $R_3$, $R_4$, $R_5$, and $R_6$ are each independently selected from the group consisting of hydrogen, deuterium, a substituted or unsubstituted alkyl group having 1 to 20 carbon atoms, a substituted or unsubstituted cycloalkyl group having 3 to 20 ring carbon atoms, a substituted or unsubstituted arylalkyl group having 7 to 30 carbon atoms, a substituted or unsubstituted alkenyl group having 2 to 20 carbon atoms, a substituted or unsubstituted aryl group having 6 to 30 carbon atoms, and combinations thereof; the alkyl group, cycloalkyl group, arylalkyl group, alkenyl group, and aryl group being unsubstituted or substituted with one or more substituents selected from the group consisting of deuterium, halogen, alkyl, cycloalkyl, arylalkyl, alkoxy, aryloxy, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof;

$L_1$, selected from the group consisting of a single bond, an arylene group having 6 to 30 ring carbon atoms, a heteroarylene group having 5 to 30 ring atoms, and combinations thereof;

wherein $L_2$ and $L_3$ are each independently selected from the group consisting of:

Single bond

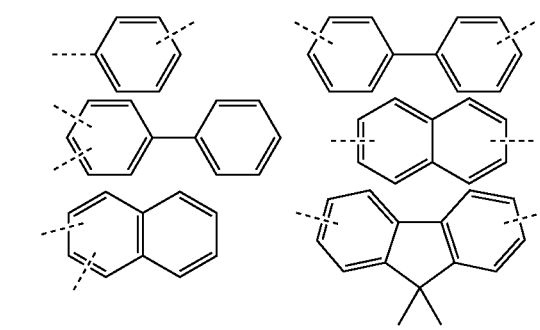

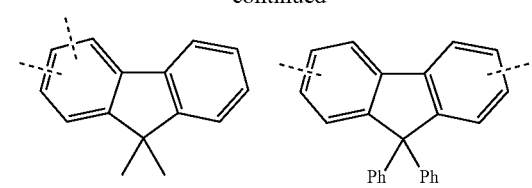
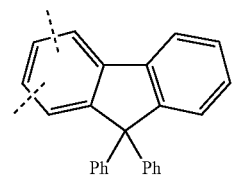
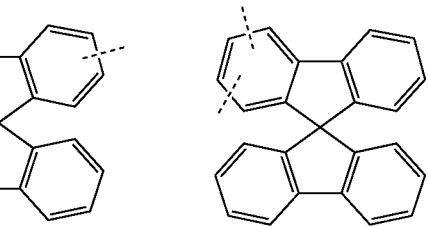
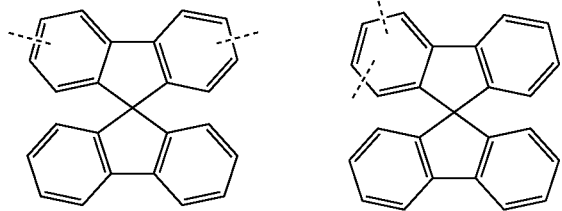
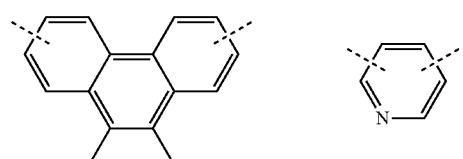
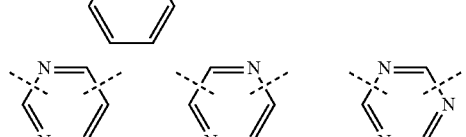
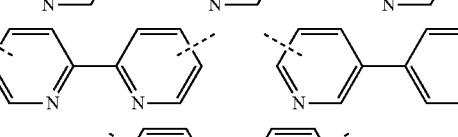
and combinations thereof.
2. The hole transporting compound of claim 1, wherein $L_1$ is selected from the group consisting of:
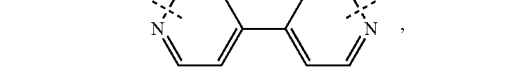
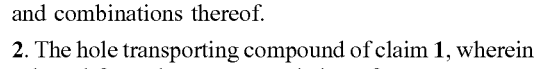
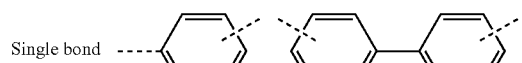
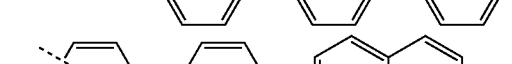
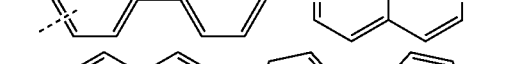
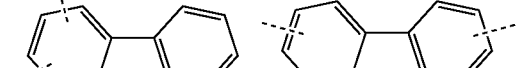
and combinations thereof.
3. The hole transporting compound of claim 1, wherein $L_1$, $L_2$ and $L_3$ are each independently selected from single bond or phenylene.

4. The hole transporting compound of claim 1, wherein the compound is selected from the group consisting of:
Compound 6
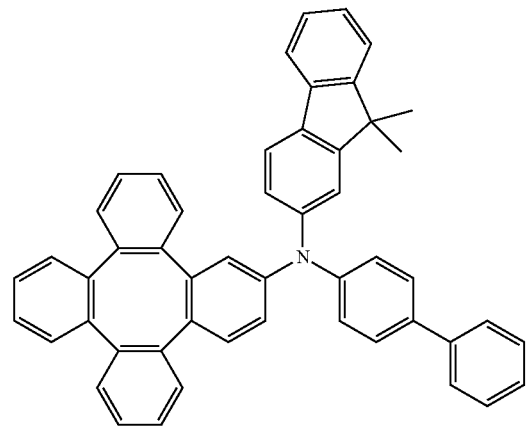
Compound 7
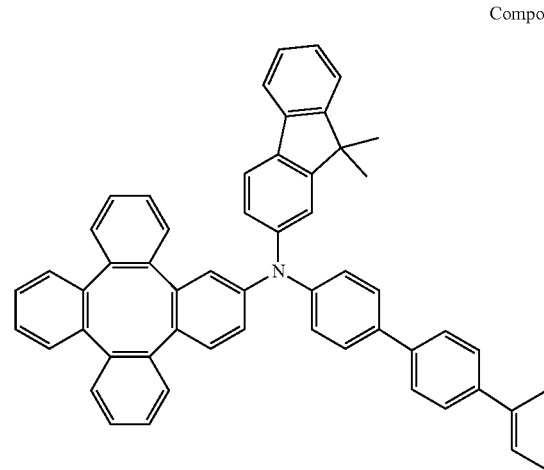
Compound 8
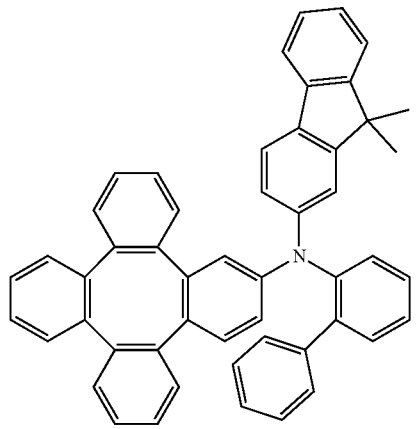
-continued
Compound 9
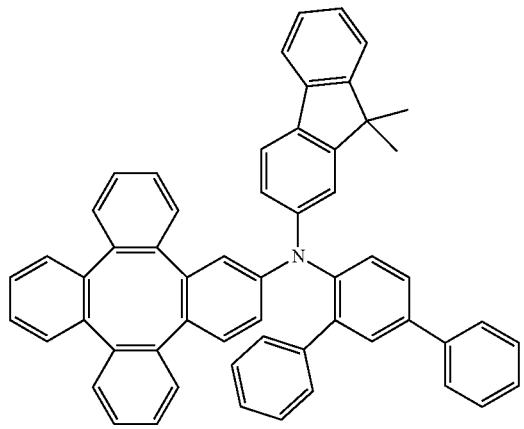
Compound 10
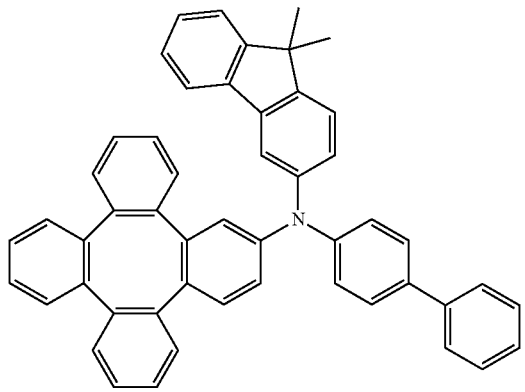
Compound 11
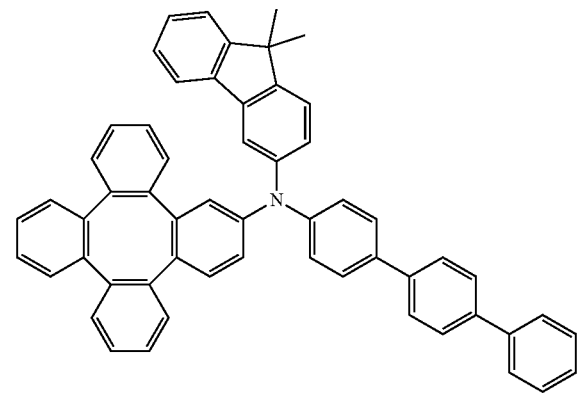

Compound 12
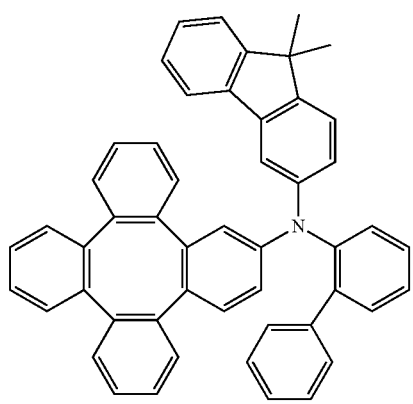
Compound 15
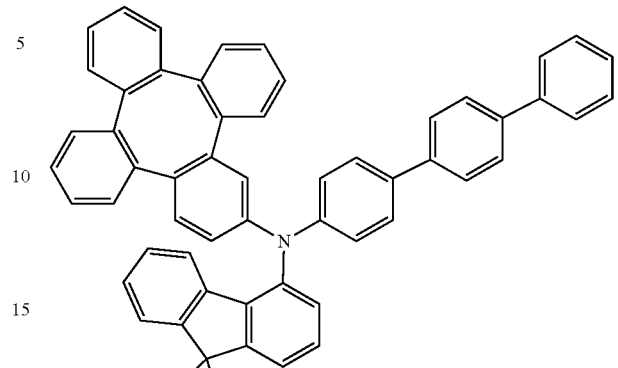
Compound 13
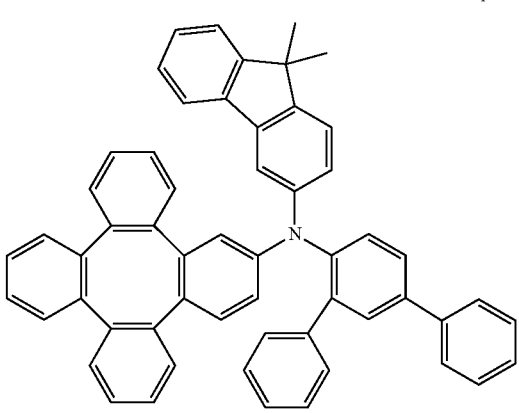
Compound 16
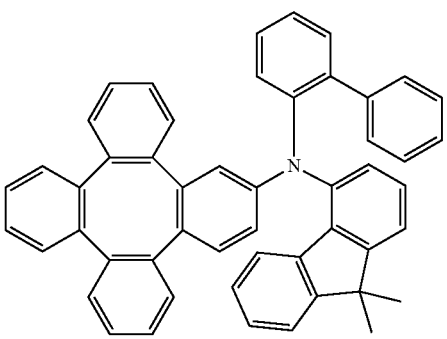
Compound 14
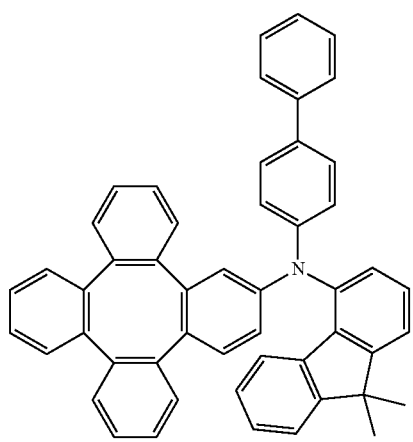
Compound 17
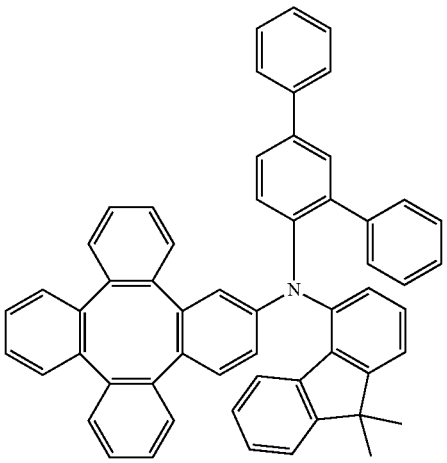

Compound 18
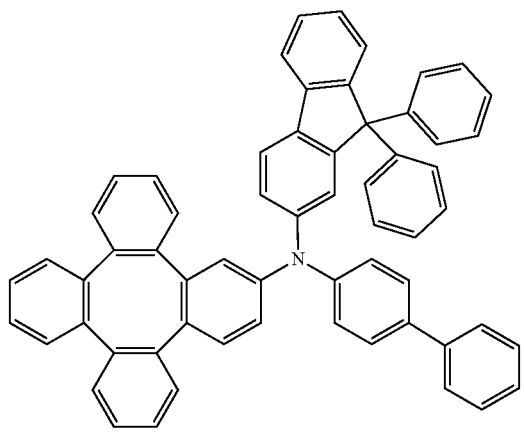
Compound 19
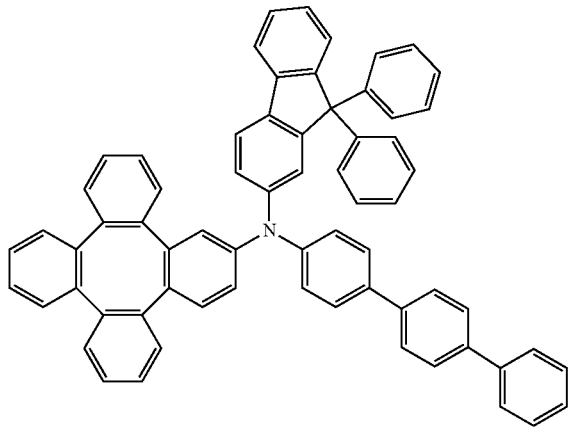
Compound 20
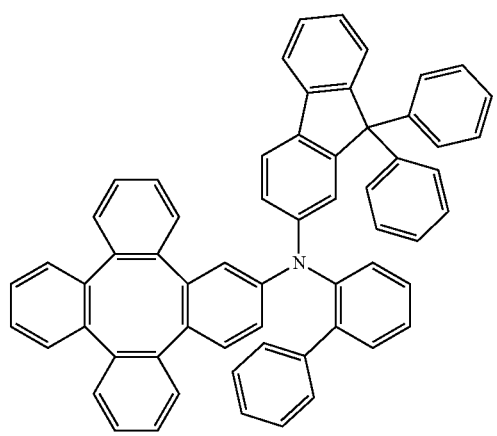
Compound 21
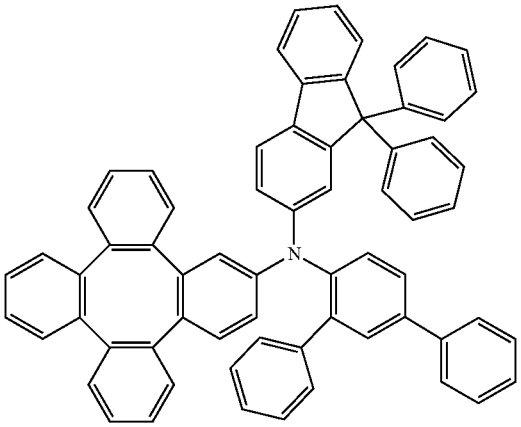
Compound 22
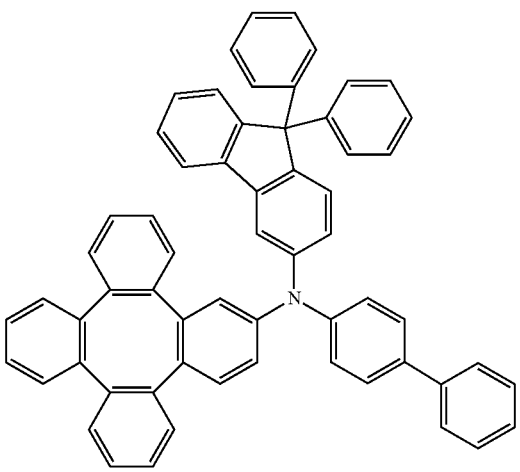
Compound 23
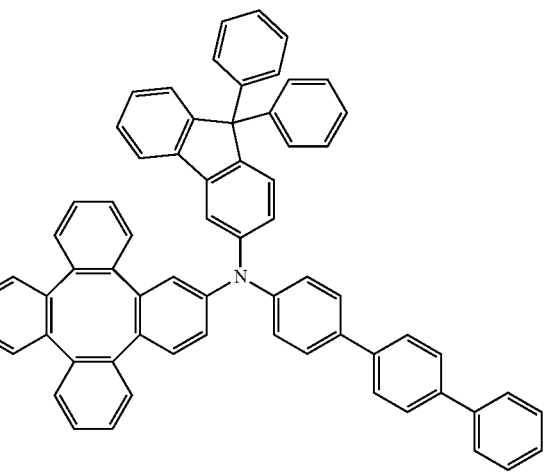

Compound 24
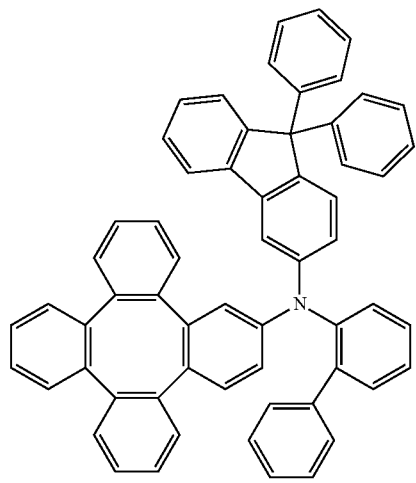
Compound 27
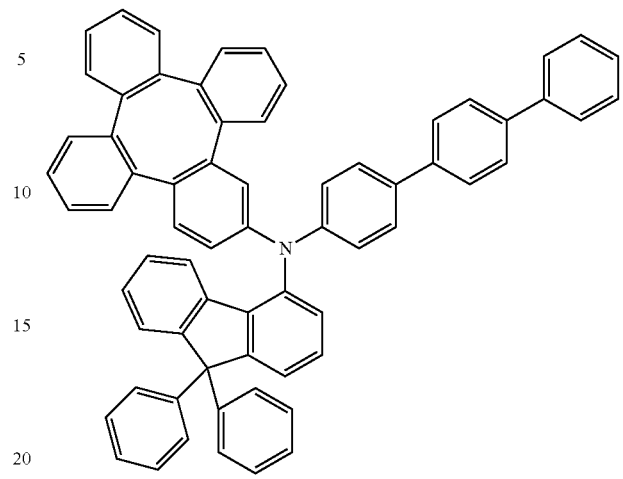
Compound 25
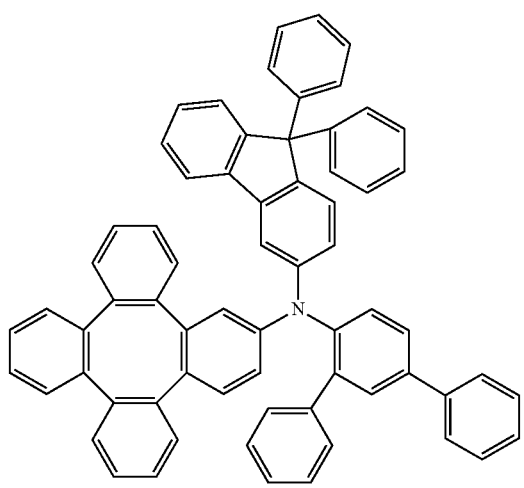
Compound 28
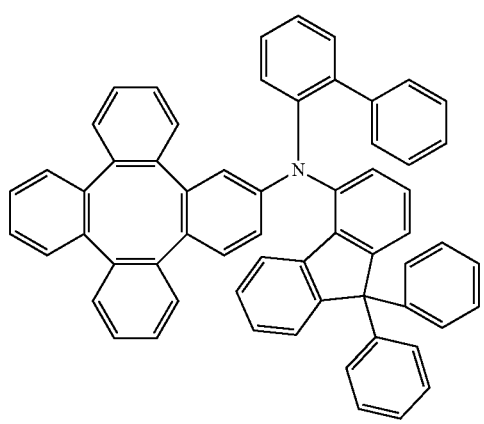
Compound 26
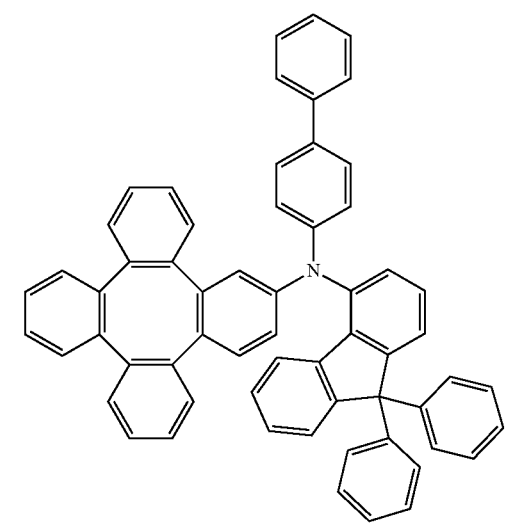
Compound 29
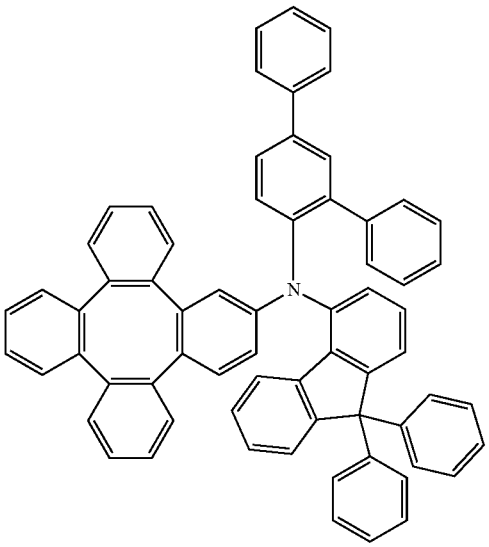

Compound 42
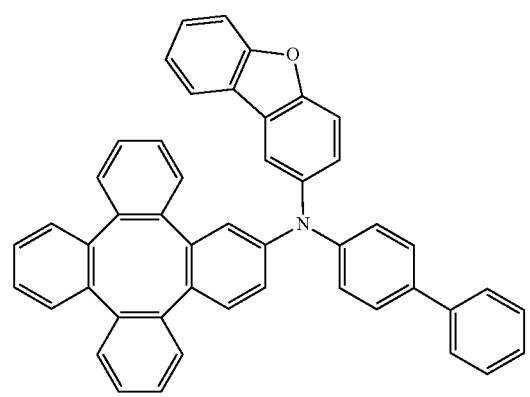
Compound 43
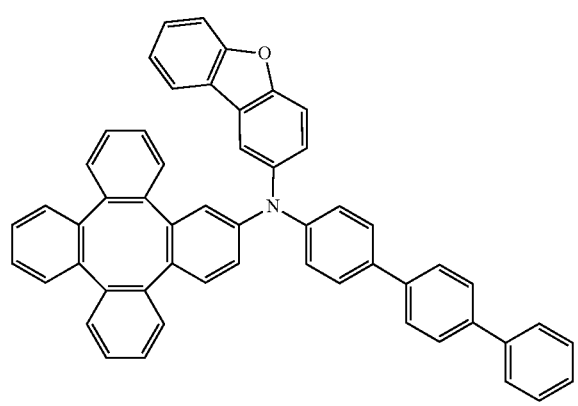
Compound 44
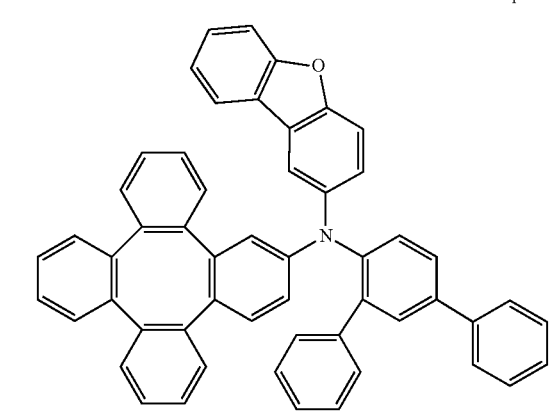
Compound 45
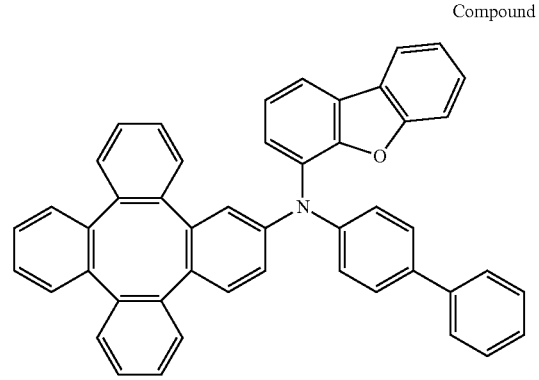
Compound 46
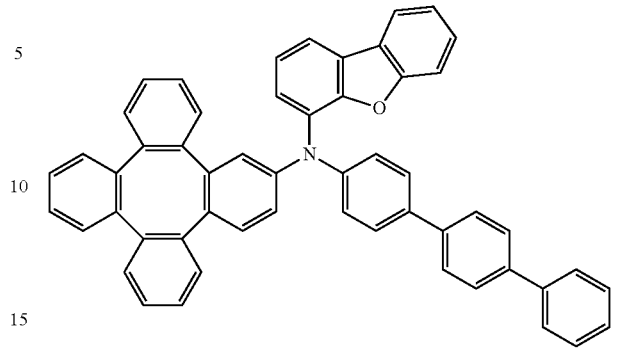
Compound 47
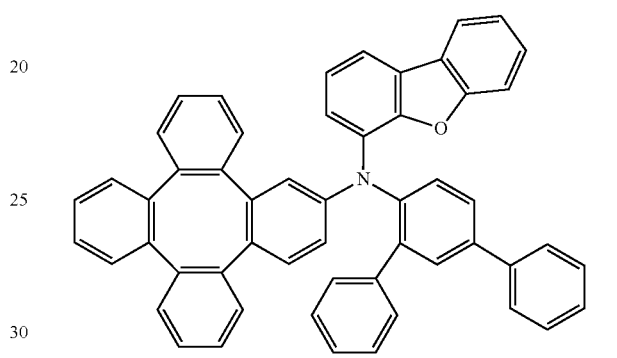
Compound 48
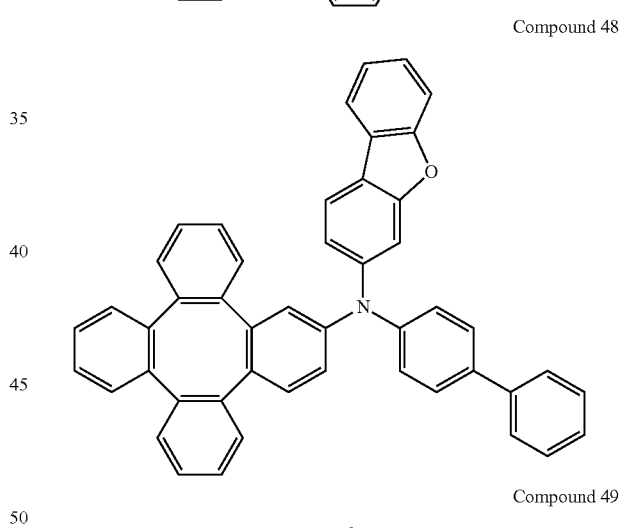
Compound 49
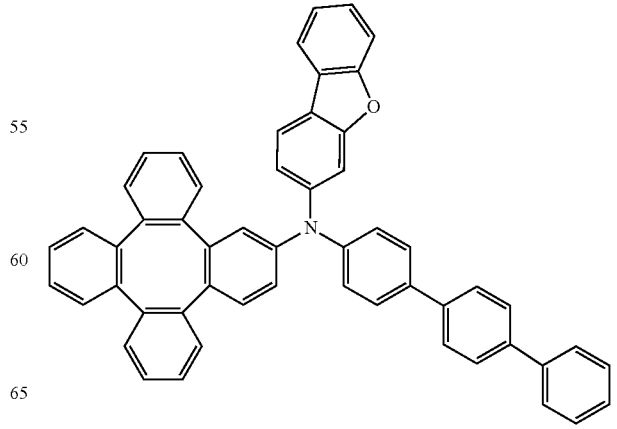

-continued
Compound 50
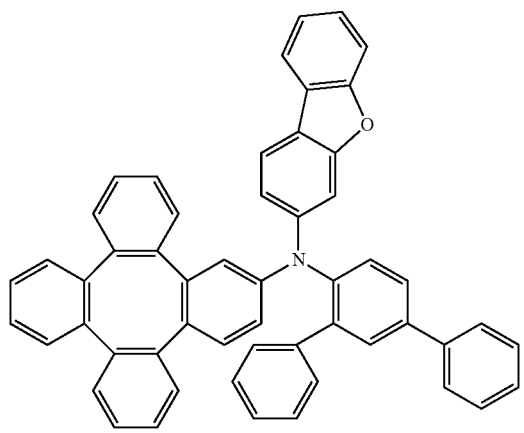
Compound 51
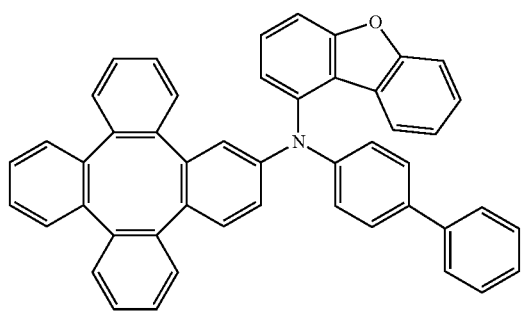
Compound 52
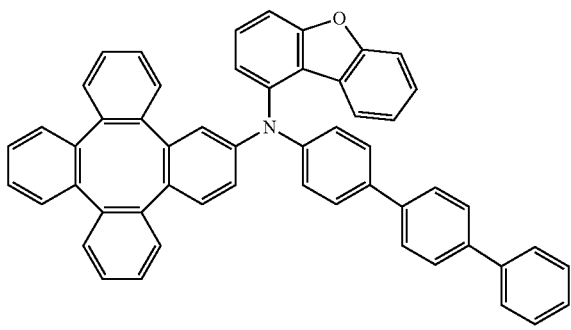
Compound 53
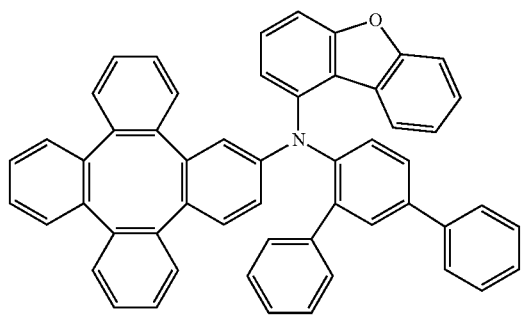
-continued
Compound 54
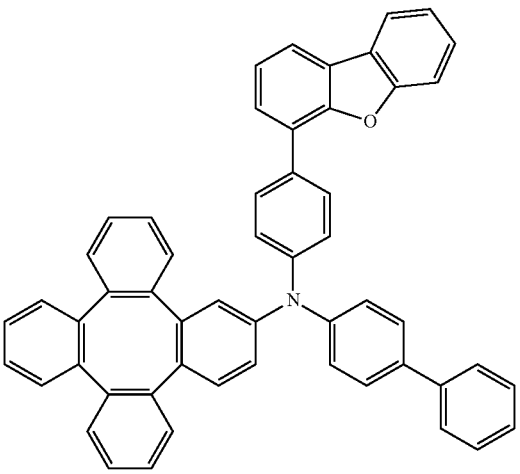
Compound 55
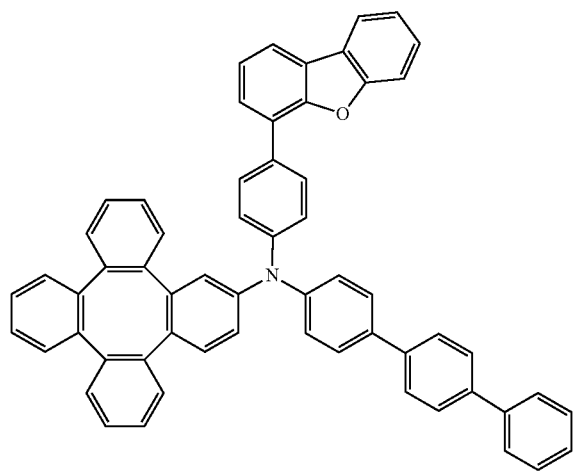
Compound 56
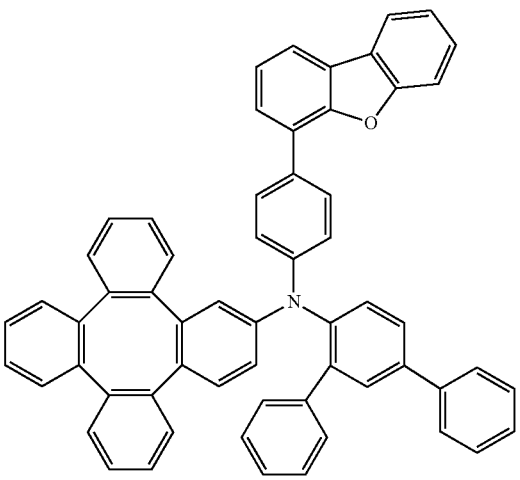

Compound 57
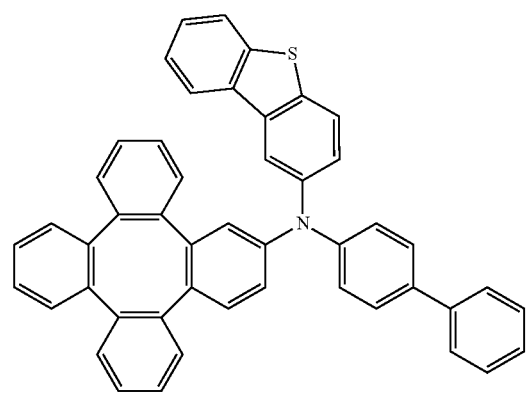
Compound 58
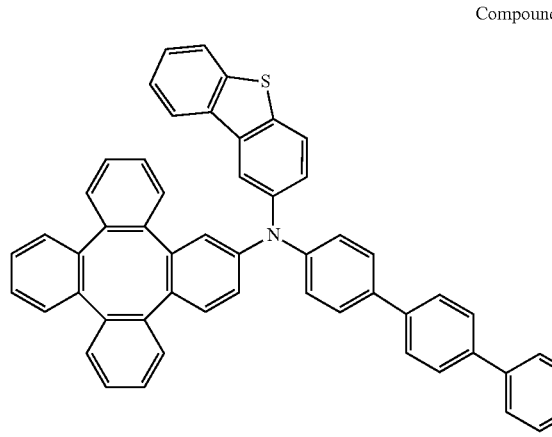
Compound 59
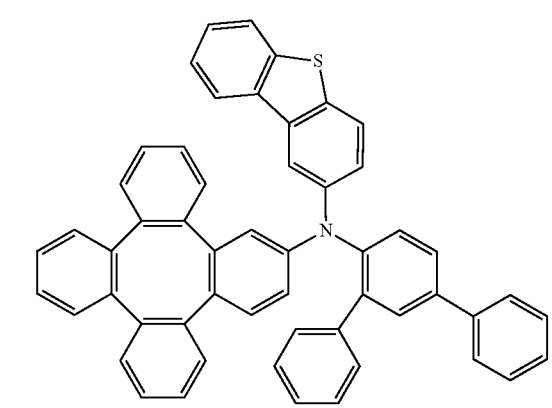
Compound 60
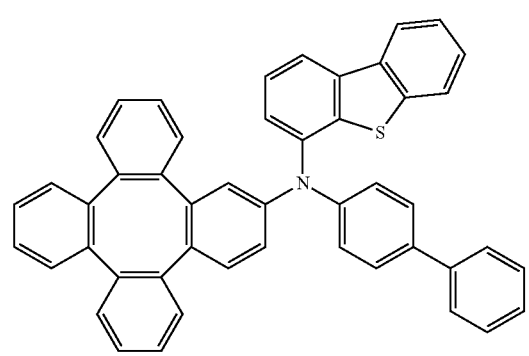
Compound 61
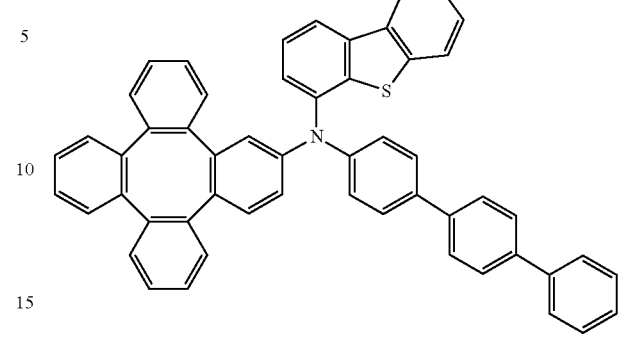
Compound 62
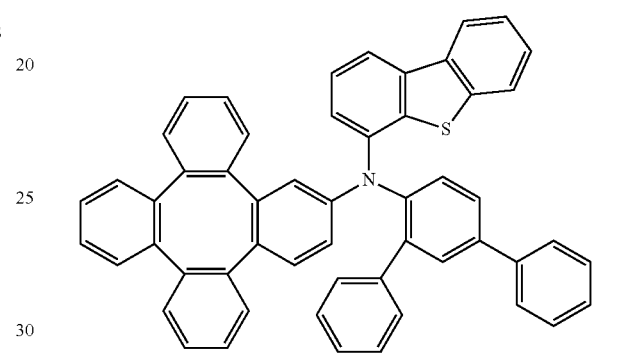
Compound 63
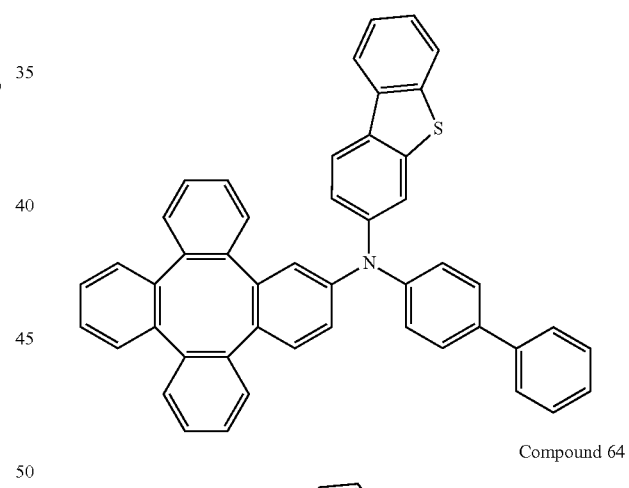
Compound 64
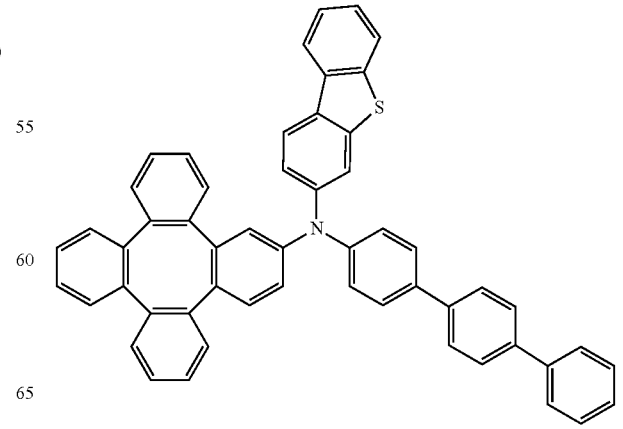

-continued
Compound 65
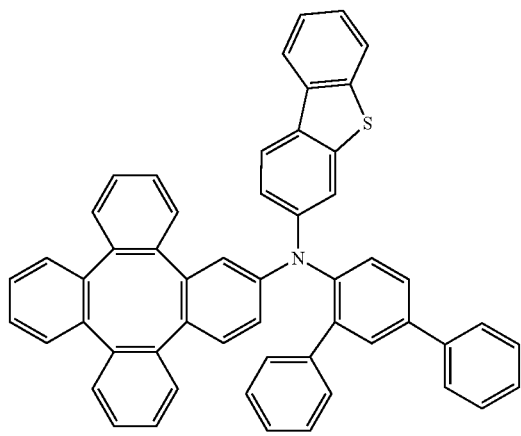
Compound 66
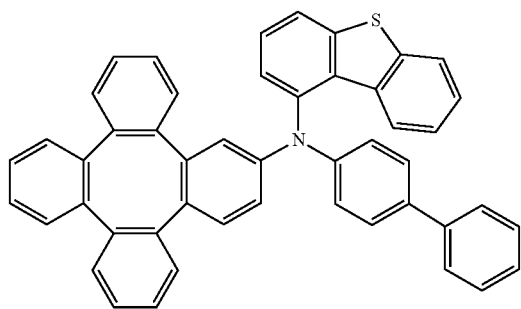
Compound 67
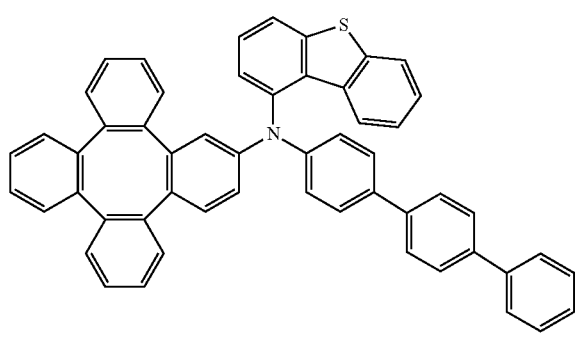
Compound 68
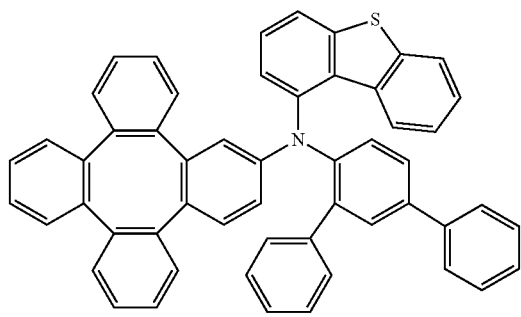
-continued
Compound 69
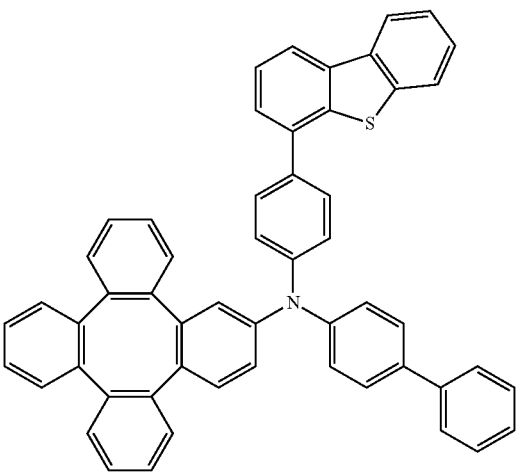
Compound 70
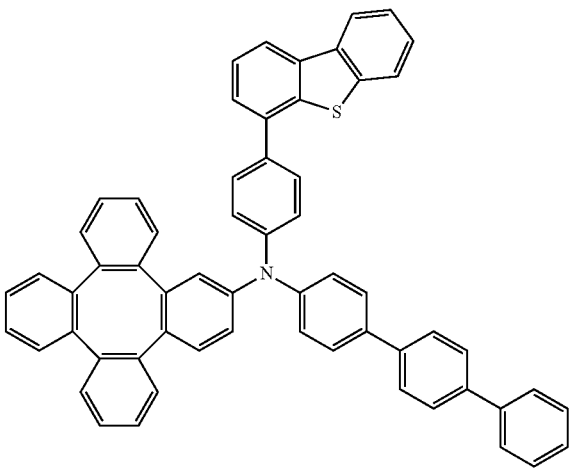
Compound 71
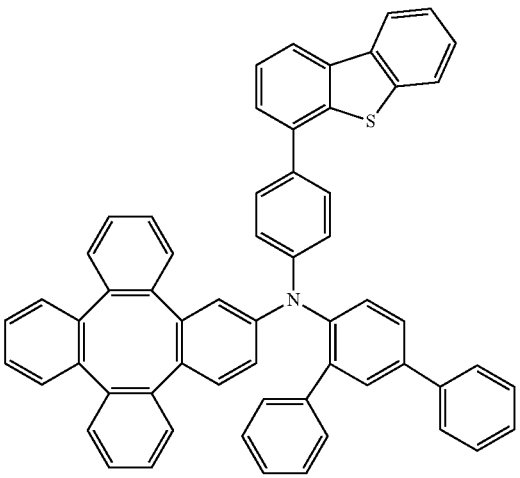

Compound 90
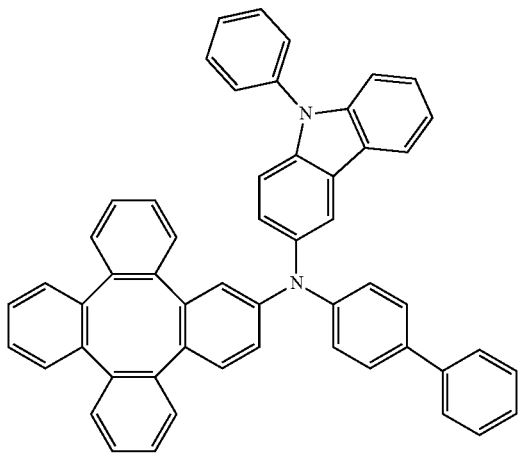
Compound 91
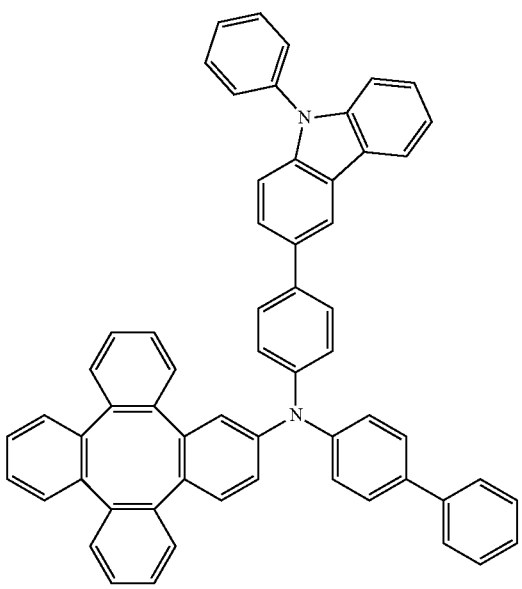
Compound 92
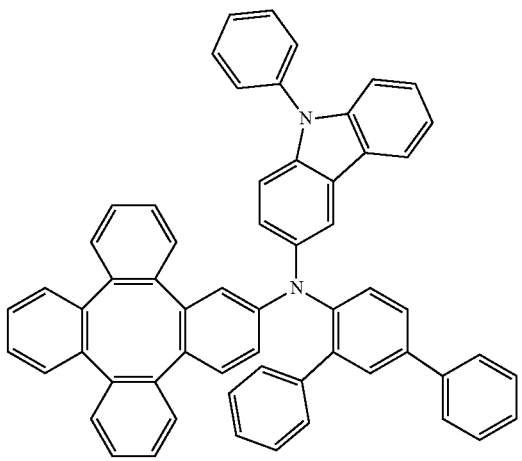
Compound 93
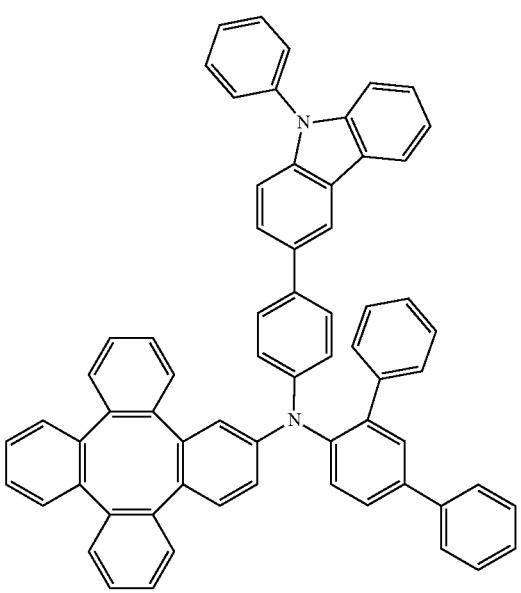
Compound 94
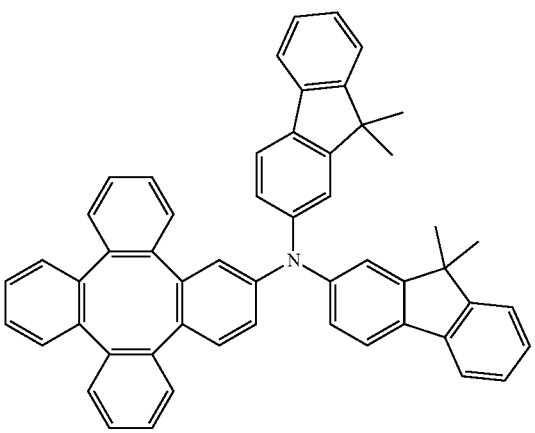
Compound 95
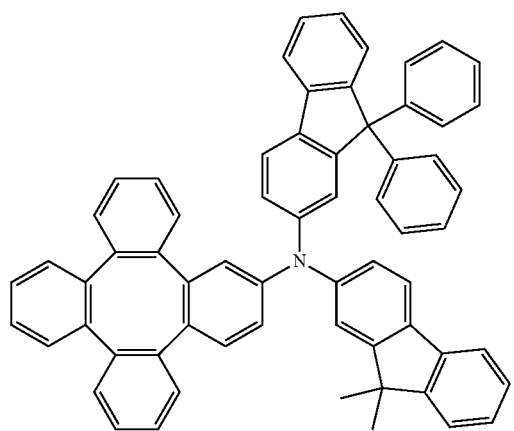

Compound 100
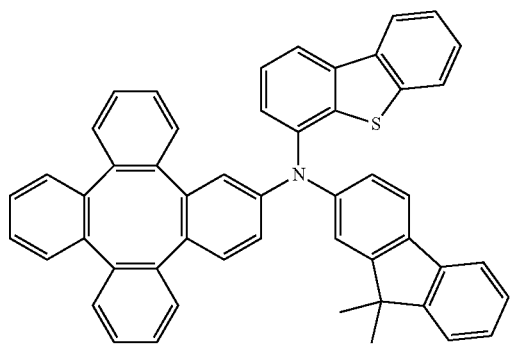
Compound 101
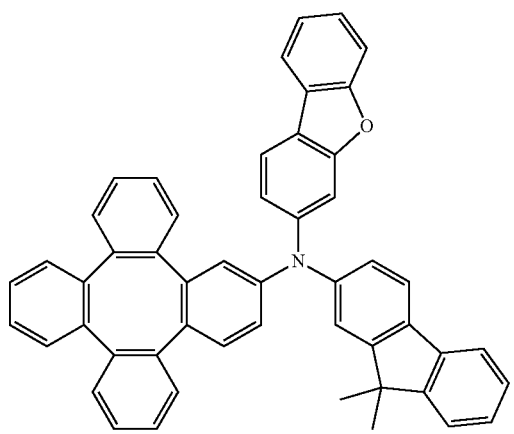
Compound 102
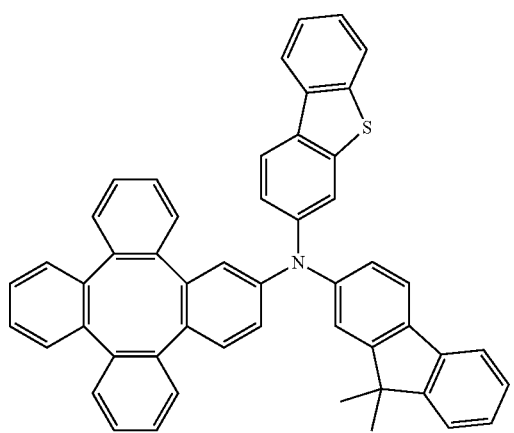
Compound 97
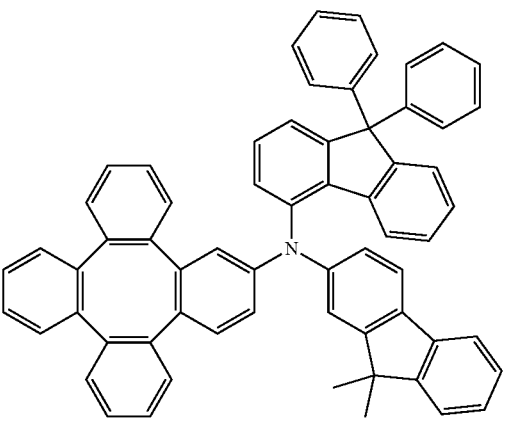
Compound 99
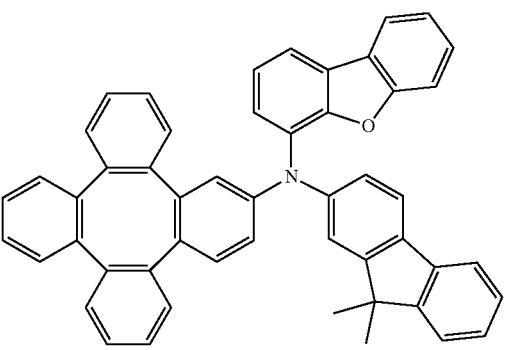
Compound 103
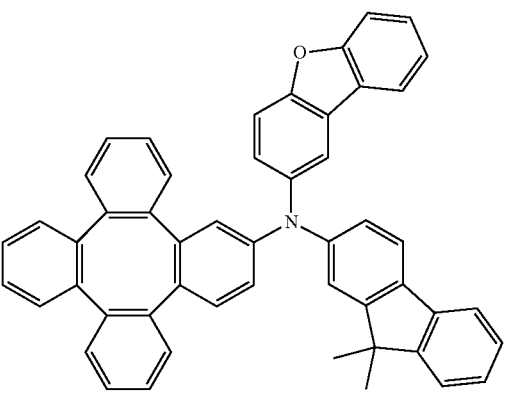
Compound 104

Compound 105
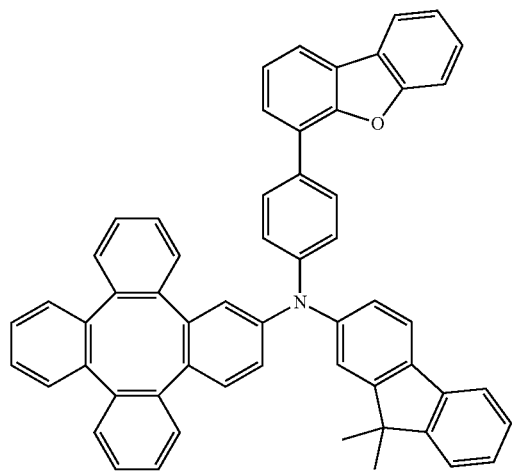
Compound 106
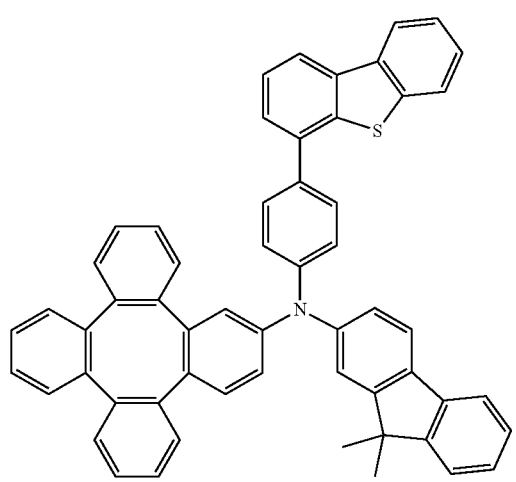
Compound 109
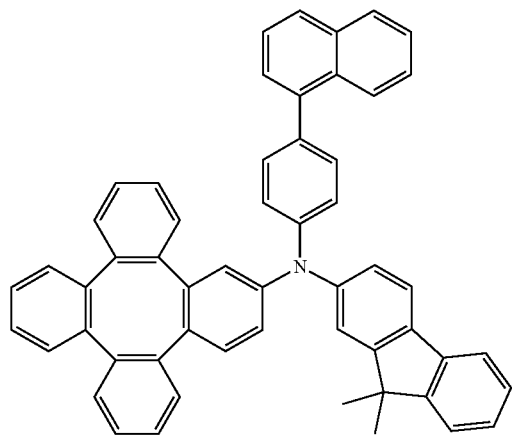
Compound 110
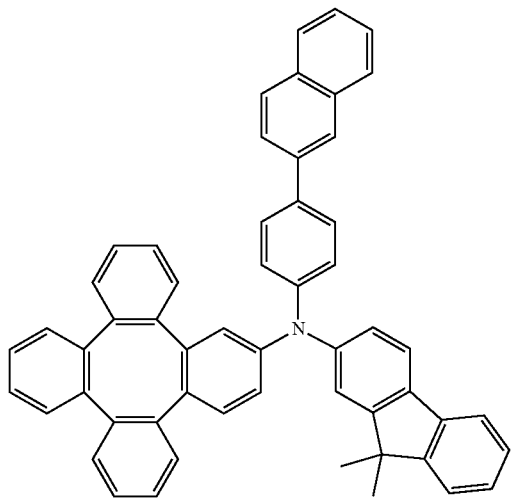
Compound 112
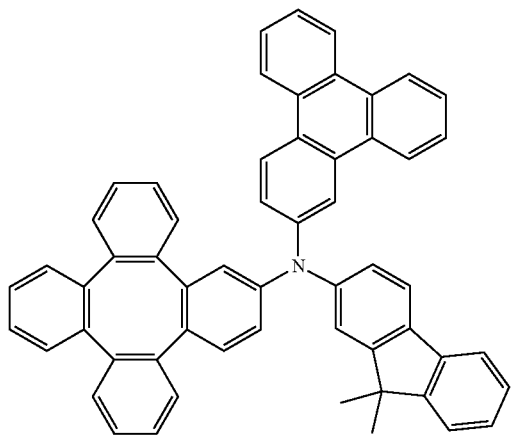
Compound 113
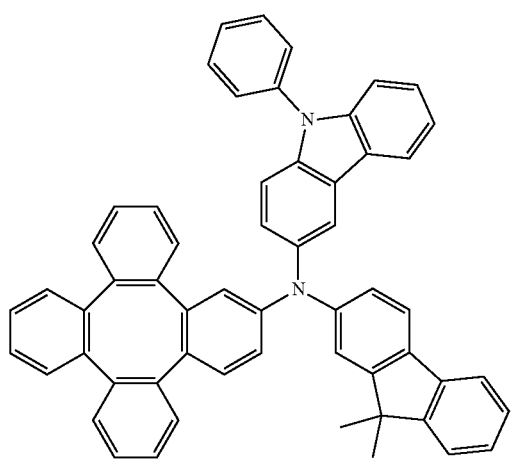

Compound 114
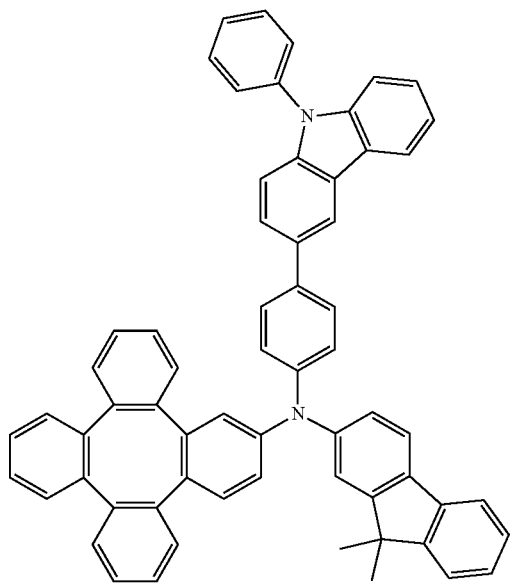
Compound 115
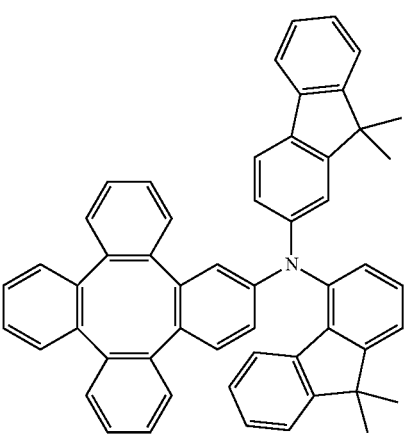
Compound 116
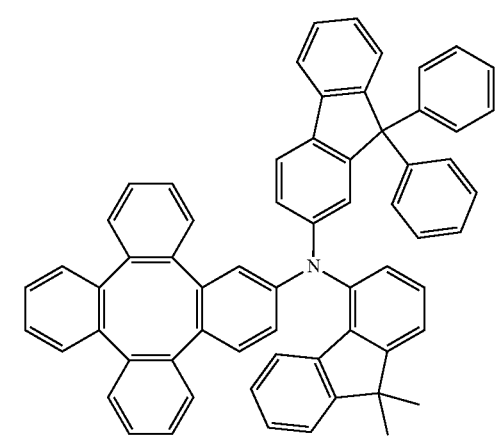
Compound 118
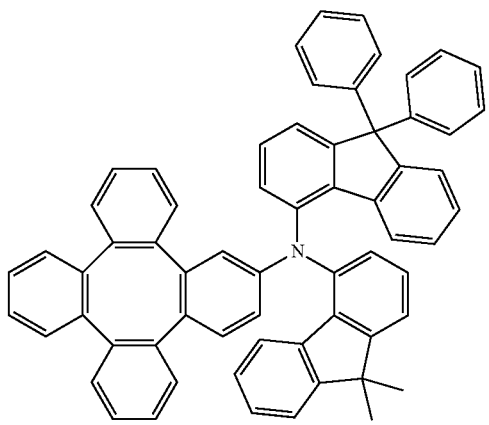
Compound 120
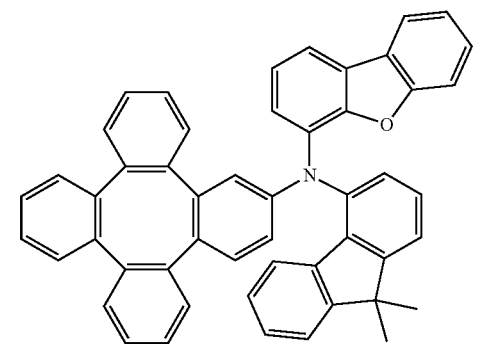
Compound 121
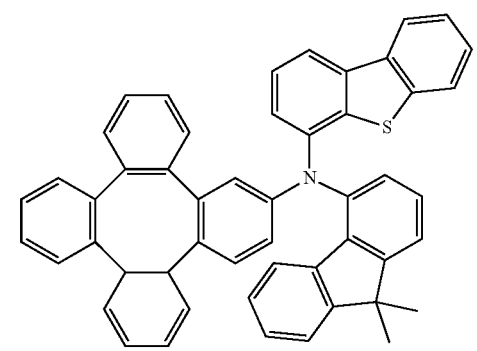
Compound 122
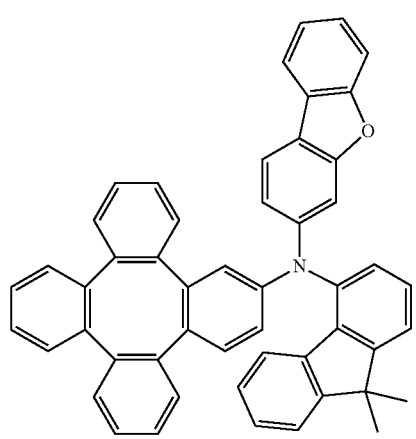

Compound 123
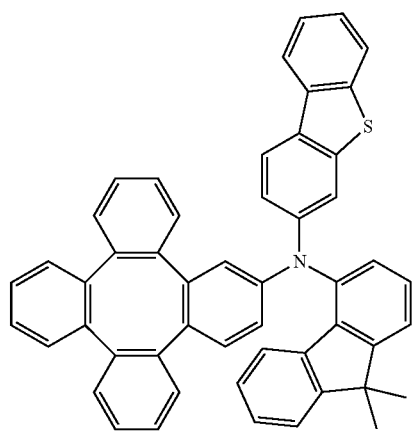
Compound 124
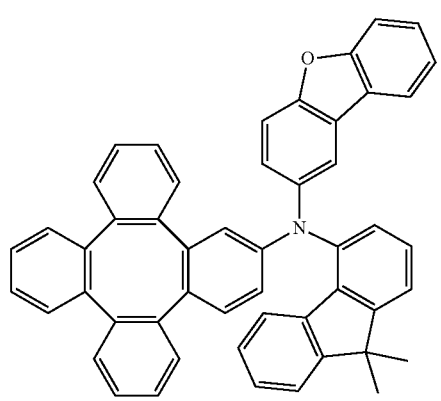
Compound 125
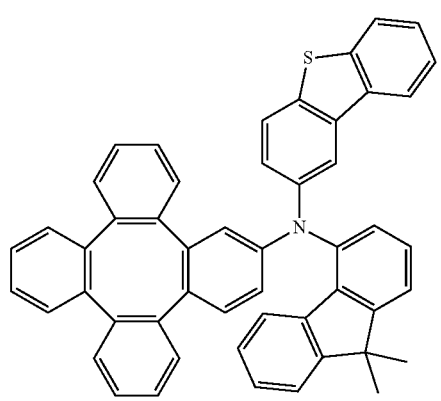
Compound 126
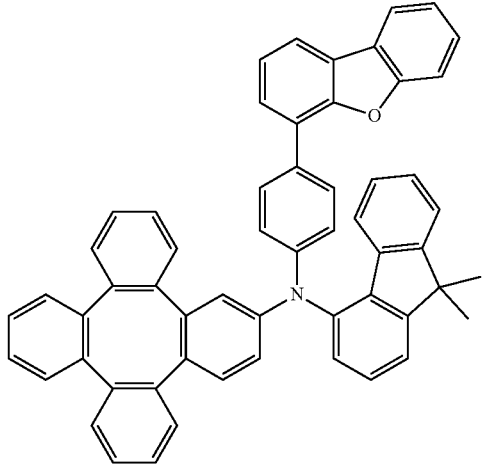
Compound 127
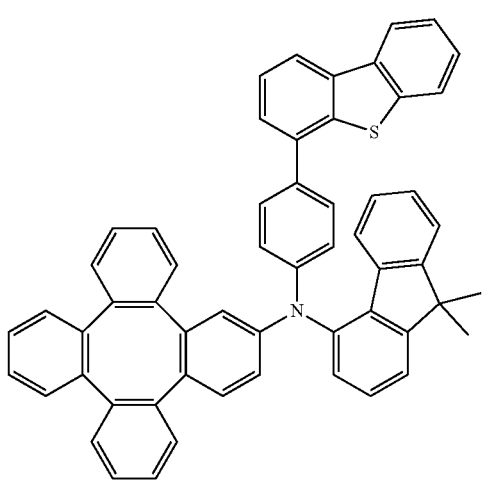
Compound 130
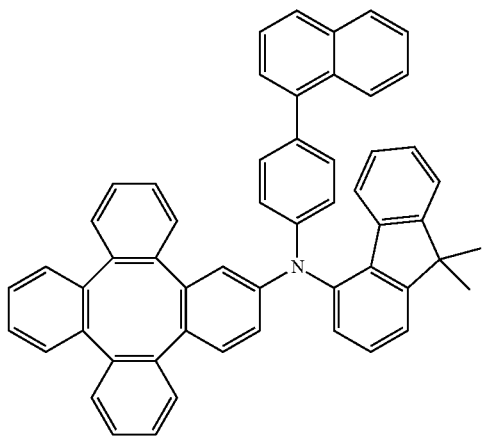

Compound 131
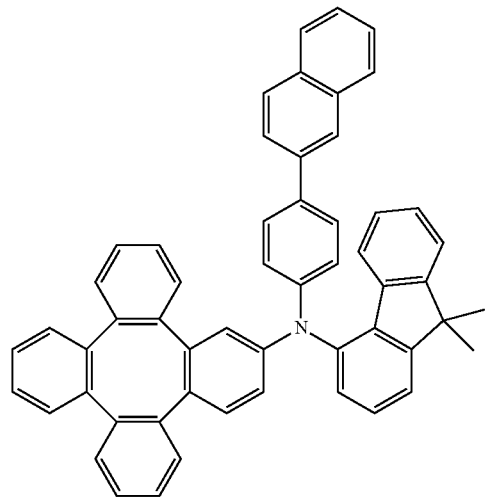
Compound 133
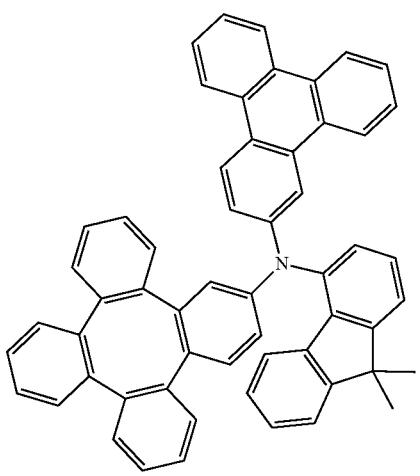
Compound 134
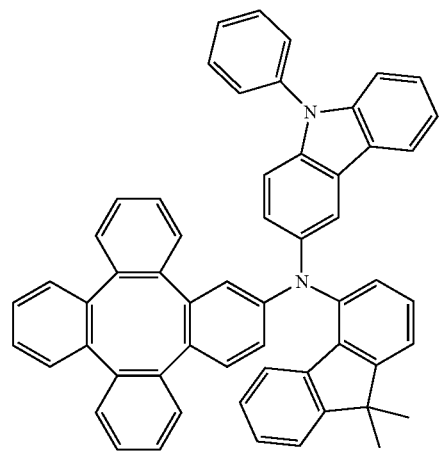
Compound 135
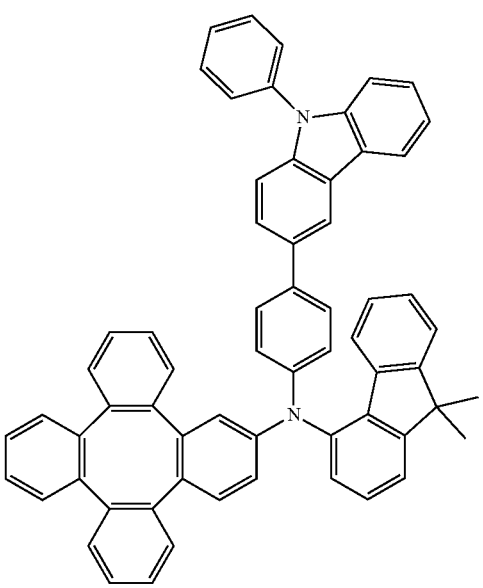
Compound 137
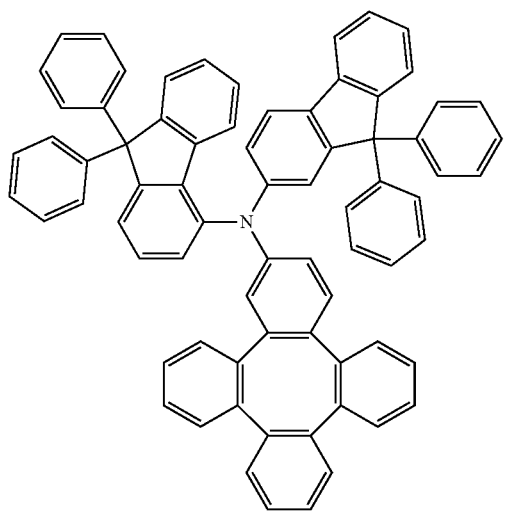
Compound 139
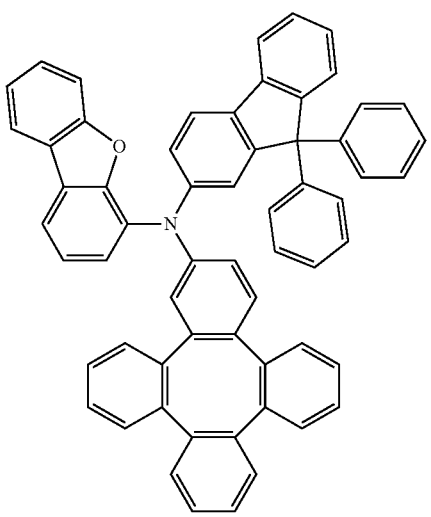

Compound 140
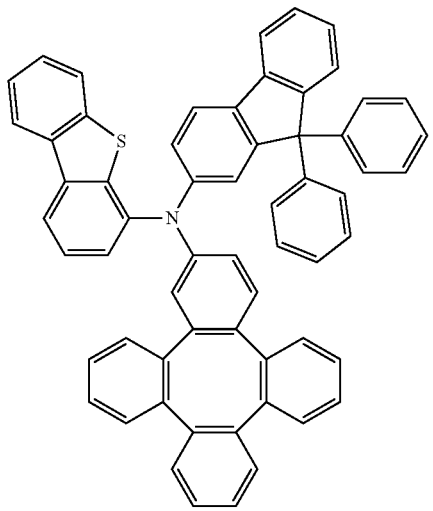
Compound 141
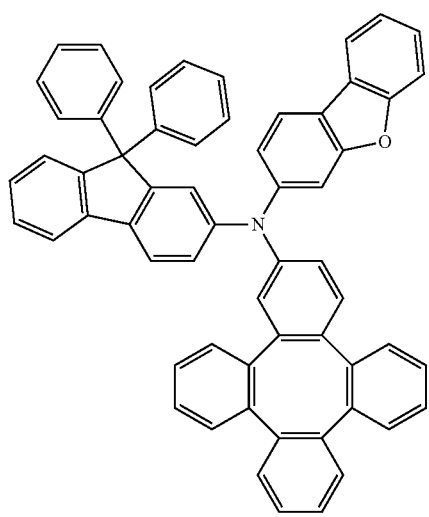
Compound 142
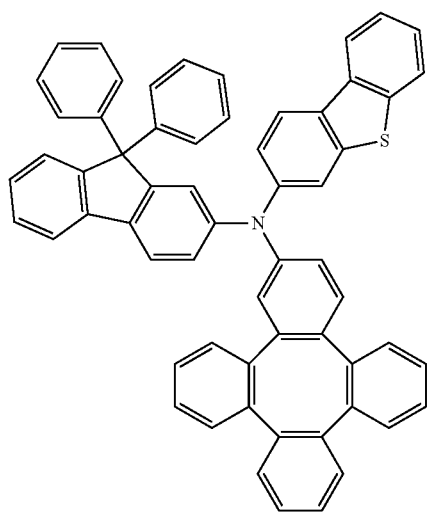
Compound 143
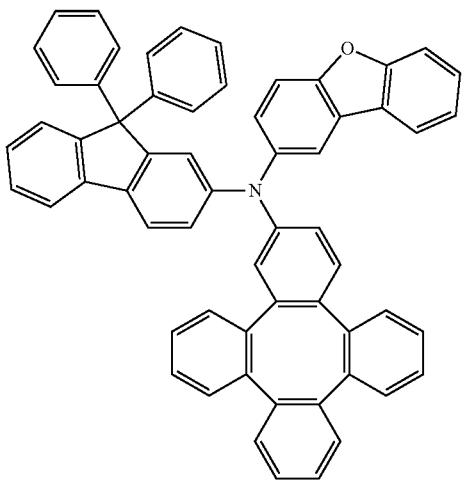
Compound 144
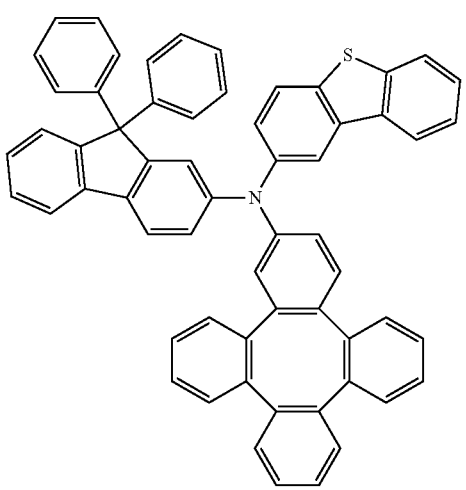
Compound 145
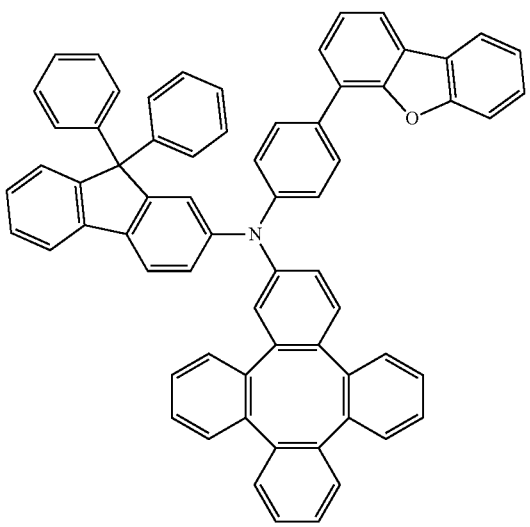

Compound 146
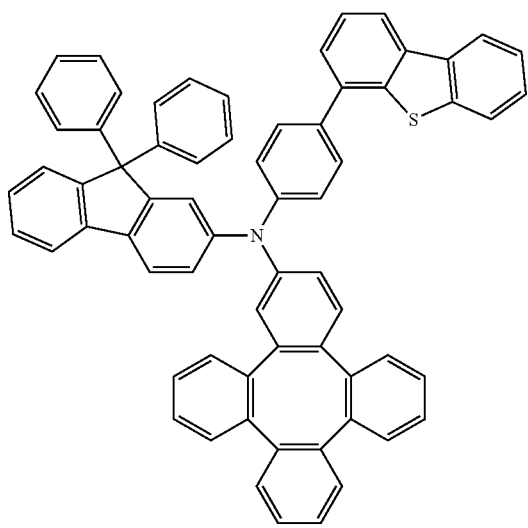
Compound 149
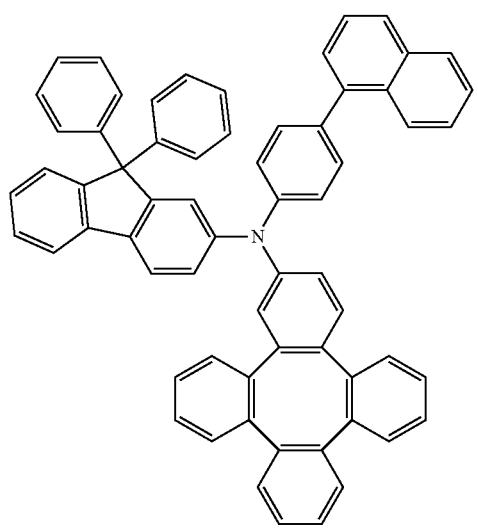
Compound 150
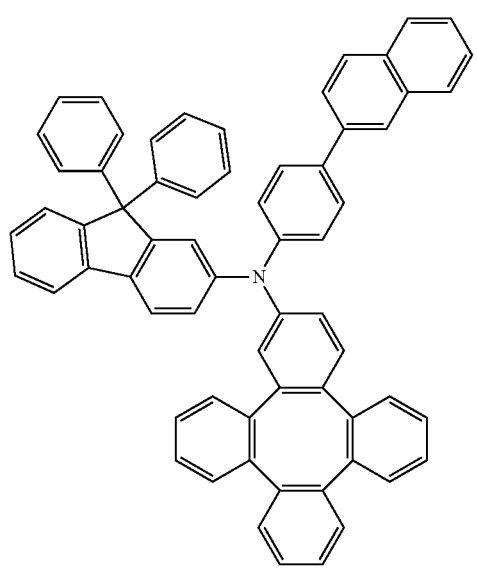
Compound 152
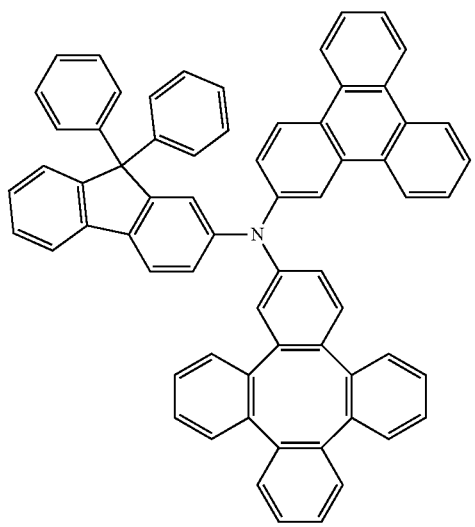
Compound 154
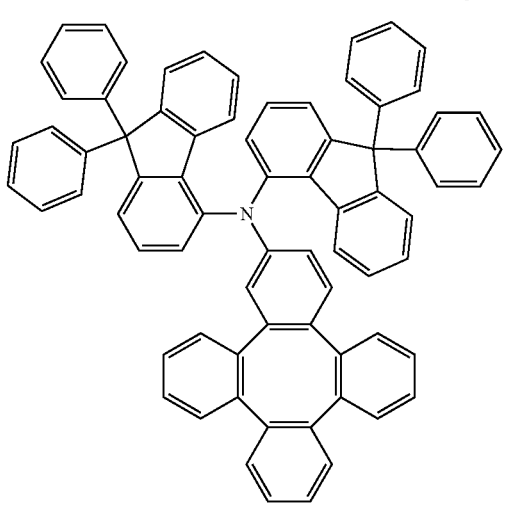
Compound 156
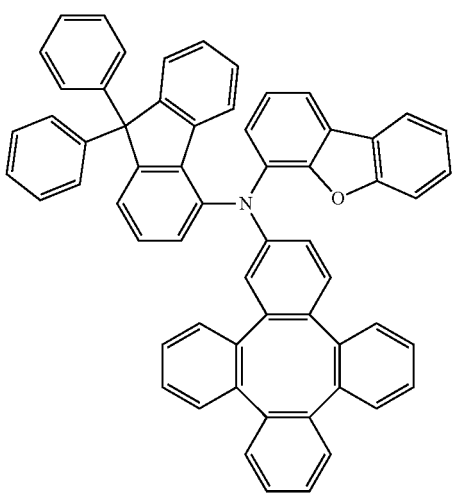

Compound 157
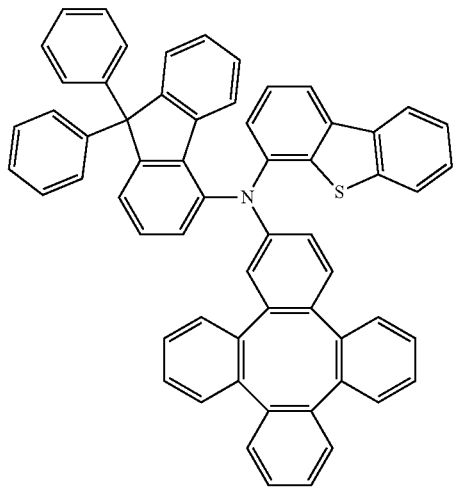
Compound 157
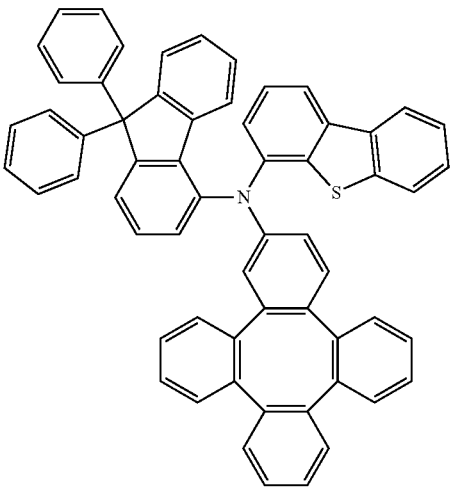
Compound 158
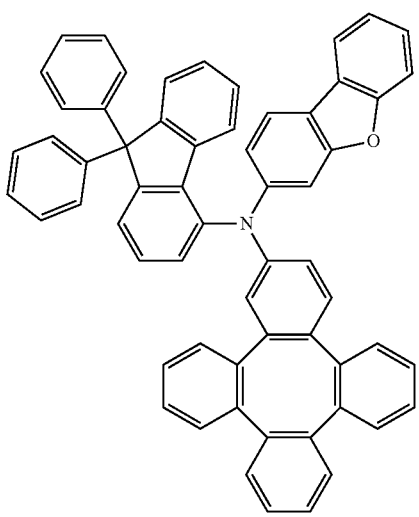
Compound 158
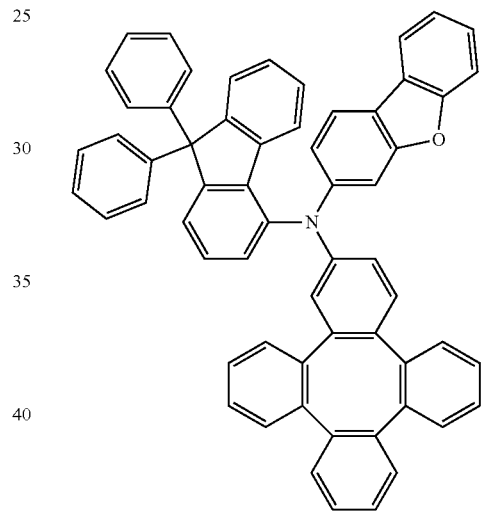
Compound 159
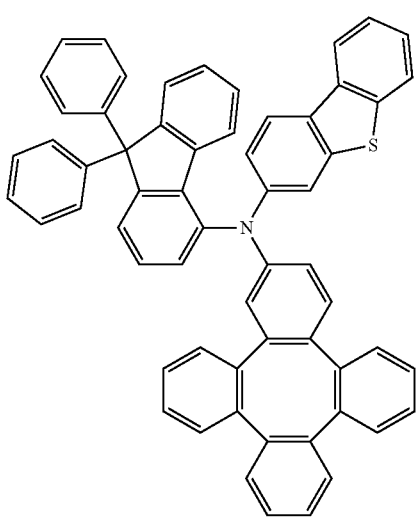
Compound 159
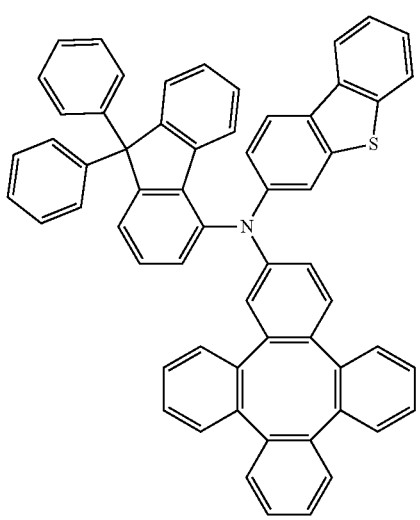

Compound 160
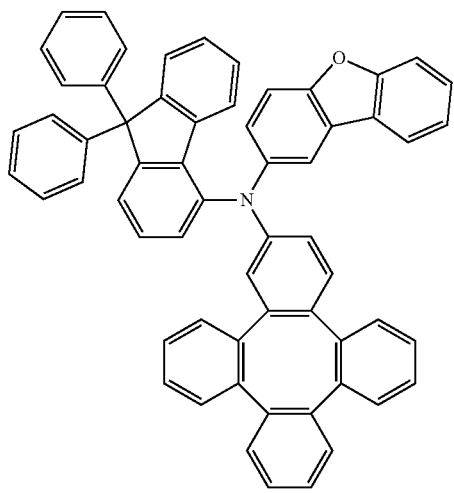
Compound 161
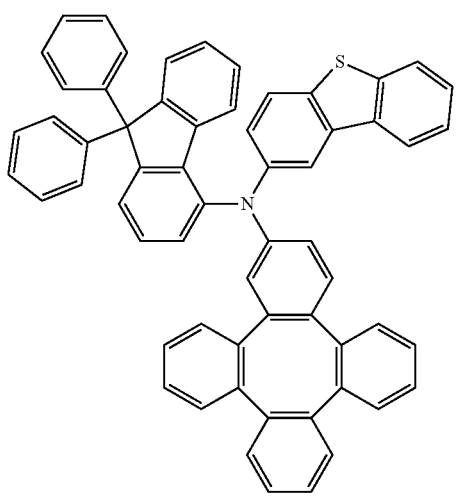
Compound 162
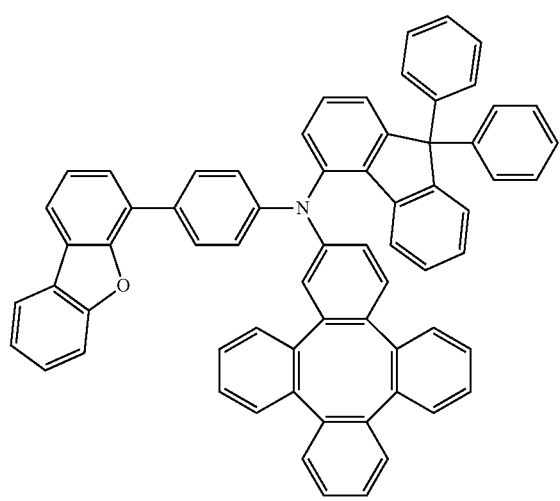
Compound 163
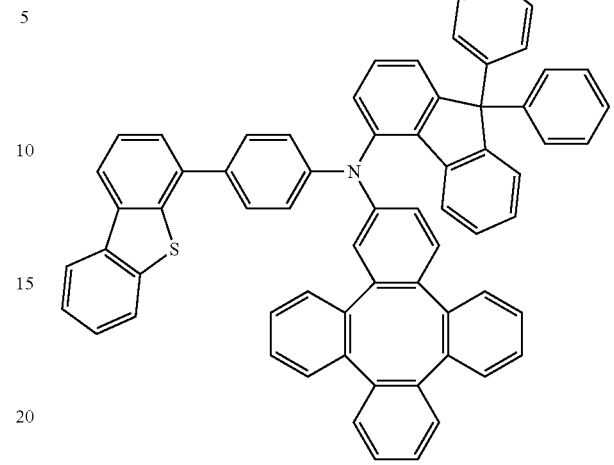
Compound 166
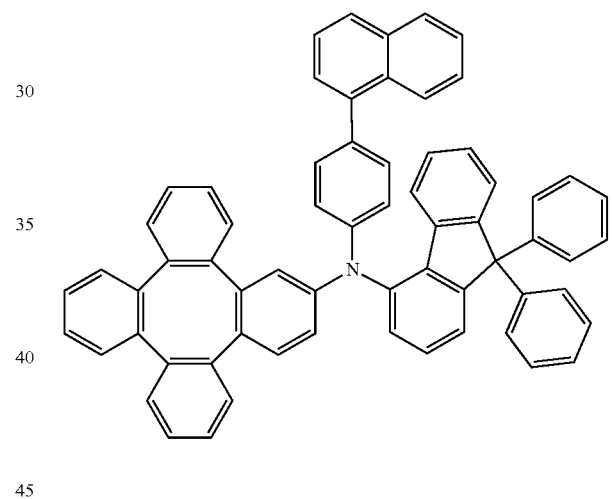
Compound 167
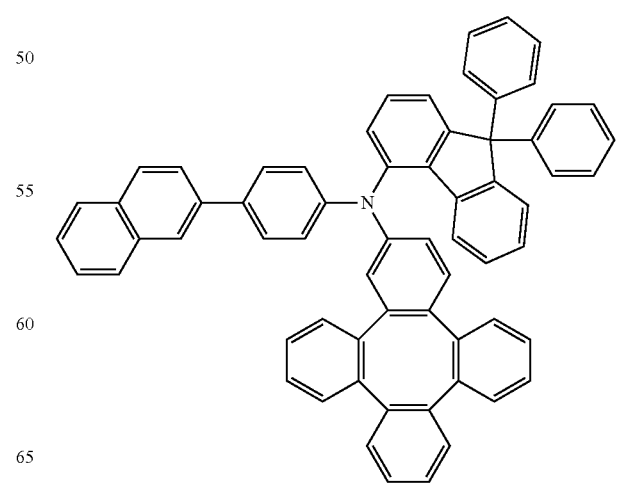

Compound 169
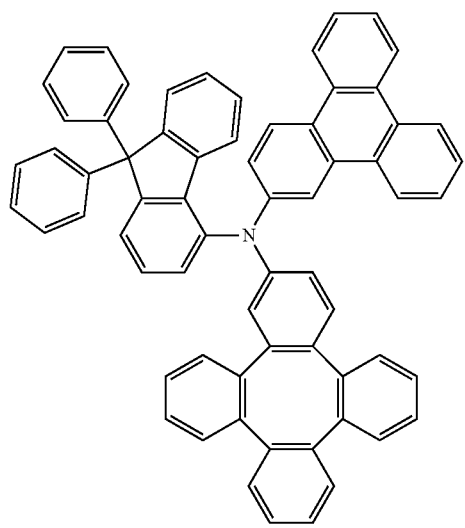
Compound 206
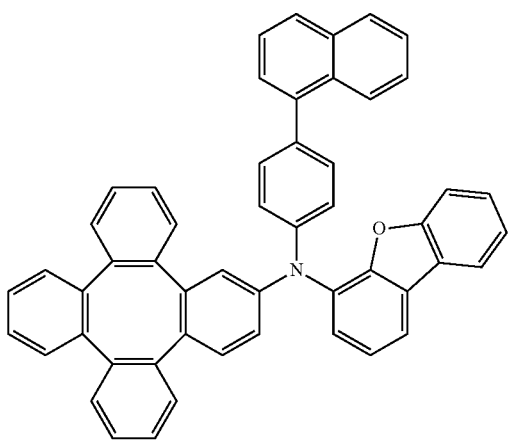
Compound 170
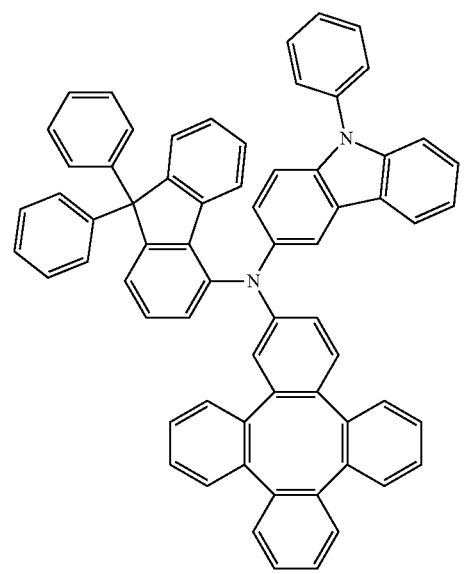
Compound 207
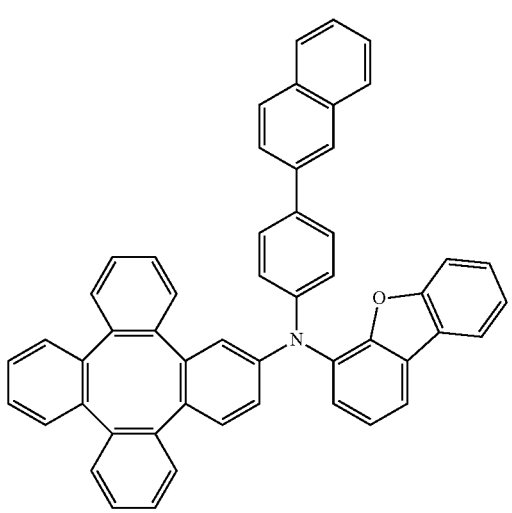
Compound 205
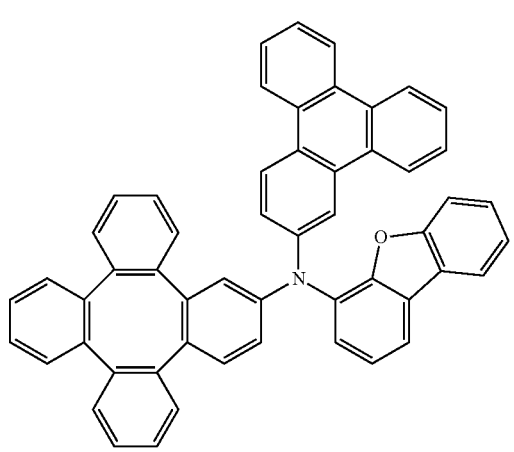
Compound 208
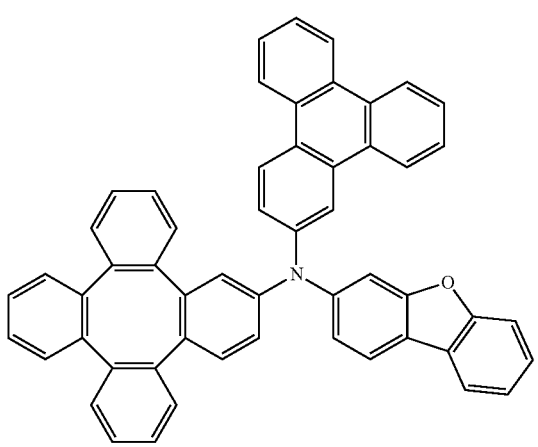

Compound 209
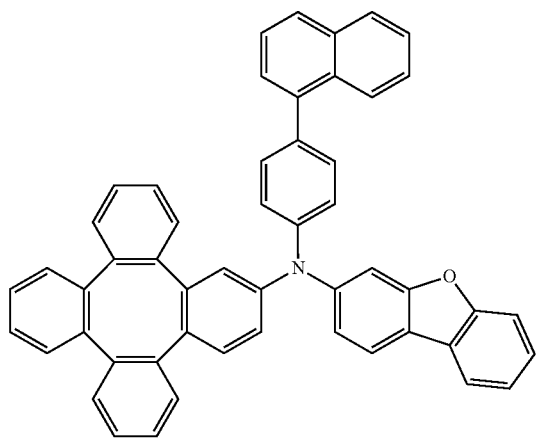
Compound 210
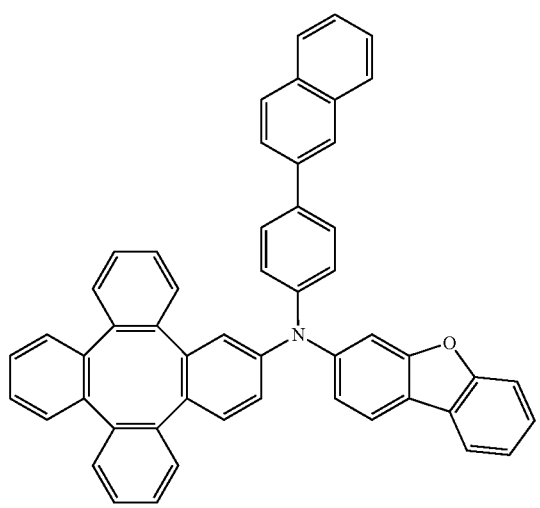
Compound 222
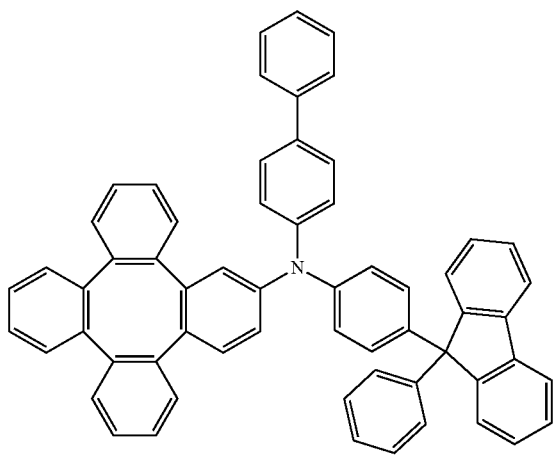
Compound 223
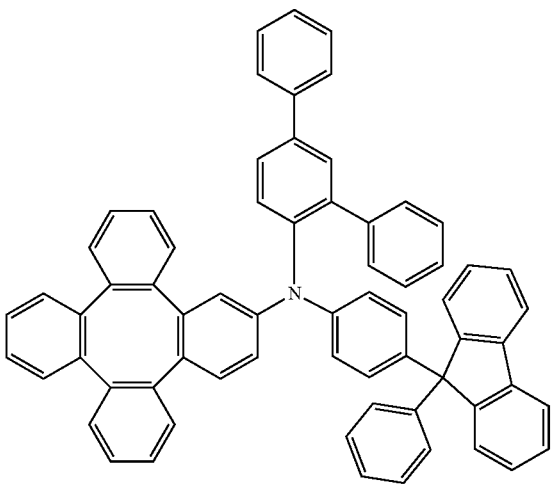
Compound 224
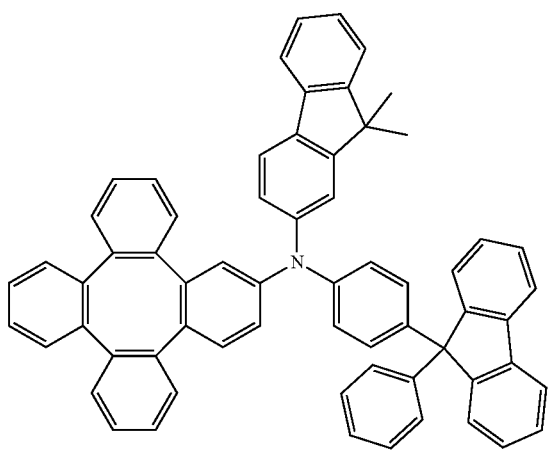
Compound 225
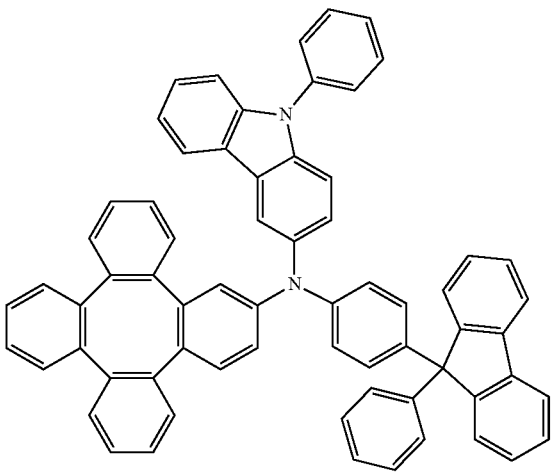

Compound 228
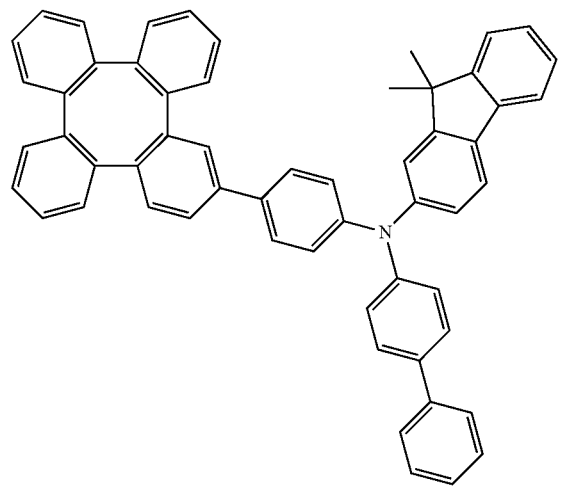

Compound 229
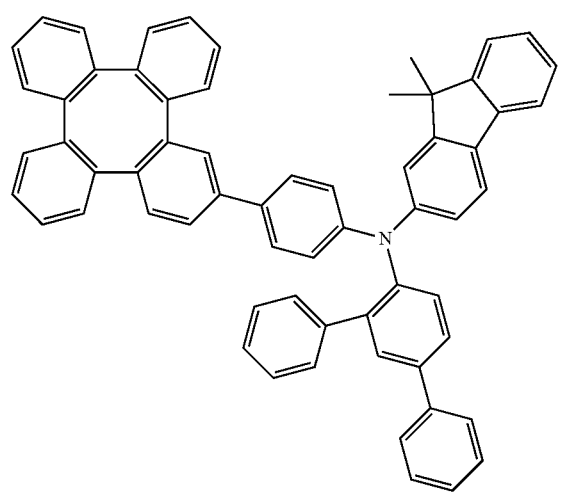

Compound 230
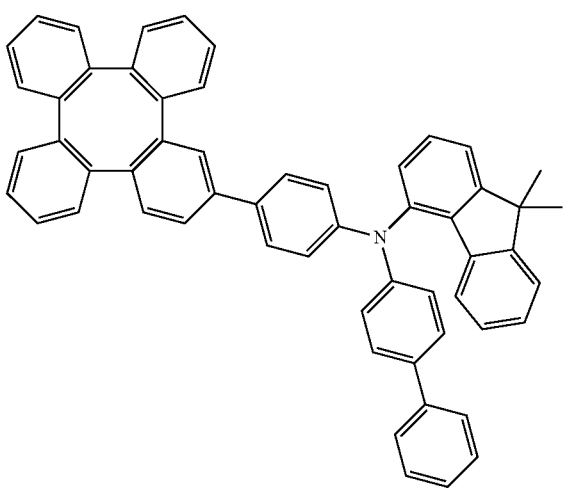

Compound 231
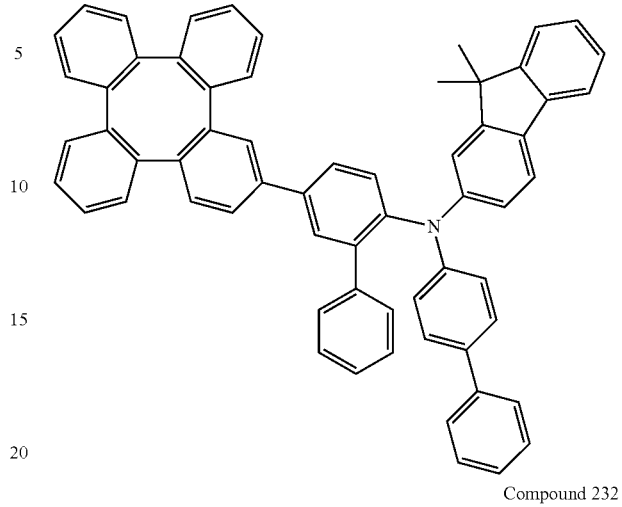

Compound 232
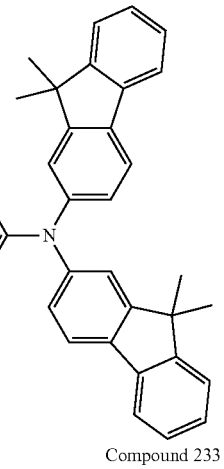

Compound 233
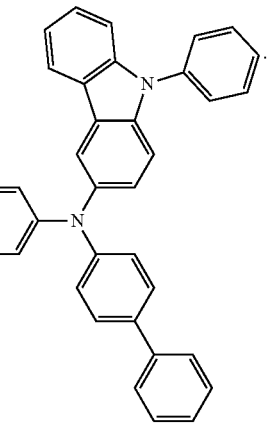

5. An organic electroluminescent device which comprises an anode, a cathode, a series of organic layers disposed between the anode and cathode, wherein at least one of the organic layers comprises the hole transporting compound of claim 1.

6. The device of claim 5, wherein the device comprises an electron blocking layer, wherein the electron blocking layer comprises the hole transporting compound of claim 1.

7. The device of claim 5, wherein the device comprises a hole transporting layer, wherein the hole transporting layer comprises the hole transporting compound of claim 1.

8. The device of claim 5, wherein the device comprises a hole injection layer, wherein the hole injection layer comprises the hole transporting compound of claim 1.

9. The device of claim 8, wherein the hole injection layer further comprises a p-type conductive dopant.

10. A formulation comprising the hole transporting compound of claim 1.

11. The hole transporting compound of claim 1, wherein the hole transporting compound is represented by Formula 2.

12. The hole transporting compound of claim 1, wherein:
   the hole transporting compound is represented by Formula 3;
   X is selected from the group consisting of O, S, Se, NR; and
   Y is selected from CR'R".

13. The hole transporting compound of claim 1, wherein:
   the hole transporting compound is represented by Formula 3;
   X is selected from the group consisting of O, S, Se; and
   Y is selected from CR'R".

\* \* \* \* \*